United States Patent
Hagel et al.

(10) Patent No.: US 11,891,360 B2
(45) Date of Patent: Feb. 6, 2024

(54) GLYCOSYLATED PSILOCYBIN DERIVATIVES AND METHODS OF USING

(71) Applicant: Enveric Biosciences Canada Inc., Calgary (CA)

(72) Inventors: Jillian M. Hagel, Calgary (CA); Peter J. Facchini, Calgary (CA); Chang-Chun Ling, Calgary (CA)

(73) Assignee: Enveric Biosciences Canada Inc., Calgary (CA)

( * ) Notice: Subject to any disclaimer, the term of this patent is extended or adjusted under 35 U.S.C. 154(b) by 0 days.

(21) Appl. No.: 17/941,425

(22) Filed: Sep. 9, 2022

(65) Prior Publication Data

US 2023/0086396 A1    Mar. 23, 2023

Related U.S. Application Data

(63) Continuation of application No. PCT/CA2021/051185, filed on Aug. 26, 2021.

(60) Provisional application No. 63/070,491, filed on Aug. 26, 2020.

(51) Int. Cl.
   C07D 209/20    (2006.01)
   C07H 17/02    (2006.01)

(52) U.S. Cl.
   CPC .......... *C07D 209/20* (2013.01); *C07H 17/02* (2013.01)

(58) Field of Classification Search
   CPC .................................................. C07D 209/20
   See application file for complete search history.

(56) References Cited

U.S. PATENT DOCUMENTS

2021/0403425 A1* 12/2021 Bryson ................ A61K 9/0053

FOREIGN PATENT DOCUMENTS

| CN | 109350724 A | 2/2019 |
| WO | WO2007032551 A1 | 3/2009 |
| WO | WO2014115113 A1 | 7/2014 |
| WO | WO2022040802 A1 | 3/2022 |

OTHER PUBLICATIONS

Walther, et al. Advanced Drug Delivery Reviews 118 (2017) 65-77.*
Daniel, J. et al. Clinical potential of psilocybin as a treatment for mental health conditions. Mental Health Clin/, 2017;7(1): 24-28.
Grob, C. et al. Pilot study of psilocybin treatment for anxiety in patients with advanced-stage cancerArch. Gen. Psychiatry, 2011, 68(1) 71-78.
Cathart-Harris, R.L. et al. Psilocybin with psychological support for treatment-resistant depression: an open-label feasibility study. Lancet Psychiatry, 2016, 3: 619-627.
Devereux et al., A comprehensive set of sequence analysis programs for the VAX. Nucleic Acids Res., 1984, 12: 387.
Thompson, J D, Higgines, D G and Gibson T J. Clustal W: improving the sensitivity of progressive multiple sequence alignment through sequence weighting, position-specific gap penalties and weight matrix choice. 1994, Nucleic Acid Res 22(22): 4673-4680.
S. Kawai et al., Transformation of *Saccharomyces cerevisiae* and other fungi: methods and possible underlying mechanism. Bioeng Bugs. Nov.-Dec. 2010;1(6):395-403.
Henikoff S & Henikoff, J G, Amino acid substitution matrices from protein blocks. Proc Natl Acad Sci U S A. Nov. 15, 1992;89(22):10915-9.
Pyrgiotakis G. et al., Cell death discrimination with Raman spectroscopy and support vector machines. 2009, Ann. Biomed. Eng. 37: 1464-1473.
L. S. Krasavina et al; "Synthesis of O-(f3-D-glucopyranosyl) serotonin". Doklady Akademii Nauk SSSR 1971, 196(3), 597-599. Chemical Abstracts Access No. 1974: 420870.
L. S. Krasavina et al, "The N- and 0-glycosides of indolylalkylamines. IV. Synthesis of O-(/3-D-galactopyranosyl) serotonin". Zhumal Organicheskoi Khimii 1974, vol. 10(2), pp. 206-208. Chemical Abstracts Access No. 1974:121273.
Maneski, et al; "Glucuronidation of Psilocin and 4-Hydroxyindole by the Human UDP-Glucuronosyltransferases". Drug Metabolism And Disposition Mar. 1, 2010 (Jan. 3, 2010), vol. 38( 3), pp. 386-395.
Kayoko Ohura, Yuichiro Nakada, Teruko Imai. Bioconversion and P-gp-Mediated Transport of Depot Fluphenazine Prodrugs after Intramuscular Injection. Journal of Pharmaceutical Sciences 112 (2023) 1975!1984.
Altschul et al., Basic local alignment search tool. J Mol Biol. Oct. 5, 1990;215(3):403-10.
Carillo and Lipton. SIAM J. Applied Math., 1988, 48:1073.
Cregg et al., Recombinant protein expression in Pichia pastoris. Mol Biotechnol. (2000) 16(1): 23-52.
Finnin, B. and Morgan, T.M., Transdermal penetration enhancers: applications, limitations, and potential J Pharm Sci. Oct. 1999;88(10):955-8.
Mattanovich et al., Recombinant protein production in yeasts. Methods Mol. Biol., 2012, 824:329-58.
Needleman and Wunsch. A general method applicable to the search for similarities in the amino acid sequence of two proteins J. Mol. Biol., 1970, 48: 443.
Rickli A. et al., 2016, Europ. Neuropsychopharmacol., 26: 1326-1337.
Romanos et al., Foreign gene expression in yeast: a review. Yeast. Jun. 1992;8(6):423-88.
Smith and Waterman. Adv. Appl. Math., 1981, 2: 482.

* cited by examiner

*Primary Examiner* — Shawquia Jackson
(74) *Attorney, Agent, or Firm* — BERESKIN & PARR LLP/S.E.N.C.R.L., s.r.l.; Michael Fenwick

(57) ABSTRACT

Disclosed are novel glycosylated psilocybin derivative compounds and pharmaceutical and recreational drug formulations containing the same. The compounds may be produced by reacting a hydroxylated psilocybin derivative with a glycosyl compound.

26 Claims, 26 Drawing Sheets
Specification includes a Sequence Listing.

GLYCOSYLATED PSILOCYBIN DERIVATIVES AND METHODS OF USING

RELATED APPLICATION

This application is a continuation of PCT Application No. PCT/CA2021/051185 filed Aug. 26, 2021, which claims the benefit of U.S. Provisional Application No. 63/070,491 filed Aug. 26, 2020; the entire contents of Patent Application Nos. PCT/CA2021/051185 and 63/070,491 are hereby incorporated by reference.

INCORPORATION OF SEQUENCE LISTING

A computer readable form of the Sequence Listing "29664-P62531US01_SequenceListing.xml" (20,480 bytes), submitted via EFS-WEB and created on Sep. 9, 2022, is herein incorporated by reference.

FIELD OF THE DISCLOSURE

The compositions and methods disclosed herein relate to a chemical compound known as psilocybin. Furthermore, the compositions and methods disclosed herein relate in particular to glycosylated forms of psilocybin.

BACKGROUND OF THE DISCLOSURE

The following paragraphs are provided by way of background to the present disclosure. They are not however an admission that anything discussed therein is prior art or part of the knowledge of a person of skill in the art.

The biochemical pathways in the cells of living organisms may be classified as being part of primary metabolism, or as being part of secondary metabolism. Pathways that are part of a cell's primary metabolism are involved in catabolism for energy production or in anabolism for building block production for the cell. Secondary metabolites, on the other hand, are produced by the cell without having an obvious anabolic or catabolic function. It has long been recognized that secondary metabolites can be useful in many respects, including as therapeutic compounds.

Psilocybin, for example, is a secondary metabolite that is naturally produced by certain mushrooms which taxonomically can be classified as belonging the Basidiomycota division of the fungi kingdom. Mushroom species which can produce psilocybin include species belonging to the genus Psilocybe, such as *Psilocybe azurescens, Psilocybe semilanceata, Psilocybe serbica, Psilocybe mexicana,* and *Psilocybe cyanescens*, for example. The interest of the art in psilocybin is well established. Thus, for example, psilocybin is a psychoactive compound and is therefore used as a recreational drug. Furthermore, psilocybin is used as a research tool in behavioral and neuro-imaging studies in psychotic disorders, and has been evaluated for its clinical potential in the treatment of mental health conditions (Daniel, J. et al. Mental Health Clin/, 2017; 7(1): 24-28), including to treat anxiety in terminal cancer patients (Grob, C. et al. Arch. Gen. Psychiatry, 2011, 68(1) 71-78) and to alleviate symptoms of treatment-resistant depression (Cathart-Harris, R. L. et al. Lancet Psychiatry, 2016, 3: 619-627).

Although the toxicity of psilocybin is low, adverse side effects, including, for example, panic attacks, paranoia and psychotic states, sometimes together or individually referred to as "a bad trip", are not infrequently experienced by recreational psilocybin users.

There exists therefore a need in the art for improved psilocybin compounds.

SUMMARY OF THE DISCLOSURE

The following paragraphs are intended to introduce the reader to the more detailed description, not to define or limit the claimed subject matter of the present disclosure.

In one aspect, the present disclosure relates to psilocybin and derivative compounds.

In another aspect, the present disclosure relates to glycosylated psilocybin derivative compounds and methods of making and using these compounds.

Accordingly, in one aspect, the present disclosure provides, in at least one embodiment, in accordance with the teachings herein, a chemical compound or salt thereof having formula (I):

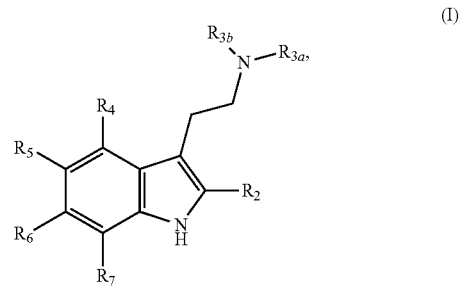

wherein at least one of $R_2$, $R_4$, $R_5$, $R_6$, or $R_7$ is a glycosyl group, and wherein each non-glycosylated $R_2$, $R_5$, $R_6$, or $R_7$ is a hydrogen atom or an alkyl group or O-alkyl group, wherein $R_4$ when it is not glycosylated is a hydrogen atom, alkyl group or O-alkyl group, or a phosphate group, and wherein $R_{3A}$ and $R_{3B}$ are a hydrogen atom, an alkyl group, an aryl group, or an acyl group.

In at least one embodiment, in an aspect, the glycosyl group can be a glycosyloxy group.

In at least one embodiment, in an aspect, the glycosyl group can be a C-linked glycosyl group.

In at least one embodiment, in an aspect, the glycosyl group can be bonded in the furanose or pyranose form from its anomeric carbon atom.

In at least one embodiment, in an aspect, $R_2$ can be a glycosyl group, $R_5$, $R_6$ and $R_7$ can each be a hydrogen atom or an alkyl group or O-alkyl group, and $R_4$ can be a phosphate group, a hydrogen atom or an alkyl group or O-alkyl group.

In at least one embodiment, in an aspect, $R_4$ can be a glycosyl group and $R_2$, $R_5$, $R_6$ and $R_7$ can each be a hydrogen atom or an alkyl group or O-alkyl group.

In at least one embodiment, in an aspect, $R_5$ can be a glycosyl group, $R_2$, $R_6$ and $R_7$ can each be a hydrogen atom or an alkyl group or O-alkyl group, and $R_4$ can be a phosphate group, a hydrogen atom or an alkyl group or O-alkyl group.

In at least one embodiment, in an aspect, $R_6$ can be a glycosyl group atom, $R_2$, $R_5$ and $R_7$ can each be a hydrogen atom or an alkyl group or O-alkyl group, and $R_4$ can be a phosphate group, a hydrogen atom or an alkyl group or O-alkyl group.

In at least one embodiment, in an aspect, $R_7$ can be a glycosyl group atom, $R_2$, $R_5$ and $R_6$ can each be a hydrogen atom or an alkyl group or O-alkyl group, and $R_4$ can be a phosphate group, a hydrogen atom or an alkyl group or O-alkyl group.

In at least one embodiment, in an aspect, at least two of $R_2$, $R_4$, $R_5$, $R_6$ or $R_7$ can be a glycosyl group.

In at least one embodiment, in an aspect, the at least of two of $R_2$, $R_4$, $R_5$, $R_6$ or $R_7$ that are glycosyl groups can each be glycosyloxy groups.

In at least one embodiment, in an aspect, the at least of two of $R_2$, $R_4$, $R_5$, $R_6$ or $R_7$ that are glycosyl groups can each be C-linked glycosyl groups.

In at least one embodiment, in an aspect, the at least of two of $R_2$, $R_4$, $R_5$, $R_6$ or $R_7$ that are glycosyl groups can be at least one glycosyloxy group and at least one C-linked glycosyl group.

In at least one embodiment, in an aspect, $R_2$ and $R_4$ can be a glycosyl group, and $R_5$, $R_6$ and $R_7$ can be a hydrogen atom or an alkyl group or O-alkyl group.

In at least one embodiment, in an aspect, $R_2$ and $R_5$ can be a glycosyl group, $R_6$ and $R_7$ can be a hydrogen atom or an alkyl group or O-alkyl group, and $R_4$ can be a hydrogen atom, an alkyl group or O-alkyl group or a phosphate group.

In at least one embodiment, in an aspect, $R_2$ and $R_6$ can be a glycosyl group, $R_5$ and $R_7$ can be a hydrogen atom or an alkyl group or O-alkyl group, and $R_4$ can be a hydrogen atom, an alkyl group or O-alkyl group or a phosphate group.

In at least one embodiment, in an aspect, $R_2$ and $R_7$ can be a glycosyl group, $R_5$ and $R_6$ can be a hydrogen atom or an alkyl group or O-alkyl group, and $R_4$ can be a hydrogen atom, an alkyl group or O-alkyl group or a phosphate group.

In at least one embodiment, in an aspect, $R_4$ and $R_5$ can be a glycosyl group, and $R_2$, $R_6$ and $R_7$ can be a hydrogen atom or an alkyl group or O-alkyl group.

In at least one embodiment, in an aspect, $R_4$ and $R_6$ can be a glycosyl group, and $R_2$, $R_5$ and $R_7$ can be a hydrogen atom or an alkyl group or O-alkyl group.

In at least one embodiment, in an aspect, $R_4$ and $R_7$ can be a glycosyl group and $R_2$, $R_5$ and $R_6$ can be a hydrogen atom or an alkyl group or O-alkyl group.

In at least one embodiment, in an aspect, $R_5$ and $R_6$ can be a glycosyl group, $R_2$ and $R_7$ can be a hydrogen atom or an alkyl group or O-alkyl group, and $R_4$ can be a hydrogen atom, an alkyl group or O-alkyl group or a phosphate group.

In at least one embodiment, in an aspect, $R_5$ and $R_7$ can be a glycosyl group, $R_2$ and $R_6$ can be a hydrogen atom or an alkyl group or O-alkyl group, and $R_4$ can be a hydrogen atom, an alkyl group or O-alkyl group or a phosphate group.

In at least one embodiment, in an aspect, $R_6$ and $R_7$ can be a glycosyl group, $R_2$ and $R_5$ can be a hydrogen atom or an alkyl group or O-alkyl group, and $R_4$ can be a hydrogen atom, an alkyl group or O-alkyl group or a phosphate group.

In at least one embodiment, in an aspect, $R_4$ when it is not glycosylated can be a hydrogen atom.

In at least one embodiment, in an aspect, $R_4$ when it is not glycosylated can be an alkyl group or O-alkyl group.

In at least one embodiment, in an aspect, $R_4$ when it is not glycosylated can be a phosphate group.

In at least one embodiment, in an aspect, three, four or all five of $R_2$, $R_4$, $R_5$, $R_6$ or $R_7$ can be a glycosyl group.

In at least one embodiment, in an aspect, the three, four, or five of $R_2$, $R_4$, $R_5$, $R_6$ or $R_7$ that are glycosyl groups can all be glycosyloxy groups.

In at least one embodiment, in an aspect, the three, four, or five of $R_2$, $R_4$, $R_5$, $R_6$ or $R_7$ that are glycosyl groups can all be C-linked glycosyl groups.

In at least one embodiment, in an aspect, the three, four, or five of $R_2$, $R_4$, $R_5$, $R_6$ or $R_7$ that are glycosyl groups can include at least one C-linked glycosyl group and at least one glycosyloxy group.

In at least one embodiment, in an aspect, the glycosyl group can be selected from a mono-saccharide, di-saccharide or tri-saccharide.

In at least one embodiment, in an aspect, the glycosyl group can be a poly-saccharide.

In at least one embodiment, in an aspect, the glycosyl group can be selected from a pentosyl group, a hexosyl group and a heptosyl group.

In at least one embodiment, in an aspect, the glycosyl group can be selected from a glucosyl group, a glucuronic acid group, a galactosyl group, a mannosyl group, a fucosyl group, a xylosyl group, an arabinosyl group, a rhamnosyl group, a glucosaminyl group and a galactosaminyl group.

In at least one embodiment, in an aspect, the chemical compound can be selected from the group consisting of compounds having formulas (III); (IV); (V); and (VI):

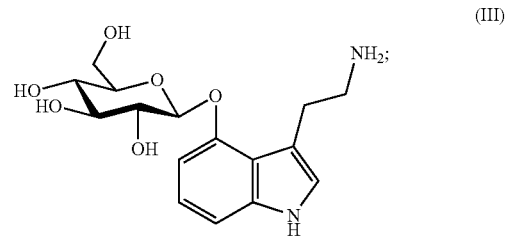

(III)

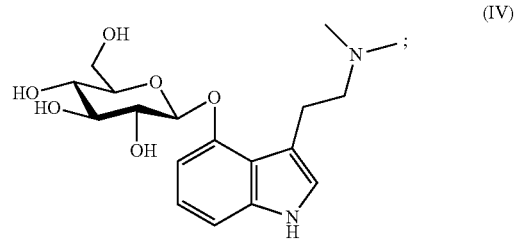

(IV)

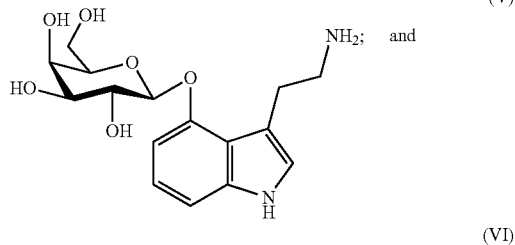

(V)

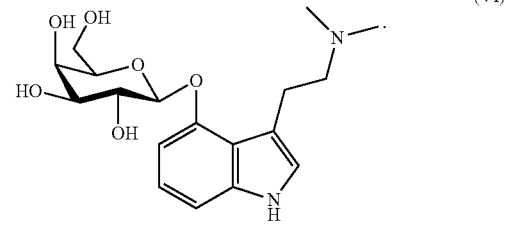

(VI)

In another aspect, the present disclosure relates to pharmaceutical and recreational drug formulations comprising glycosylated psilocybin derivatives. Accordingly, in one aspect, the present disclosure provides, in at least one embodiment, a pharmaceutical or recreational drug formulation comprising an effective amount of a chemical compound or salt thereof having formula (I):

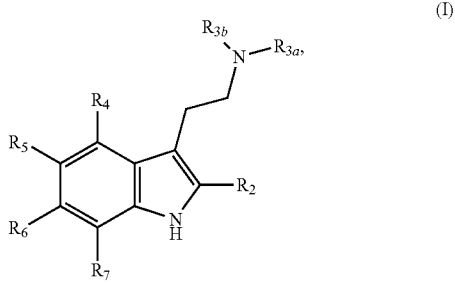
(I)

wherein at least one of $R_2$, $R_4$, $R_5$, $R_6$, or $R_7$ is a glycosyl group, and wherein each non-glycosylated $R_2$, $R_5$, $R_6$, or $R_7$ is a hydrogen atom or an alkyl group or O-alkyl group, wherein $R_4$ when it is not glycosylated is a hydrogen atom, an alkyl group or O-alkyl group or a phosphate group, and wherein $R_{3A}$ and $R_{3B}$ are a hydrogen atom, an alkyl group, an aryl group, or an acyl group, together with a pharmaceutically acceptable diluent, excipient or carrier.

In another aspect, the present disclosure relates to methods of treatment of psychiatric disorders. Accordingly, the present disclosure further provides, in at least one embodiment, a method for treating a psychiatric disorder, the method comprising administering to a subject in need thereof a pharmaceutical formulation comprising a chemical compound or salt thereof having formula (I):

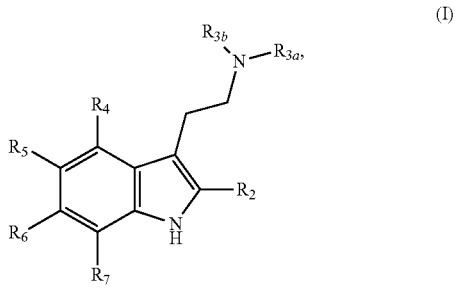
(I)

wherein at least one of $R_2$, $R_4$, $R_5$, $R_6$, or $R_7$ is a glycosyl group, and wherein each non-glycosylated $R_2$, $R_5$, $R_6$, or $R_7$ is a hydrogen atom or an alkyl group or O-alkyl group, wherein $R_4$ when it is not glycosylated is a hydrogen atom, an alkyl group or O-alkyl group or a phosphate group, and wherein $R_{3A}$ and $R_{3B}$ are a hydrogen atom, an alkyl group, an aryl group, or an acyl group, together with a pharmaceutically acceptable diluent, excipient or carrier, wherein the pharmaceutical formulation is administered in an effective amount to treat the psychiatric disorder in the subject.

In at least one embodiment, in an aspect, the disorder can be a 5-$HT_{2A}$ receptor mediated disorder.

In at least one embodiment, in an aspect, a dose can be administered of about 0.001 mg to about 5,000 mg.

In another aspect, the present disclosure relates to methods of making glycosylated psilocybin derivatives. Accordingly, in one aspect, the present disclosure provides, in at least one embodiment, a method of making a glycosylated psilocybin derivative, the method comprising:

contacting a hydroxy-containing psilocybin derivative compound or a salt thereof having the formula (II):

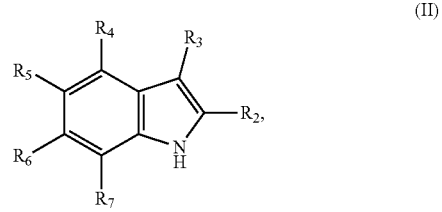
(II)

wherein at least one of $R_2$, Ra, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein $R_3$ is a hydrogen atom, a 2-aminoethyl group, or an N-substituted 2-aminoethyl group, and wherein $R_4$ when it is not hydroxylated is a hydrogen atom, an alkyl group or O-alkyl group or a phosphate group with a glycosyl donor compound under reaction conditions suitable to form a glycosylated psilocybin derivative, wherein the glycosylated psilocybin derivative is a chemical compound or salt thereof having formula (I):

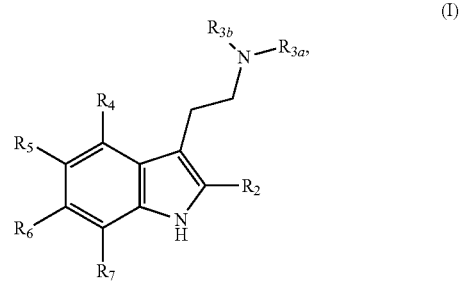
(I)

wherein at least one of $R_2$, $R_4$, $R_5$, $R_6$, or $R_7$ is a glycosyl group, and wherein each non-glycosylated $R_2$, $R_5$, $R_6$, or $R_7$ is a hydrogen atom or an alkyl group or O-alkyl group, wherein $R_4$ when it is not glycosylated is a hydrogen atom, an alkyl group or O-alkyl group or a phosphate group, and wherein $R_{3A}$ and $R_{3B}$ are a hydrogen atom, an alkyl group, an aryl group, or an acyl group, and wherein in the formation of the glycosylated psilocybin derivative at least one glycosyl group substitutes the at least one hydroxy group.

In at least one embodiment, in an aspect, the glycosyl group can be a glycosyloxy group.

In at least one embodiment, in an aspect, the glycosyl group can be a C-linked glycosyl group.

In at least one embodiment, the glycosyl donor compound can be selected from a mono-saccharide, a di-saccharide, an oligo-saccharide or a poly-saccharide.

In at least one embodiment, in an aspect, the glycosyl donor compound can be a compound having the formula (VIII) or (IX):

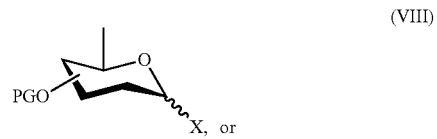
(VIII)

X, or

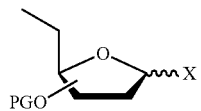

wherein PG is a protective group, wherein and X is a leaving group, and wherein the glycosyl donor compound reacts with the hydroxy-containing psilocybin derivative compound to form the compounds having the formula (X) or (XI):

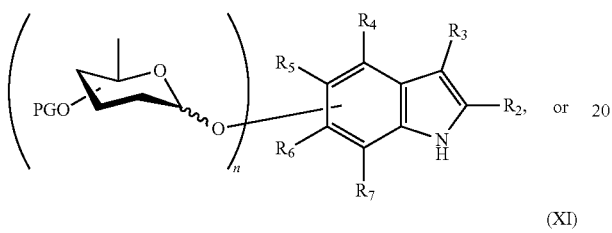

wherein PG is a protective group, and $R_3$ is a hydrogen atom, a 2-aminoethyl group, an N-substituted 2-aminoethyl group, a 2-azidoethyl group, or a 2-nitroethyl group, wherein the glycosyl group is bonded to at least one of $R_2$, $R_4$, $R_5$, $R_6$, or $R_7$ wherein n=1–5; and wherein the method further includes substituting the protective groups of the compounds having the formula (X) or (XI) by hydroxy groups to thereby form the compound having the formula (I).

In at least one embodiment, in an aspect, the compounds having the formulas (II) and (VIII) can be reacted in the presence of a Lewis acid or a base.

In at least one embodiment, in an aspect, the protective group can be an acyl or benzyl group, and the leaving group can be a halogen, imidate, alkylthio, or acyloxy group.

In at least one embodiment, in an aspect, $R_3$ is a hydrogen atom, and the method further comprises:

(a) reacting the compounds having the formula (X) or (XI) with 1-(dimethylamino)-2-nitroethylene in dichloromethane under the catalysis of an acid to form a compound having formula (XII) or (XIII):

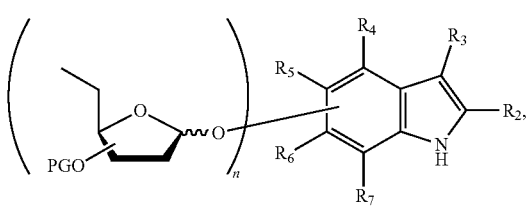

or

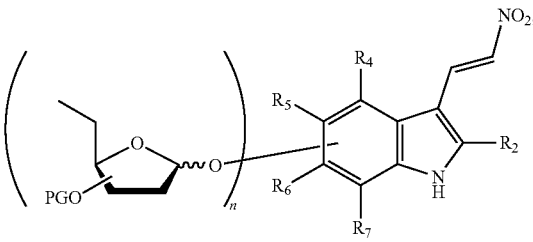

wherein PG is a protective group, wherein the glycosyl group is bonded to at least one of $R_2$, Ra, $R_5$, $R_6$, or $R_7$, and wherein n=1–5;

(b) reacting the compounds having the formula (XII) or (XIII) with sodium borohydride in an alcohol solution to form a compound having formula (XIV) or (XV):

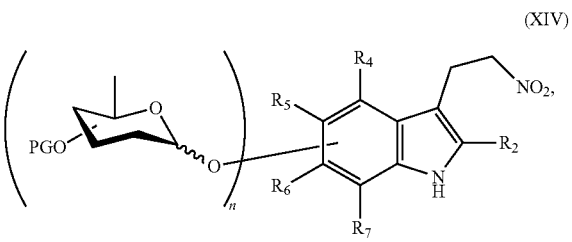

or

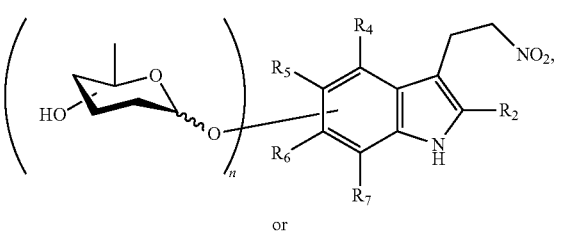

wherein PG is a protective group, wherein the glycosyl group is bonded to at least one of $R_2$, $R_4$, $R_5$, $R_6$, or $R_7$, and wherein n=1–5;

(c) reacting the compounds having formula (XIV) or (XV) under suitable conditions to remove the protecting group to form a compound having the formula (XVI) or (XVII):

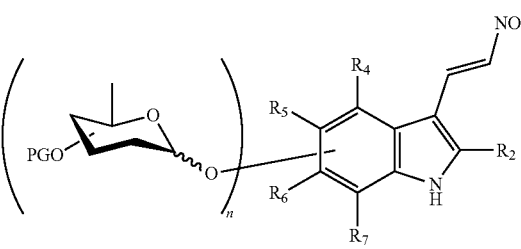

or

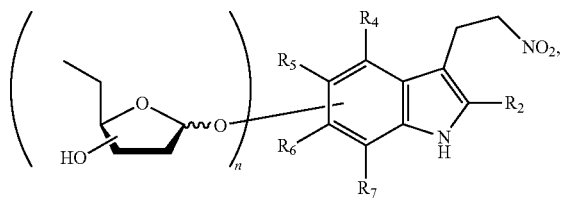
(XVII)

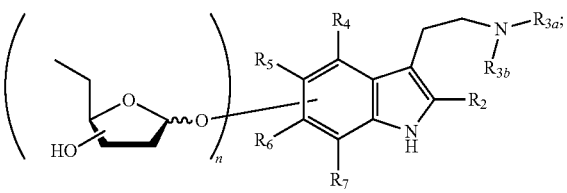
(XXI)

wherein the glycosyl group is bonded to at least one of $R_2$, $R_4$, $R_5$, $R_6$, or $R_7$, and wherein n=1–5; and (d) reacting the compounds having formula (XVI) or (XVII) under reducing conditions to form a compound having formula (XVIII) or (XIX):

wherein the glycosyl group is bonded to at least one of $R_2$, $R_4$, $R_5$, $R_6$, or $R_7$, and wherein n=1–5, and wherein $R_{3a}$ or $R_{3b}$ are an alkyl group or an aryl group.

In at least one embodiment, in an aspect, the compounds having formula (XX) or (XXI) can further be reacted with an acylating reagent in an alcohol or water solution to form a compound having formula (XXII) or (XXIII):

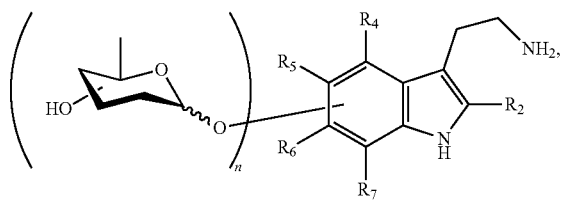
(XVIII)

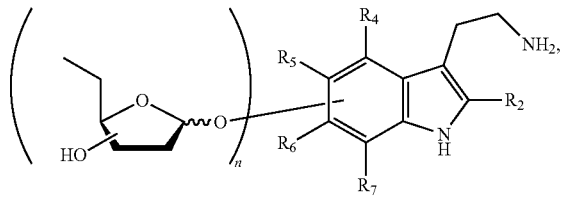
(XIX)

wherein the glycosyl group is bonded to at least one of $R_2$, $R_4$, $R_5$, $R_6$, or $R_7$, and wherein n=1–5.

In at least one embodiment, in an aspect, the compounds having formula (XVIII) or (XVI) can further be reacted with (i) an aldehyde or ketone group under reductive amination conditions or (ii) with an alkyl electrophile or α,β-unsaturated reagent, to form a compound having formula (XX) or (XXI):

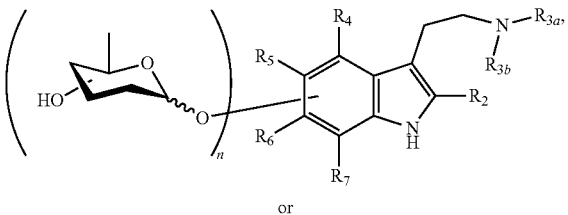
(XX)

or

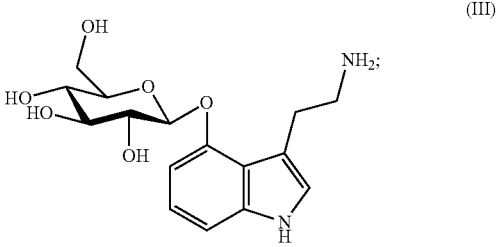
(XXII)

or (XXIII)

wherein the glycosyl group is bonded to at least one of $R_2$, $R_4$, $R_5$, $R_6$, or $R_7$, and wherein n=1–5, and wherein $R_{3a}$ or $R_{3b}$ are an alkyl group or an aryl group.

In at least one embodiment, in an aspect, the glycosylated psilocybin derivative can be selected from the group consisting of compounds having formulas (III); (IV); (V); and (VI):

(III)

-continued

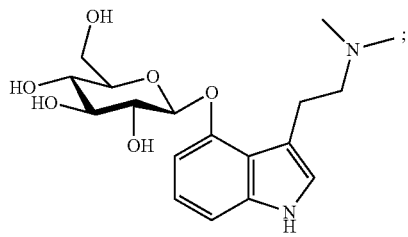
(IV)

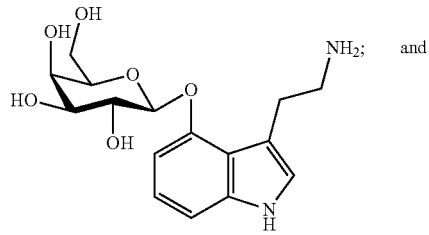
(V)

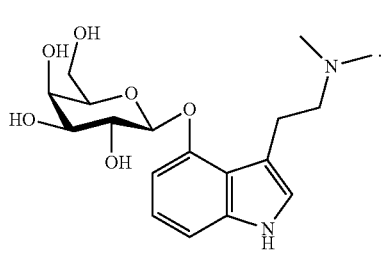
(VI)

In at least one embodiment, in an aspect, the hydroxy-containing psilocybin derivative compound can be contacted in a host cell comprising a glycosyl transferase, and the host cell is grown to produce the glycosylated psilocybin derivative.

In at least one embodiment, in an aspect, the glycosyl group can be a glycosyloxy group.

In at least one embodiment, in an aspect, the glycosyl group can be a C-linked glycosyl group.

In at least one embodiment, in an aspect, the glycosyl transferase can be encoded by a nucleic acid selected from:
(a) SEQ.ID NO: 1, SEQ.ID NO: 3, SEQ.ID NO: 5, SEQ.ID NO:7, and SEQ.ID NO: 9;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 2, SEQ.ID NO: 4, SEQ.ID NO: 6, SEQ.ID NO: 8, and SEQ.ID NO 10;
(f) a nucleic acid sequence that encodes a functional variant of any one of the amino acid sequences set forth in SEQ.ID NO: 2, SEQ.ID NO: 4, SEQ.ID NO: 6, SEQ.ID NO: 8, and SEQ.ID NO: 10; and
(g) a nucleic acid sequence that hybridizes under stringent conditions to any one of the nucleic acid sequences set forth in (a), (b), (c), (d), (e) or (f).

In at least one embodiment, in an aspect, the method can further include a step comprising isolating the glycosylated psilocybin derivative compound.

In at least one embodiment, in an aspect, the host cell can be a microbial cell.

In at least one embodiment, in an aspect, the host cell can be a bacterial cell or a yeast cell.

In another aspect, the present disclosure provides, in at least one embodiment, a method for modulating a 5-$HT_{2A}$ receptor, the method comprising contacting a 5-$HT_{2A}$ receptor with a chemical compound or salt thereof having formula (I):

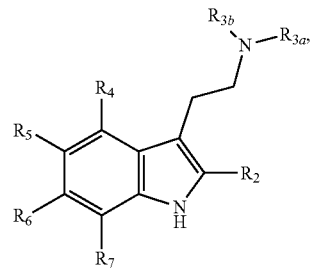
(I)

wherein at least one of $R_2$, $R_4$, $R_5$, $R_6$, or $R_7$ is a glycosyl group, and wherein each non-glycosylated $R_2$, $R_5$, $R_6$, or $R_7$ is a hydrogen atom or an alkyl group or O-alkyl group, wherein $R_4$ when it is not glycosylated is a hydrogen atom, an alkyl group or O-alkyl group or a phosphate group, and wherein $R_{3A}$ and $R_{3B}$ are a hydrogen atom, an alkyl group, an aryl group, or an acyl group under reaction conditions sufficient to thereby modulate receptor activity.

In some embodiments, in an aspect, the reaction conditions can be in vitro reaction conditions.

In some embodiments, in an aspect, the reaction conditions can be in vivo reaction conditions.

In another aspect, the present disclosure provides, in at least one embodiment, a use of a chemical compound or salt thereof having formula (I):

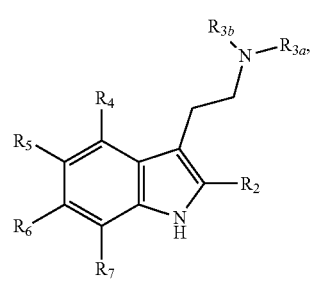
(I)

wherein at least one of $R_2$, Ra, $R_5$, $R_6$, or $R_7$ is a glycosyl group, and wherein each non-glycosylated $R_2$, $R_5$, $R_6$, or $R_7$ is a hydrogen atom or an alkyl group or O-alkyl group, wherein $R_4$ when it is not glycosylated is a hydrogen atom, an alkyl group or O-alkyl group or a phosphate group, and wherein $R_{3A}$ and $R_{3B}$ are a hydrogen atom, an alkyl group, an aryl group, or an acyl group, in the manufacture of a pharmaceutical or recreational drug formulation.

In at least one embodiment, in an aspect, the manufacture can comprise formulating the chemical compound with a pharmaceutically acceptable excipient, diluent or carrier.

In another aspect, the present disclosure provides, in at least one embodiment, a use of a chemical compound having formula (I):

(I)

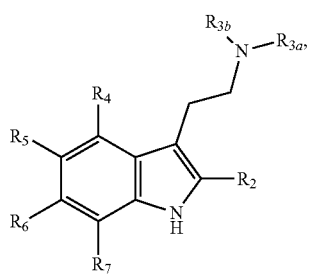

wherein at least one of $R_2$, $R_4$, $R_5$, $R_6$, or $R_7$ is a glycosyl group, and wherein each non-glycosylated $R_2$, $R_5$, $R_6$, or $R_7$ is a hydrogen atom or an alkyl group or O-alkyl group, wherein $R_4$ when it is not glycosylated is a hydrogen atom, an alkyl group or O-alkyl group or a phosphate group, and wherein $R_{3A}$ and $R_{3B}$ are a hydrogen atom, an alkyl group, an aryl group, or acyl group, together with a diluent, carrier, or excipient as a pharmaceutical or recreational drug formulation.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

Figure 1:
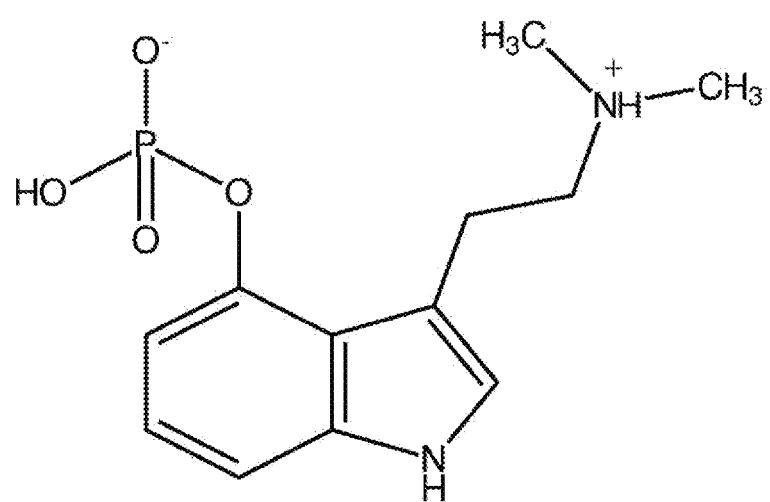
FIG. 1 depicts the chemical structure of psilocybin.

The figures together with the following detailed description make apparent to those skilled in the art how the disclosure may be implemented in practice.

DETAILED DESCRIPTION

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

As used herein and in the claims, the singular forms, such "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers.

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore any range of values described herein is intended to specifically include the limiting values of the range, and any intermediate value or sub-range within the given range, and all such intermediate values and sub-ranges are individually and specifically disclosed (e.g. a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents and patent applications are herein incorporated by reference in their entirety to the same extent as if each individual publication, patent or patent application was specifically and individually indicated to be incorporated by reference in its entirety.

Terms and Definitions

The term "psilocybin", refers to a chemical compound having the structure set forth in FIG. 1.

Figure 2:
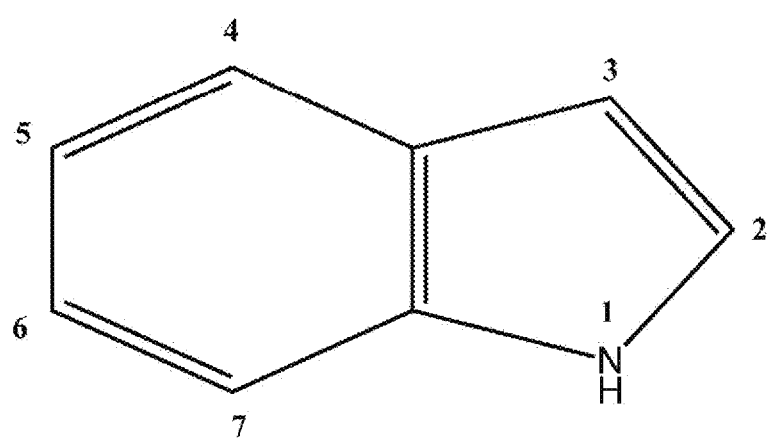
FIG. 2 depicts a certain prototype structure of psilocybin and psilocybin derivative compounds, namely an indole. Certain carbon and nitrogen atoms may be referred to herein by reference to their position within the indole structure, i.e. $N_1$, $C_2$, $C_3$ etc. The pertinent atom numbering is shown.

The term "indole prototype structure" refers to the chemical structure shown in FIG. 2. It is noted that specific carbon atoms and a nitrogen atom in the indole prototype structure are numbered. Reference may be made to these carbon and nitrogen numbers herein, for example $C_2$, $C_4$, $N_1$, and so forth. Furthermore, reference may be made to chemical groups attached to the indole prototype structure in accordance with the same numbering, for example $R_4$ and $R_6$ reference chemical groups attached to the $C_4$ and $C_6$ atom, respectively. In addition, $R_{3A}$ and $R_{3B}$, in this respect, reference chemical groups extending from the 2-aminoethyl group extending in turn from the $C_3$ atom of the prototype indole structure.

The terms "hydroxy-containing psilocybin derivative" or hydroxy-containing psilocybin derivative compound" refer to a psilocybin derivative compound comprising one or more hydroxy groups. Reference may be made to specific carbon atoms which may be hydroxylated. For example, a 7-hydroxy-psilocybin derivative refers to a hydroxylated psilocybin derivative in which carbon atom number 7 (as identified in the indole prototype structure) is hydroxylated, or, similarly, 2-hydroxy-psilocybin derivative refers to a hydroxylated psilocybin derivative in which carbon atom number 2 (as identified in the indole prototype structure) is hydroxylated. Thus, for example, hydroxy-containing psilocybin derivatives include, single hydroxy derivatives, 2-hydroxy, 4-hydroxy, 5-hydroxy, 6-hydroxy and 7-hydroxy psilocybin derivatives, for example, and multiple hydroxy derivatives, such as, for example, 4,7-dihydroxy-psilocybin derivatives, and 2,5,7-tri-hydroxy-psilocybin derivatives. The term hydroxy-containing psilocybin derivatives further includes chemical compounds having the chemical formula (II):

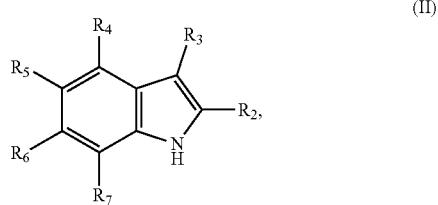

wherein at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein, $R_3$ is a hydrogen atom, a 2-aminoethyl group or a N-substituted 2-aminoethyl group, wherein $R_4$ when it is not hydroxylated is a hydrogen atom, an alkyl group or O-alkyl group or a phosphate group. The term further includes salts of hydroxy-containing psilocybin derivatives, such as a sodium salt, a potassium salt etc.

The terms "glycosylated" or "glycosyl", as used herein, refer to a saccharide group, such as a mono-, di-, tri- oligo- or a poly-saccharide group, which can be or has been bonded from its anomeric carbon either in the pyranose or furanose form, either in the α or the β conformation, or can be or has been bonded from a non-anomeric carbon atom, and can be in the pyranose or furanose form. The saccharide group can be bonded via an oxygen atom to another entity, the bonded saccharide group, inclusive of the oxygen atom, may be referred to herein as a "glycosyloxy" group, and can be said to be "O-glycosylated" or "O-linked". Thus, the term glycosyl group, as used herein, includes glucosyloxy groups. Alternatively, the saccharide group may also be bonded from a carbon atom, and can then be said to be "C-glycosylated" or "C-linked". Example monosaccharide groups include, but are not limited to, a pentosyl, a hexosyl, or a heptosyl group. The glycosyl group may also be substituted with various groups. Such substitutions may include lower alkyl, lower alkoxy, acyl, carboxy, carboxyamino, amino, acetamido, halo, thio, nitro, keto, and phosphatyl groups, wherein the substitution may be at one or more positions on the saccharide. Included in the term glycosyl are further stereoisomers, optical isomers, anomers, and epimers of the glycosyl group. Thus, a hexose group, for example, can be either an aldose or a ketose group, can be of D- or L-configuration, can assume either an α- or β-conformation, and can be a dextro- or levo-rotatory with respect to plane-polarized light. Example glycosyl groups further include, glucosyl group, glucuronic add group, a galactosyl group, a mannosyl group, a fucosyl group, a xylosyl group, an arabinosyl group, a rhamnosyl group, a glucosaminyl group and a galactosaminyl group.

The term "glycosylated psilocybin derivative" refers to a psilocybin derivative compound to which glycosyl group has been bonded to thereby form an O-linked or C-linked glycosyl bond. Reference may be made to specific carbon atoms which may be glycosylated. For example, a 5-glycosyl psilocybin derivative refers to a hydroxylated psilocybin derivative in which carbon atom number 5 (as identified in the indole prototype structure) is glycosylated, or, similarly, 4-glycosyl-psilocybin derivative refers to a glycosylated psilocybin derivative in which carbon atom number 4 (as identified in the indole prototype structure) is glycosylated. Thus, for example, glycosyl-containing psilocybin derivatives include, single glycosyl derivatives, 2-glycosyl, 4-glycosyl, 5-glycosyl, 6-glycosyl, and 7-glycosyl psilocybin derivatives, for example, and multiple glycosyl derivatives, such as, for example, 4,7-di-glycosyl psilocybin derivatives, and 2,5,7-tri-glycosyl psilocybin derivatives. The term glycosyl containing psilocybin derivatives further includes chemical compounds having the chemical formula (I):

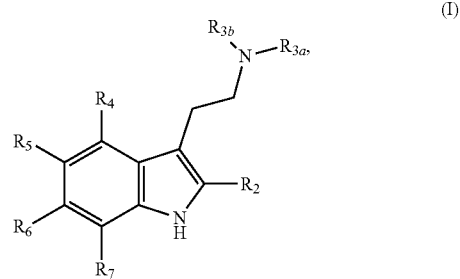

wherein at least one of $R_2$, $R_4$, $R_5$, $R_6$, or $R_7$ is a glycosyl group, and wherein each non-glycosylated $R_2$, $R_5$, $R_6$, or $R_7$ is a hydrogen atom or an alkyl group or O-alkyl group, wherein $R_4$ when it is not glycosylated is a hydrogen atom, an alkyl group or O-alkyl group or a phosphate group, and wherein $R_{3A}$ and $R_{3B}$ are a hydrogen atom, alkyl group, and aryl group or an acyl group. Glycosylated psilocybins further can include salts of chemical compounds having chemical formula (I), such as a sodium salt, a potassium salt etc.

The term "phosphate group", as used herein, is a molecule containing one atom of phosphorus, covalently bound to four oxygen atoms (three single bonds and one double bond). Of the four oxygen atoms one oxygen atom may be a hydroxy group, and one of the non-hydroxylated oxygen atom may be chemically bonded to another entity.

The terms "hydroxy group", and "hydroxy", as used herein, refers to a molecule containing one atom of oxygen bonded to one atom of hydrogen, and having the formula —OH. A hydroxy group through its oxygen atom may be chemically bonded to another entity.

The term "alkyl", as used herein, refers to a straight and/or branched chain, saturated alkyl radical containing from one to "p" carbon atoms ("$C_1$-$C_p$-alkyl") and includes, depending on the identity of "p", methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable p is an integer representing the largest number of carbon atoms in the alkyl radical. Alkyl groups further include hydrocarbon groups arranged in a chain having the chemical formula $-C_nH_{2n+1}$, including, without limitation, methyl groups ($-CH_3$), ethyl groups ($-C_2H_5$), propyl groups ($-C_3H_7$), and butyl groups ($-C_4H_9$).

The term "O-alkyl", as used herein, refers to a hydrocarbon group arranged in a chain having the chemical formula $-O-C_nH_{2n+1}$. O-alkyl groups include, without limitation, O-methyl groups ($-O-CH_3$), O-ethyl groups ($-O-C_2H_5$), O-propyl groups ($-O-C_3H_7$) and O-butyl groups ($-O-C_4H_9$).

The term "aryl", as used herein, refers to a monocyclic, bicyclic or tricyclic aromatic ring system containing, depending on the number of atoms in the rings, for example, from 6 to 14 carbon atoms ($C_6$-$C_{14}$-aryl) or from 6 to 10 carbons ($C_6$-$C_{10}$-aryl), and at least 1 aromatic ring and includes phenyl, naphthyl, anthracenyl, 1,2-dihydronaphthyl, 1,2,3,4-tetrahydronaphthyl, fluorenyl, phenanthrenyl, biphenylenyl, indanyl, indenyl and the like.

The term "acyl", as used herein, refers to a carbon atom double bonded to an oxygen and single bonded to an alkyl group. The carbon atom further can be bonded to another entity. An acyl group can be described by the chemical formula: $-C(=O)-C_nH_{2n+1}$.

The term "5-$HT_{2A}$ receptor", as used herein, refers to a subclass of a family of receptors for the neurotransmitter and peripheral signal mediator serotonin. 5-$HT_{2A}$ receptors can mediate a plurality of central and peripheral physiologic functions of serotonin. Central nervous system effects can include mediation of hallucinogenic effects of hallucinogenic compounds.

The term "modulating 5-$HT_{2A}$ receptors", as used herein, refers to the ability of a compound disclosed herein to alter the function of 5-$HT_{2A}$ receptors. A 5-$HT_{2A}$ receptor modulator may activate the activity of a 5-$HT_{2A}$ receptor, may activate or inhibit the activity of a 5-$HT_{2A}$ receptor depending on the concentration of the compound exposed to the 5-$HT_{2A}$ receptor, or may inhibit the activity of a 5-$HT_{2A}$ receptor. Such activation or inhibition may be contingent on the occurrence of a specific event, such as activation of a signal transduction pathway, and/or maybe manifest only in particular cell types. The term "modulating 5-$HT_{2A}$ receptors," also refers to altering the function of a 5-$HT_{2A}$ receptor by increasing or decreasing the probability that a complex forms between a 5-$HT_{2A}$ receptor and a natural binding partner to form a multimer. A 5-$HT_{2A}$ receptor modulator may increase the probability that such a complex forms between the 5-$HT_{2A}$ receptor and the natural binding partner, may increase or decrease the probability that a complex forms between the 5-$HT_{2A}$ receptor and the natural binding partner depending on the concentration of the compound exposed to the 5-$HT_{2A}$ receptor, and or may decrease the probability that a complex forms between the 5-$HT_{2A}$ receptor and the natural binding partner.

The term "5-$HT_{2A}$ receptor-mediated disorder", as used herein, refers to a disorder that is characterized by abnormal 5-$HT_{2A}$ receptor activity. A 5-$HT_{2A}$ receptor-mediated disorder may be completely or partially mediated by modulating 5-$HT_{2A}$ receptors. In particular, a 5-$HT_{2A}$ receptor-mediated disorder is one in which modulation of 5-$HT_{2A}$ receptors results in some effect on the underlying disorder e.g., administration of a 5-$HT_{2A}$ receptor modulator results in some improvement in at least some of the subjects being treated.

The term "pharmaceutical formulation", as used herein, refers to a preparation in a form which allows an active ingredient, including a psychoactive ingredient, contained therein to provide effective treatment, and which does not contain any other ingredients which cause excessive toxicity, an allergic response, irritation, or other adverse response commensurate with a reasonable risk/benefit ratio. The pharmaceutical formulation may contain other pharmaceutical ingredients such as excipients, carriers, diluents, or auxiliary agents.

The term "recreational drug formulation", as used herein, refers to a preparation in a form which allows a psychoactive ingredient contained therein to be effective for administration as a recreational drug, and which does not contain any other ingredients which cause excessive toxicity, an allergic response, irritation, or other adverse response commensurate with a reasonable risk/benefit ratio. The recreational drug formulation may contain other ingredients such as excipients, carriers, diluents, or auxiliary agents.

The term "effective for administration as a recreational drug", as used herein, refers to a preparation in a form which allows a subject to voluntarily induce a psychoactive effect for non-medical purposes upon administration, generally in the form of self-administration. The effect may include an altered state of consciousness, satisfaction, pleasure, euphoria, perceptual distortion, or hallucination.

The term "effective amount", as used herein, refers to an amount of an active agent, pharmaceutical formulation or recreational drug formulation, sufficient to induce a desired biological or therapeutic effect, including a prophylactic effect, and further including a psychoactive effect. Such effect can include an effect with respect to the signs, symptoms or causes of a disorder, or disease or any other desired alteration of a biological system. The effective amount can vary depending, for example, on the health condition, injury stage, disorder stage, or disease stage, weight, or sex of a subject being treated, timing of the administration, manner of the administration, age of the subject, and the like, all of which can be determined by those of skill in the art.

The terms "treating" and "treatment", and the like, as used herein, are intended to mean obtaining a desirable physiological, pharmacological, or biological effect, and includes prophylactic and therapeutic treatment. The effect may result in the inhibition, attenuation, amelioration, or reversal of a sign, symptom or cause of a disorder, or disease, attributable to the disorder, or disease, which includes mental and psychiatric diseases and disorders. Clinical evidence of the prevention or treatment may vary with the disorder, or disease, the subject and the selected treatment.

The term "pharmaceutically acceptable", as used herein, refers to materials, including excipients, carriers, diluents, or auxiliary agents, that are compatible with other materials in a pharmaceutical or recreational drug formulation and within the scope of reasonable medical judgement suitable for use in contact with a subject without excessive toxicity, allergic response, irritation, or other adverse response commensurate with a reasonable risk/benefit ratio.

The term "glycosyl transferase" as used herein, refers to any and all enzymes comprising a sequence of amino acid residues which is (i) substantially identical to the amino acid sequences constituting any glycosyl transferase polypeptide set forth herein, including, for example, SEQ.ID NO: 2, or (ii) encoded by a nucleic acid sequence capable of hybridizing under at least moderately stringent conditions to any nucleic acid sequence encoding any glycosyl transferase set forth herein, but for the use of synonymous codons.

The terms "nucleic acid sequence encoding a glycosyl transferase", and "nucleic acid sequence encoding a glycosyl transferase polypeptide", as may be used interchangeably herein, refer to any and all nucleic acid sequences encoding a glycosyl transferase polypeptide, including, for example, SEQ.ID NO: 1. Nucleic acid sequences encoding a glycosyl transferase polypeptide further include any and all nucleic acid sequences which (i) encode polypeptides that are substantially identical to the glycosyl transferase polypeptide sequences set forth herein; or (ii) hybridize to any glycosyl transferase nucleic acid sequences set forth herein under at least moderately stringent hybridization conditions or which would hybridize thereto under at least moderately stringent conditions but for the use of synonymous codons.

The terms "nucleic acid", or "nucleic acid sequence", as used herein, refer to a sequence of nucleoside or nucleotide monomers, consisting of naturally occurring bases, sugars and intersugar (backbone) linkages. The term also includes modified or substituted sequences comprising non-naturally occurring monomers or portions thereof. The nucleic acids of the present disclosure may be deoxyribonucleic nucleic acids (DNA) or ribonucleic acids (RNA) and may include naturally occurring bases including adenine, guanine, cytosine, thymidine and uracil. The nucleic acids may also contain modified bases. Examples of such modified bases include aza and deaza adenine, guanine, cytosine, thymidine and uracil, and xanthine and hypoxanthine. A sequence of nucleotide or nucleoside monomers may be referred to as a polynucleotide sequence, nucleic acid sequence, a nucleotide sequence or a nucleoside sequence.

The term "polypeptide", as used herein in conjunction with a reference SEQ.ID NO, refers to any and all polypeptides comprising a sequence of amino acid residues which is (i) substantially identical to the amino acid sequence constituting the polypeptide having such reference SEQ.ID NO, or (ii) encoded by a nucleic acid sequence capable of hybridizing under at least moderately stringent conditions to any nucleic acid sequence encoding the polypeptide having such reference SEQ.ID NO, but for the use of synonymous codons. A sequence of amino acid residues may be referred to as an amino acid sequence, or polypeptide sequence.

The term "nucleic acid sequence encoding a polypeptide", as used herein in conjunction with a reference SEQ.ID NO, refers to any and all nucleic acid sequences encoding a polypeptide having such reference SEQ.ID NO. Nucleic acid sequences encoding a polypeptide, in conjunction with a reference SEQ.ID NO, further include any and all nucleic acid sequences which (i) encode polypeptides that are substantially identical to the polypeptide having such reference SEQ.ID NO; or (ii) hybridize to any nucleic acid sequences encoding polypeptides having such reference SEQ.ID NO under at least moderately stringent hybridization conditions or which would hybridize thereto under at least moderately stringent conditions but for the use of synonymous codons.

By the term "substantially identical" it is meant that two amino acid sequences preferably are at least 70% identical, and more preferably are at least 85% identical and most preferably at least 95% identical, for example 96%, 97%, 98% or 99% identical. In order to determine the percentage of identity between two amino acid sequences the amino acid sequences of such two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Mol. Biol., 1990: 215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences wherein at least 50% of the total length of one of the two sequences is involved in the alignment.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.-16.6 (Log 10 [Na+])+0.41(% (G+C)-600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm (based on the above equation) −5° C., followed by a wash of 0.2×SSC/0.1% SDS at 60° C. Moderately stringent hybridization conditions include a washing step in 3×SSC at 42° C. It is understood however that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1.-6.3.6 and in: Sambrook et al., Molecular Cloning, a Laboratory Manual, Cold Spring Harbor Laboratory Press, 1989, Vol. 3.

The term "functional variant", as used herein in reference to polynucleotides or polypeptides, refers to polynucleotides or polypeptides capable of performing the same function as a noted reference polynucleotide or polypeptide. Thus, for example, a functional variant of the polypeptide set forth in SEQ.ID NO: 2, refers to a polypeptide capable of performing the same function as the polypeptide set forth in SEQ.ID NO: 2. Functional variants include modified a polypeptide wherein, relative to a noted reference polypeptide, the modification includes a substitution, deletion or addition of one or more amino acids. In some embodiments, substitutions are those that result in a replacement of one amino acid with an amino acid having similar characteristics. Such substitutions include, without limitation (i) glutamic acid and aspartic acid; (i) alanine, serine, and threonine; (iii) isoleucine, leucine and valine, (iv) asparagine and glutamine, and (v) tryptophan, tyrosine and phenylalanine. Functional variants further include polypeptides having retained or exhibiting an enhanced psilocybin biosynthetic bioactivity.

The term "chimeric", as used herein in the context of nucleic acids, refers to at least two linked nucleic acids which are not naturally linked. Chimeric nucleic acids include linked nucleic acids of different natural origins. For example, a nucleic acid constituting a microbial promoter linked to a nucleic acid encoding a plant polypeptide is considered chimeric. Chimeric nucleic acids also may comprise nucleic acids of the same natural origin, provided they are not naturally linked. For example a nucleic acid constituting a promoter obtained from a particular cell-type may be linked to a nucleic acid encoding a polypeptide obtained from that same cell-type, but not normally linked to the nucleic acid constituting the promoter. Chimeric nucleic acids also include nucleic acids comprising any naturally occurring nucleic acids linked to any non-naturally occurring nucleic acids.

The terms "substantially pure" and "isolated", as may be used interchangeably herein describe a compound, e.g., a psilocybin derivative, polynucleotide or a polypeptide, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis.

The term "recovered" as used herein in association with an enzyme, protein, a chemical compound, refers to a more or less pure form of the enzyme, protein, or chemical compound.

General Implementation

As hereinbefore mentioned, the present disclosure relates to psilocybin derivatives. In particular, the present disclosure provides novel glycosylated psilocybin derivatives. In general, the herein provided compositions exhibit functional properties which deviate from the functional properties of psilocybin. Thus, for example, the glycosylated psilocybin derivatives, can exhibit pharmacological properties which deviate from psilocybin. Furthermore, the glycosylated derivatives may psilocybin derivatives may exhibit physicochemical properties which differ from psilocybin. Thus, for example, glycosylated psilocybin derivatives may exhibit superior solubility in a solvent, for example, an aqueous solvent. The glycosylated psilocybin derivatives in this respect are useful in the formulation of pharmaceutical and recreational drug formulations. Furthermore, the glycosylated psilocybin compounds of the present disclosure may be used as a feedstock material for deriving further psilocybin derivatives. In one embodiment, the glycosylated psilocybin derivatives of the present disclosure can conveniently be biosynthetically produced. The practice of this method avoids the extraction of psilocybin from mushrooms and the performance of subsequent chemical reactions to achieve glycosylated derivatives. Furthermore, the growth of mushrooms can be avoided thus limiting the dependence on climate and weather, and potential legal and social challenges associated with the cultivation of mushrooms containing psychoactive compounds. The method can efficiently yield substantial quantities of glycosylated psilocybin derivatives.

In what follows selected embodiments are described with reference to the drawings.

Initially example glycosylated psilocybin derivatives will be described. Thereafter example methods of using and making the glycosylated psilocybin derivatives will be described.

Accordingly, in one aspect the present disclosure provides derivatives of a compound known as psilocybin of which the chemical structure is shown in FIG. 1. The derivatives herein provided are, in particular, derivatives of psilocybin including a glycosyl group.

Thus, in one aspect, the present disclosure provides, in accordance with the teachings herein, in at least one embodiment, a chemical compound or salt thereof having formula (I):

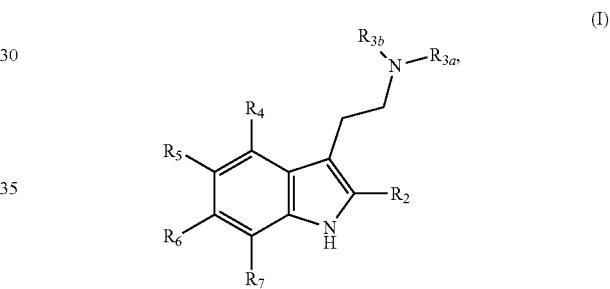

wherein at least one of $R_2$, $R_4$, $R_5$, $R_6$, or $R_7$ is a glycosyl group, and wherein each non-glycosylated $R_2$, $R_5$, $R_6$, or $R_7$ is a hydrogen atom or an alkyl group or O-alkyl group, wherein $R_4$ when it is not glycosylated is a hydrogen atom, an alkyl group or O-alkyl group or a phosphate group, and wherein $R_{3A}$ and $R_{3B}$ are a hydrogen, an alkyl group, an aryl group or an acyl group.

Thus, referring to the chemical compound having formula (I), initially it is noted that, in an aspect thereof, at least one of $R_2$, $R_4$, $R_5$, $R_6$, or $R_7$ is a glycosyl group.

Continuing to refer to the chemical compound having formula (I), the glycosyl groups, in accordance with the present disclosure, can be any glycosyl group, including a mono-, di-, tri- oligo- or a poly-saccharide group, bonded from the anomeric carbon, either in the pyranose or furanose form, either in the α- or the β-conformation, or bonded from a non-anomeric carbon atom in either the furanose or pyranose form.

Furthermore, continuing to the chemical compound having formula (I), the glycosyl groups in accordance herewith may be glycosyloxy groups (O-linked glycosyl groups) or C-linked glycosyl groups.

Continuing to refer to the chemical compound having formula (I), in some embodiments, the glycosyl group may be a D-glucosyl group, D-fructosyl group, D-mannosyl group, D-ribosyl group, D-talosyl group, D-lyxosyl group, D-allosyl group, D-altrosyl group, D-gulosyl group, D-idosyl group, N-acetyl-D-glucosaminyl group, N-acetyl-D-galactosaminyl group, D-quinovosyl group, D-maltosyl group, D-cellobiosyl group, D-lactosyl group, N-acetyl-D-lactosaminyl group, D-maltotiosyl group, D-glucuronic acid group, D-galactosyl group, D-mannosyl group, D-fucosyl group, D-xylosyl group, D-arabinosyl group, a D-rhamnosyl group, a D-glucosaminyl group, or a D-galactosaminyl group.

Continuing to refer to the chemical compound having formula (I), embodiments, the glycosyl group may be an L-glucosyl group, L-fructosyl group, L-mannosyl group, L-ribosyl group, L-talosyl group, L-lyxosyl group, L-allosyl group, L-altrosyl group, L-gulosyl group, L-idosyl group, N-acetyl-L-glucosaminyl group, N-acetyl-L-galactosaminyl group, L-quinovosyl group, L-maltosyl group, L-cellobiosyl group, L-lactosyl group, N-acetyl-L-lactosaminyl group, L-maltotiosyl group, L-glucuronic acid group, L-galactosyl group, L-mannosyl group, L-fucosyl group, L-xylosyl group, L-arabinosyl group, a L-rhamnosyl group, a L-glucosaminyl group, or a L-galactosaminyl group.

Continuing to refer to the chemical compound having formula (I), some embodiments, the glycosyl group may be a glycosyloxy group (i.e., a glycosyl group formed by bonding of the saccharide through its anomeric carbon atom). Thus, as will be clear, in some embodiments, the glycosyl group can be a glycosyloxy group selected from a glucosyloxy group, fructosyloxy group, mannosyoxy group, ribosyloxy group, talosyloxy group, lyxosyloxy group, allosyloxy group, altrosyloxy group, gulosyloxy group, idosyloxy group, N-acetyl-glucosaminyloxy group, N-acetyl-galactosaminyloxy group, quinovosyloxy group, maltosyloxy group, cellobiosyloxy group, lactosyloxy group, N-acetyllactosaminoxy group, maltotiosyloxy group, glucuronicoxy add group, galactosyloxy group, mannosyloxy group fucosyloxy group, xylosyloxy group, arabinosyloxy group, a rhamnosyloxy group, a glucosaminoxy group, or a galactosaminoxy group.

In some embodiments, the glycosyl group may also be substituted with various groups. Such substitutions may include lower alkyl, lower alkoxy, acyl, carboxy, carboxyamino, amino, acetamido, halo, thio, nitro, keto, and phosphatyl groups. Such substitutions may be at one or more positions on the saccharide.

Figure 4A:
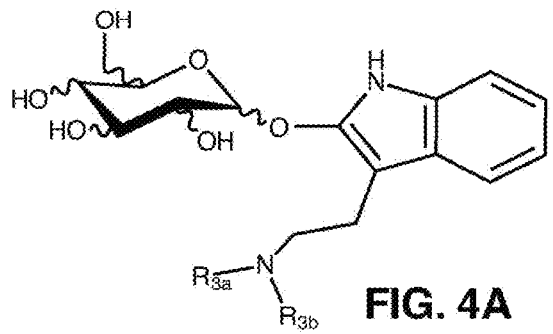
FIGS. 4A, 4B, 4C, 4D, 4E, 4F, 4G, 4H, and 4I depict the chemical structures of certain example glycosylated psilocybin derivative compounds, notably a 2-glycosyloxy psilocybin derivative (FIG. 4A); a 4-glycosyloxy psilocybin derivative (FIG. 4B); a 4-O-ethyl-5-glycosyloxy psilocybin derivative (FIG. 4C); a 6-glycosyloxy psilocybin derivative (FIG. 4D); a 7-glycosyloxy psilocybin derivative (FIG. 4E); a 2-glycosyloxy-4-phospho psilocybin derivative (FIG. 4F); a 4-phospho-5-glycosyloxy psilocybin derivative (FIG. 4G); a 4-phospho-6-glycosyloxy psilocybin derivative (FIG. 4H); and a 4-phospho-7-glycosyloxy psilocybin derivative (FIG. 4I). It is noted that in each of FIGS. 4A, 4B, 4C, 4D, 4E, 4F, 4G, 4H, and 4I $R_{3a}$ and $R_{3b}$ can be a hydrogen atom, an alkyl group, an aryl group, or an acyl group.

Continuing to refer to the chemical compound having formula (I), in one embodiment, one of $R_2$, $R_4$, $R_5$, $R_6$ and $R_7$ can be a glycosyloxy group. Thus, in one embodiment, $R_2$ can be a glycosyloxy group, each of $R_5$, $R_6$ and $R_7$ can be a hydrogen atom or an alkyl group or O-alkyl group, and $R_4$ can be a phosphate group, a hydrogen atom or an alkyl group or O-alkyl group (see: the example glycosylated psilocybin derivatives shown in FIG. 4A ($R_2$ is a glycosyloxy group; $R_4$ is a hydrogen atom; $R_5$, $R_6$ and $R_7$ are a hydrogen atom; $R_{3a}$ and $R_{3b}$ are a hydrogen atom, an alkyl group, an aryl group, or an acyl group) and FIG. 4F ($R_2$ is a glycosyloxy group; $R_4$ is a phosphate group; $R_5$, $R_6$ and $R_7$ are a hydrogen atom; $R_{3a}$ and $R_{3b}$ are a hydrogen atom, an alkyl group, an aryl group, or an acyl group)).

Figure 4B:
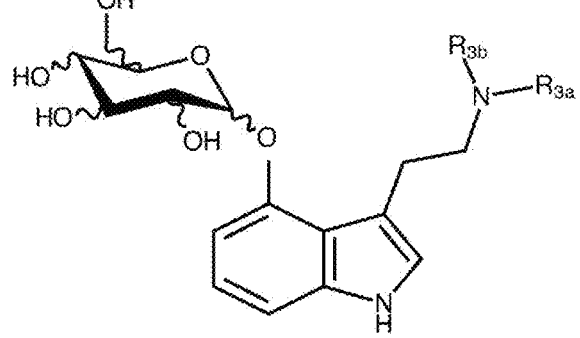

Continuing to refer to the chemical compound having formula (I), in one embodiment, $R_4$ can be a glycosyloxy group, and each of $R_2$, $R_5$, $R_6$ and $R_7$ can be a hydrogen atom or an alkyl group or O-alkyl group (see: the example glycosylated psilocybin derivatives shown in FIG. 4B (Ra is a glycosyloxy group; $R_2$, $R_5$, $R_6$ and $R_7$ are a hydrogen atom; $R_{3a}$ and $R_{3b}$ are a hydrogen atom, an alkyl group, an aryl group, or an acyl group)).

Figure 4C:
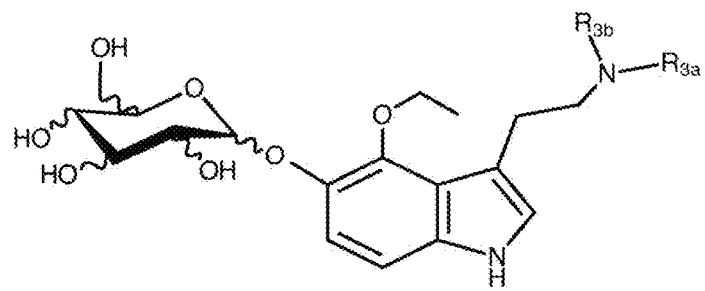

Continuing to refer to the chemical compound having formula (I), in one embodiment, $R_5$ can be a glycosyloxy group, and each of $R_2$, $R_6$ and $R_7$ can be a hydrogen atom or an alkyl group or O-alkyl group, and $R_4$ can be a phosphate group, a hydrogen atom or an alkyl group or O-alkyl group (see: the example glycosylated psilocybin derivatives shown in FIG. 4C ($R_5$ is a glycosyloxy group; $R_4$ is an O-ethyl group; $R_2$, $R_6$ and $R_7$ are a hydrogen atom; $R_{3a}$ and $R_{3b}$ are a hydrogen atom, an alkyl group, an aryl group, or an acyl group) and FIG. 4G ($R_5$ is a glycosyloxy group; $R_4$ is a phosphate group; $R_4$, $R_6$ and $R_7$ are a hydrogen atom; $R_{3a}$ and $R_{3b}$ are a hydrogen atom, an alkyl group, an aryl group, or an acyl group)).

Figure 4D:
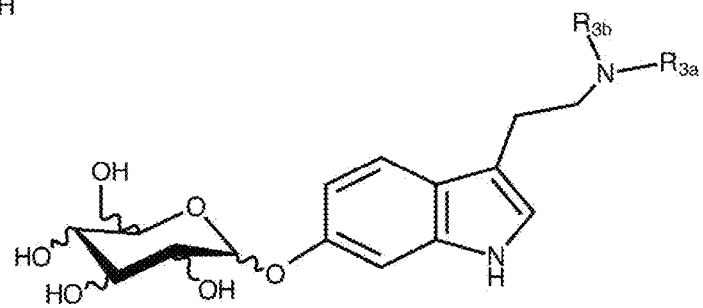

Continuing to refer to the chemical compound having formula (I), in one embodiment, $R_6$ can be a glycosyloxy group, and each of $R_2$, $R_5$ and $R_7$ can be a hydrogen atom or an alkyl group or O-alkyl group, and $R_4$ can be a phosphate group, a hydrogen atom or an alkyl group or O-alkyl group (see: the example glycosylated psilocybin derivatives shown in FIG. 4D ($R_6$ is a glycosyloxy group; $R_4$ is a phosphate group; $R_2$, $R_5$ and $R_7$ are a hydrogen atom; $R_{3a}$ and $R_{3b}$ are a hydrogen atom, an alkyl group, an aryl group, or an acyl group) and FIG. 4H ($R_6$ is a glycosyloxy group; $R_4$ is a phosphate group; $R_2$, $R_5$ and $R_7$ are a hydrogen atom; $R_{3a}$ and $R_{3b}$ are a hydrogen atom, an alkyl group, an aryl group, or an acyl group)).

Figure 4E:
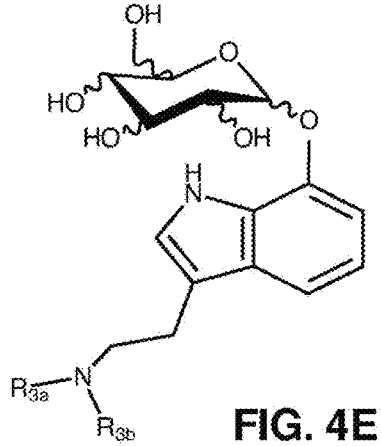
Figure 4F:
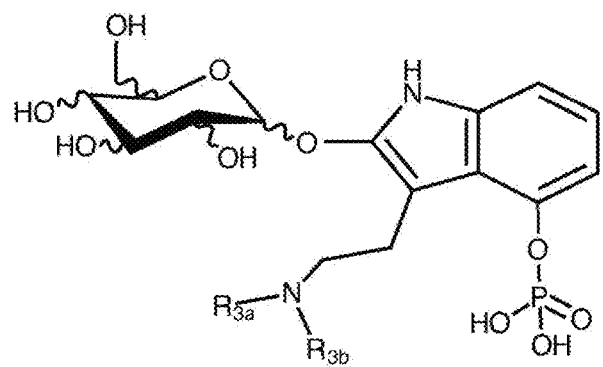
Figure 4G:
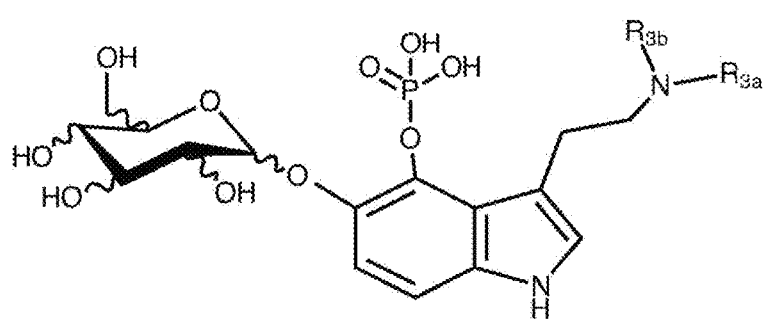
Figure 4H:
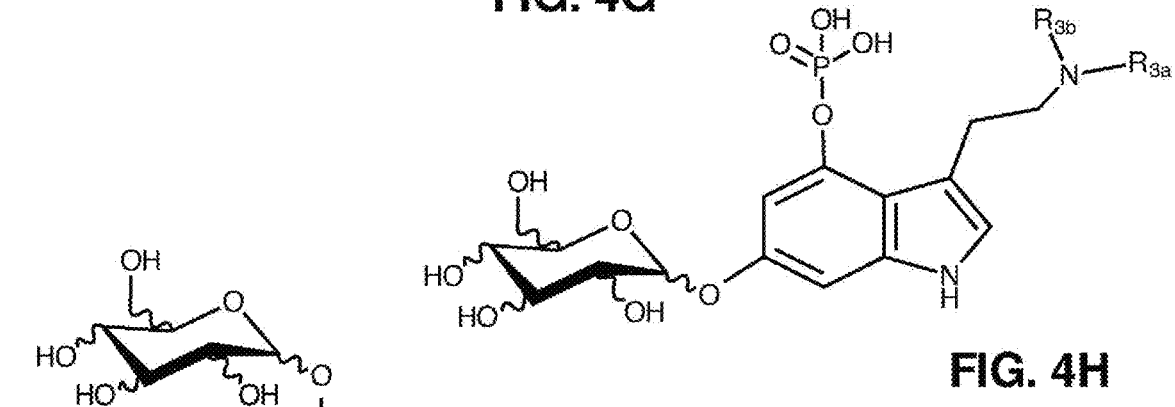
Figure 4I:
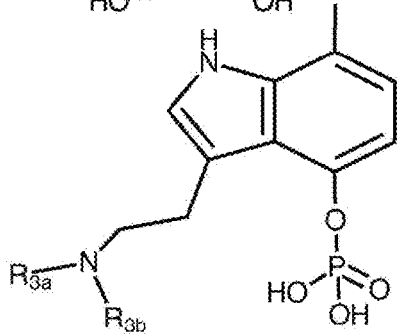

Continuing to refer to the chemical compound having formula (I), in one embodiment, $R_7$ can be a glycosyloxy group, and each of $R_2$, $R_5$ and $R_6$ can be a hydrogen atom or an alkyl group or O-alkyl group, and $R_4$ can be a phosphate group, a hydrogen atom or an alkyl group or O-alkyl group (see: the example glycosylated psilocybin derivatives shown in FIG. 4E ($R_7$ is a glycosyloxy group; $R_4$ is a hydrogen atom; $R_2$, $R_5$ and $R_6$ are a hydrogen atom $R_{3a}$ and $R_{3b}$ are a hydrogen atom, an alkyl group, an aryl group, or an acyl group) and FIG. 4I ($R_7$ is a glycosyloxy group; $R_4$ is a phosphate group; $R_2$, $R_5$ and $R_6$ are a hydrogen atom; $R_{3a}$ and $R_{3b}$ are a hydrogen atom, an alkyl group, an aryl group, or an acyl group)).

As noted previously noted, the glycosyl groups may be C-linked or O-linked. Examples of compounds comprising O-linked glycosyl groups in accordance herewith are hereinbefore described with reference to FIGS. 4A-4I. Examples of compounds comprising C-linked glycosyl groups in accordance herewith are next described with reference to FIGS. 5A-5I.

Still continuing to refer to the chemical compound having formula (I), in one embodiment, one of $R_2$, $R_4$, $R_5$, $R_6$ and $R_7$ can be a C-linked glycosyl group. Thus, in one embodiment, $R_2$ can be a C-linked glycosyl group, each of $R_5$, $R_6$ and $R_7$ can be a hydrogen atom or an alkyl group or O-alkyl group, and $R_4$ can be a phosphate group, a hydrogen atom or an alkyl group or O-alkyl group (see: the example glycosylated psilocybin derivatives shown in FIG. 5A ($R_2$ is a C-linked glycosyl group; $R_4$ is a hydrogen atom; $R_5$, $R_6$ and $R_7$ are a hydrogen atom; $R_{3a}$ and $R_{3b}$ are a hydrogen atom, an alkyl group, an aryl group, or an acyl group) and FIG. 5F ($R_2$ is a C-linked glycosyl group; $R_4$ is a phosphate group; $R_5$, $R_6$ and $R_7$ are a hydrogen atom; $R_{3a}$ and $R_{3b}$ are a hydrogen atom, an alkyl group, an aryl group, or an acyl group)).

Figure 5A:
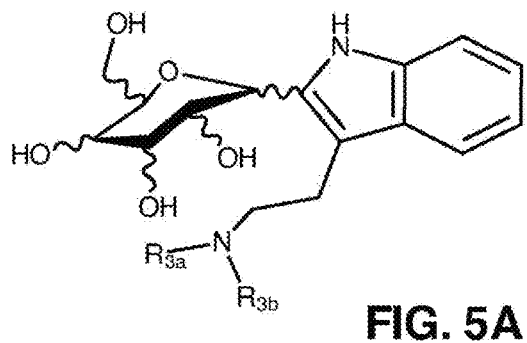
FIGS. 5A, 5B, 5C, 5D, 5E, 5F, 5G, 5H, and 5I depict the chemical structures of certain further example glycosylated psilocybin derivative compounds, notably a 2-C-glycosyl psilocybin derivative (FIG. 5A); a 4-C-glycosyl psilocybin derivative (FIG. 5B); a 5-C-glycosyl-6-O-methyl-7-methyl psilocybin derivative (FIG. 5C); a 6-C-glycosyl psilocybin derivative (FIG. 5D); a 7-C-glycosyl psilocybin derivative (FIG. 5E); a 2-C-glycosyl-4-phospho psilocybin derivative (FIG. 5F); a 4-phospho-5-C-glycosyl psilocybin derivative (FIG. 5G); a 4-phospho-5-ethyl-6-C-glycosyl psilocybin derivative (FIG. 5H); and a 4-phospho-7-C-glycosyl psilocybin derivative (FIG. 5I). It is noted that in each of FIGS. 5A, 5B, 5C, 5D, 5E, 5F, 5G, 5H, and 5I $R_{3a}$ and $R_{3b}$ can be a hydrogen atom, an alkyl group, an aryl group, or an acyl group.
Figure 5B:
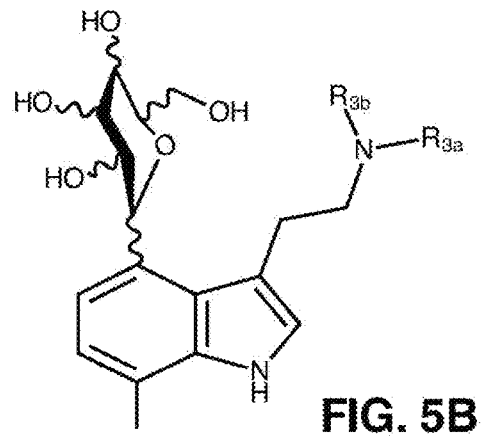

Continuing to refer to the chemical compound having formula (I), in one embodiment, $R_4$ can be a C-linked glycosyl group, and each of $R_2$, $R_5$, $R_6$ and $R_7$ can be a hydrogen atom (see: the example glycosylated psilocybin derivatives shown in FIG. 5B ($R_4$ is a C-linked glycosyl group; $R_2$, $R_5$, and $R_6$ are a hydrogen atom $R_7$ is a methyl group; $R_{3a}$ and $R_{3b}$ are a hydrogen atom, an alkyl group, an aryl group, or an acyl group)).

Figure 5C:
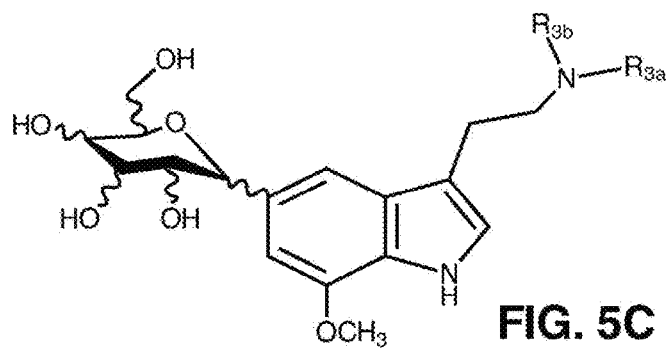

Continuing to refer to the chemical compound having formula (I), in one embodiment, $R_5$ can be a C-linked glycosyl group, and each of $R_2$, $R_6$ and $R_7$ can be a hydrogen atom or an alkyl group or O-alkyl group, and $R_4$ can be a phosphate group, a hydrogen atom or an alkyl group or O-alkyl group (see: the example glycosylated psilocybin derivatives shown in FIG. 5C ($R_5$ is a C-linked glycosyl group; $R_4$ is a hydrogen atom; $R_2$, and $R_7$ are a hydrogen atom; $R_6$ is an O-methyl group, $R_{3a}$ and $R_{3b}$ are a hydrogen atom, an, an aryl group, or an acyl group) and FIG. 5G ($R_5$ is a C-linked glycosyl group; $R_4$ is a phosphate group; $R_4$, $R_6$ and $R_7$ are a hydrogen atom; $R_{3a}$ and $R_{3b}$ are a hydrogen atom, an alkyl group, an aryl group, or an acyl group)).

Figure 5D:
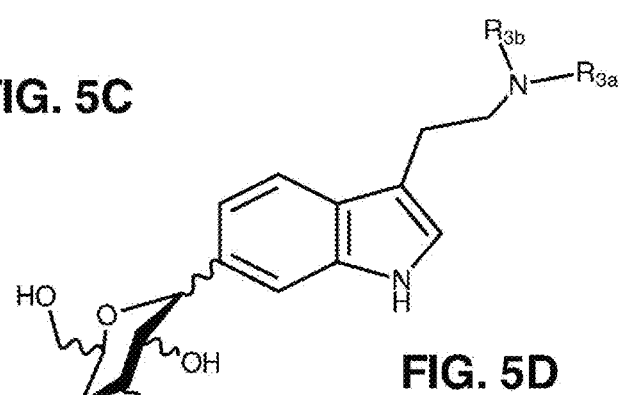

Continuing to refer to the chemical compound having formula (I), in one embodiment, $R_6$ can be a C-linked glycosyl group, and each of $R_2$, $R_5$ and $R_7$ can be a hydrogen atom or an alkyl group or O-alkyl group, and $R_4$ can be a phosphate group, a hydrogen atom or an alkyl group or O-alkyl group (see: the example glycosylated psilocybin derivatives shown in FIG. 5D ($R_6$ is a C-linked glycosyl group; $R_4$ is a phosphate group; $R_2$, $R_5$ and $R_7$ are a hydrogen atom; $R_{3a}$ and $R_{3b}$ are a hydrogen atom, an alkyl group, an aryl group, or an acyl group) and FIG. 5H ($R_6$ is a C-linked glycosyl group; $R_4$ is a phosphate group; $R_2$, and $R_7$ are a hydrogen atom; $R_5$ is an ethyl group; $R_{3a}$ and $R_{3b}$ are a hydrogen atom, an alkyl group, an aryl group, or an acyl group)).

Figure 5E:
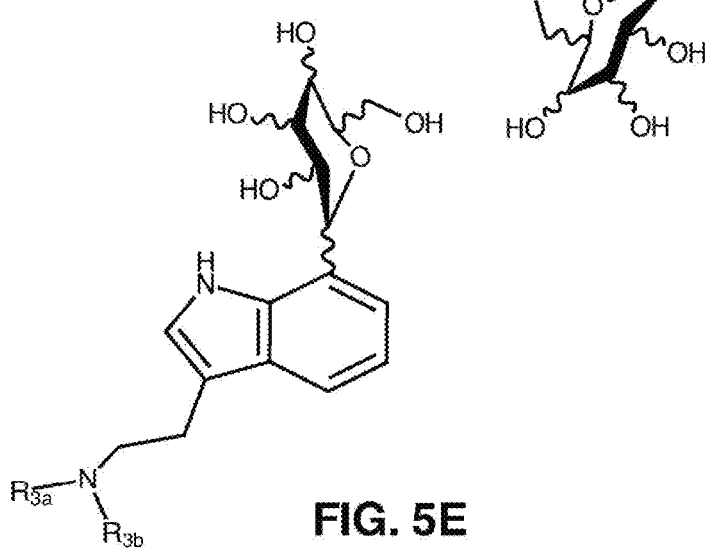
Figure 5F:
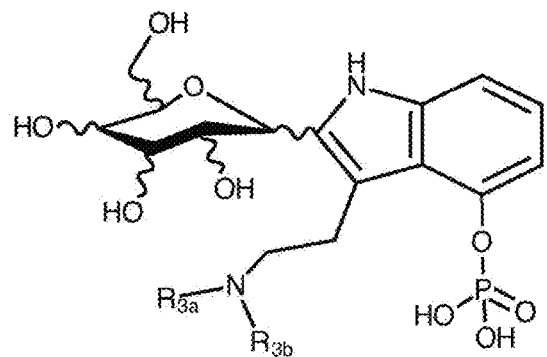
Figure 5G:
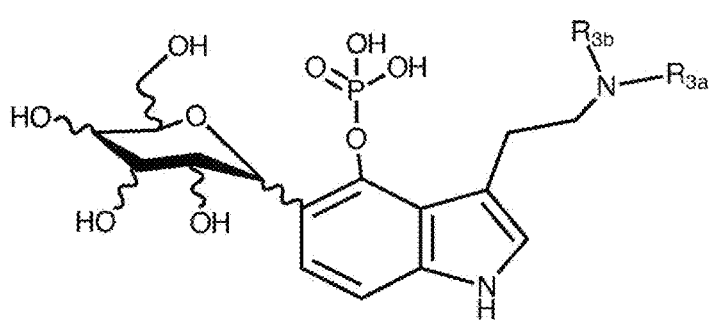
Figure 5H:
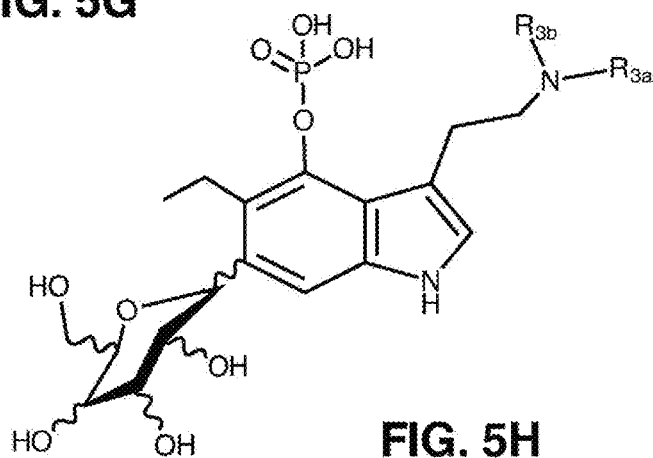
Figure 5I:
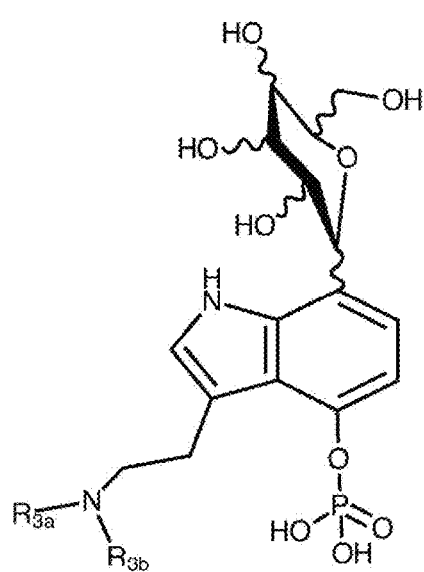

Continuing to refer to the chemical compound having formula (I), in one embodiment, $R_7$ can be a C-linked glycosyl group, and each of $R_2$, $R_5$ and $R_6$ can be a hydrogen atom or an alkyl group or O-alkyl group, and $R_4$ can be a phosphate group, a hydrogen atom or an alkyl group or O-alkyl group (see: the example glycosylated psilocybin derivatives shown in FIG. 5E ($R_7$ is a C-linked glycosyl group; $R_4$ is a hydrogen atom; $R_2$, $R_5$ and $R_6$ are a hydrogen atom $R_{3a}$ and $R_{3b}$ are a hydrogen atom, an alkyl group, an aryl group, or an acyl group) and FIG. 5I ($R_7$ is a C-linked glycosyl group; $R_4$ is a phosphate group; $R_2$, $R_5$ and $R_6$ are a hydrogen atom; $R_{3a}$ and $R_{3b}$ are a hydrogen atom, an alkyl group, an aryl group, or an acyl group)).

In some embodiments, two of $R_2$, $R_4$, $R_5$, $R_6$ and $R_7$ of the chemical compound having formula (I) can be glycosyl groups. Thus, continuing to refer to the chemical compound having formula (I), in one embodiment, two of $R_2$, $R_4$, $R_5$, $R_6$ and $R_7$ can be a glycosyl group, wherein each non-glycosylated $R_2$, $R_5$, $R_6$ and $R_7$ is a hydrogen atom or an alkyl group or O-alkyl group, and wherein $R_4$, when it is not a glycosyl group, is a phosphate group, a hydrogen atom, or an alkyl group or O-alkyl group.

Figure 6A:
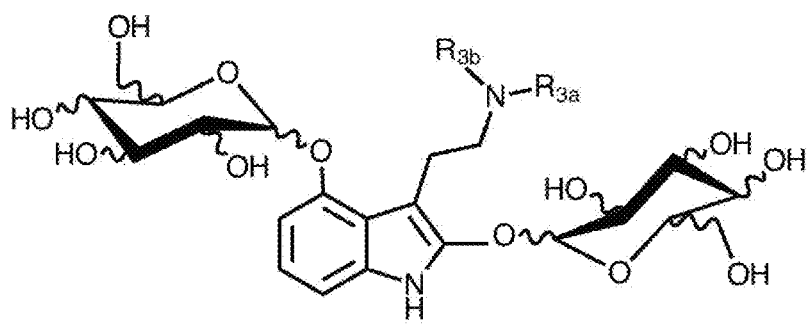
FIGS. 6A, 6B, 6C, 6D, 6E, 6F, 6G, 6H, 6I and 6J depict the chemical structures of certain further example glycosylated psilocybin derivative compounds, notably a 2,4-di-glycosyloxy psilocybin derivative (FIG. 6A); a 2-C-glycosyl-5-glycosyloxy psilocybin derivative (FIG. 6B); a 2-C-glycosyl-4-methyl-6-glycosyloxy psilocybin derivative (FIG. 6C); a 2-glycosyloxy-4-phospho-7-C-glycosyl psilocybin derivative (FIG. 6D); a 4,5-di-glycosyloxy psilocybin derivative (FIG. 6E); a 4,6-di-C-glycosyl psilocybin derivative (FIG. 6F); a 4-glycosyloxy-7-C-glycosyl psilocybin derivative (FIG. 6G); a 4-phospho-5-glycosyloxy-6-C-glycosyl psilocybin derivative (FIG. 6H) a 4-phospho-5,7-di-glycosyloxy psilocybin derivative (FIG. 6I); and a 6,7-di-glycosyloxy psilocybin derivative (FIG. 6J). It is noted that in each of FIGS. 6A, 6B, 6C, 6D, 6E, 6F, 6G, 6H, 6I and 6J $R_{3a}$ and $R_{3b}$ can be a hydrogen atom, an alkyl group, an aryl group, or an acyl group.

Still continuing to refer to the chemical compound having formula (I), in one embodiment, $R_2$ and $R_4$ can be glycosyl groups, wherein the glycosyl groups are independently selected from a glycosyloxy group or a C-linked glycosyl group, and $R_5$, $R_6$ and $R_7$ can be independently selected from a hydrogen atom or an alkyl group or O-alkyl group (see: the example glycosylated psilocybin derivative shown in FIG. 6A ($R_2$ and $R_4$ are each a glycosyloxy group; $R_5$, $R_6$ and $R_7$ are hydrogen atoms; and $R_{3a}$ and $R_{3b}$ are a hydrogen atom, an alkyl group, an aryl group, or an acyl group)).

Figure 6B:
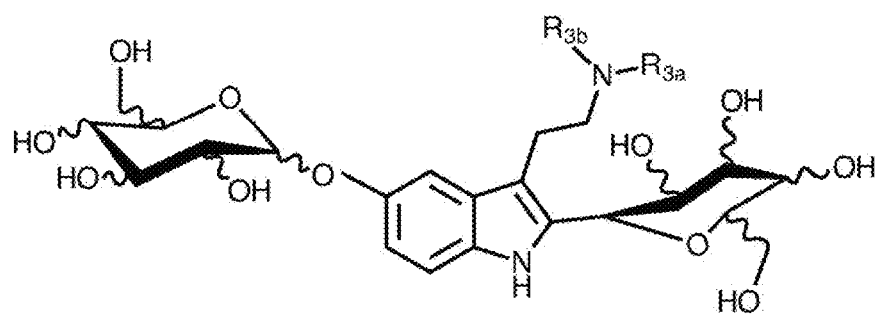

Continuing to refer to the chemical compound having formula (I), in one embodiment, $R_2$ and $R_5$ can be glycosyl groups wherein the glycosyl groups are independently selected from a glycosyloxy group or a C-linked glycosyl group, and $R_6$ and $R_7$ can be independently selected from a hydrogen atom or an alkyl group or O-alkyl group and $R_4$ can be a phosphate group, a hydrogen atom or an alkyl group or O-alkyl group (see: the example glycosylated psilocybin derivative shown in FIG. 6B ($R_2$ is a C-linked glycosyl group; $R_5$ is a glycosyloxy group; $R_4$, $R_6$ and $R_7$ are hydrogen atoms; and $R_{3a}$ and $R_{3b}$ are a hydrogen atom, an alkyl group, an aryl group, or an acyl group)).

Figure 6C:
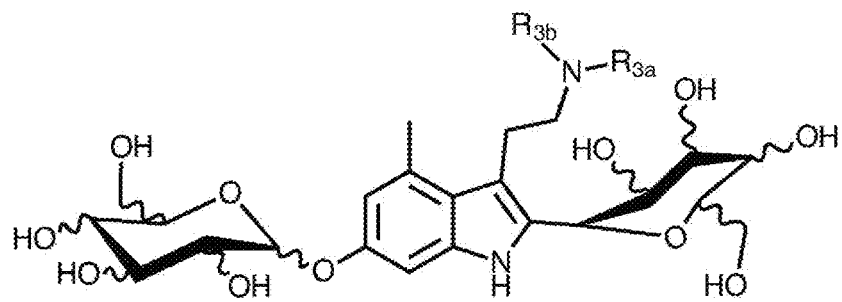

Continuing to refer to the chemical compound having formula (I), in one embodiment, $R_2$ and $R_6$ can be glycosyl groups, wherein the glycosyl groups are independently selected from a glycosyloxy group or a C-linked glycosyl group, and $R_5$ and $R_7$ can be independently selected from a hydrogen atom or an alkyl group or O-alkyl group, and $R_4$ can be a phosphate group, a hydrogen atom or an alkyl group or O-alkyl group (see: the example glycosylated psilocybin derivative shown in FIG. 6C ($R_2$ is a C-linked glycosyl group; $R_6$ is a glycosyloxy group; $R_4$ is a methyl group; $R_5$ and $R_7$ are hydrogen atoms; and $R_{3a}$ and $R_{3b}$ are a hydrogen atom, an alkyl group, an aryl group, or an acyl group)).

Figure 6D:
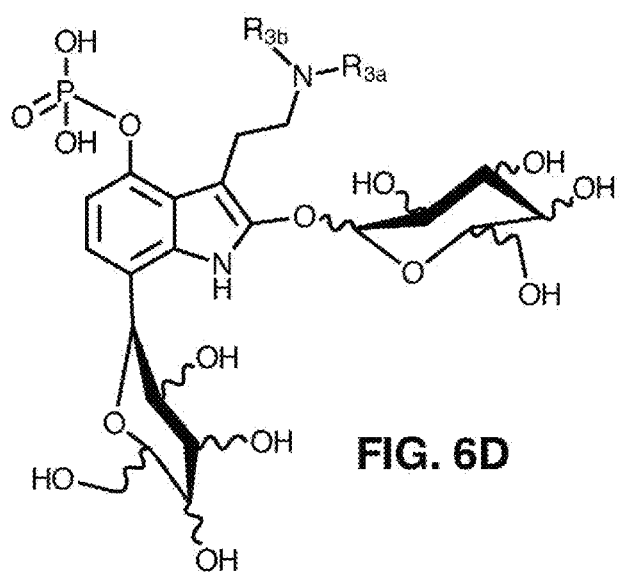

Continuing to refer to the chemical compound having formula (I), in one embodiment, $R_2$ and $R_7$ can be glycosyl groups, wherein the glycosyl groups are independently selected from a glycosyloxy group or a C-linked glycosyl group, and $R_5$ and $R_6$ can be independently selected from a hydrogen atom or an alkyl group or O-alkyl group and $R_4$ can be a phosphate group, a hydrogen atom or alkyl group or O-alkyl group (see: the example glycosylated psilocybin derivative shown in FIG. 6D ($R_2$ is a glycosyloxy group; $R_7$ is a C-linked glycosyl group; $R_4$ is a phosphate group; $R_5$ and $R_6$ are hydrogen atoms; and $R_{3a}$ and $R_{3b}$ are a hydrogen atom, an alkyl group, an aryl group, or an acyl group)).

Figure 6E:
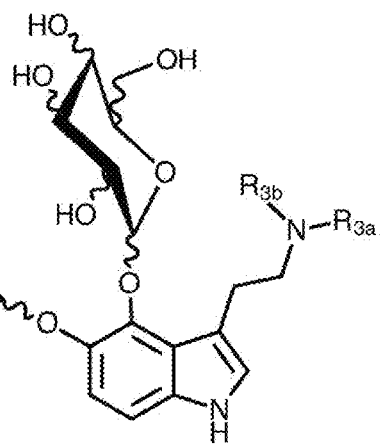

In one embodiment, $R_4$ and $R_5$ can be glycosyl groups, wherein the glycosyl groups are independently selected from a glycosyloxy group or a C-linked glycosyl group, and $R_2$, $R_6$ and $R_7$ can be independently selected from a hydrogen atom or an alkyl group or O-alkyl group (see: the example glycosylated psilocybin derivative shown in FIG. 6E (Ra and $R_5$ are each glycosyloxy groups; $R_2$, $R_6$ and $R_7$ are hydrogen atoms; and $R_{3a}$ and $R_{3b}$ are a hydrogen atom, an alkyl group, an aryl group, or an acyl group)).

Figure 6F:
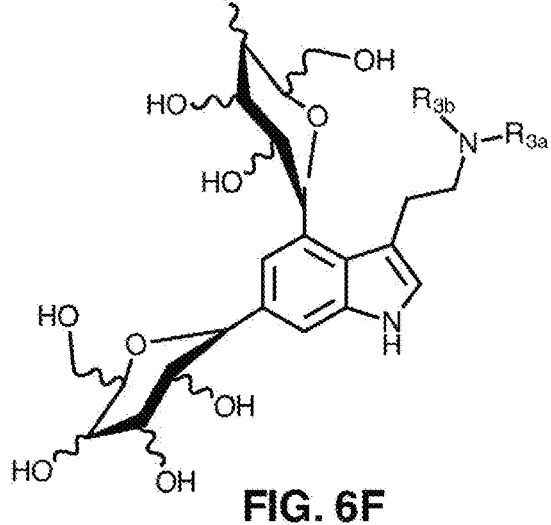

Continuing to refer to the chemical compound having formula (I), in one embodiment, $R_4$ and $R_6$ can be glycosyl groups, wherein the glycosyl groups are independently selected from a glycosyloxy group or a C-linked glycosyl group, and $R_2$, $R_5$ and $R_7$ can be independently selected from a hydrogen atom or an alkyl group or O-alkyl group (see: the example glycosylated psilocybin derivative shown in FIG. 6F (Ra and $R_6$ are each glycosyloxy groups; $R_2$, $R_5$ and $R_7$ are hydrogen atoms; and $R_{3a}$ and $R_{3b}$ are a hydrogen atom, an alkyl group, an aryl group, or an acyl group)).

Figure 6G:
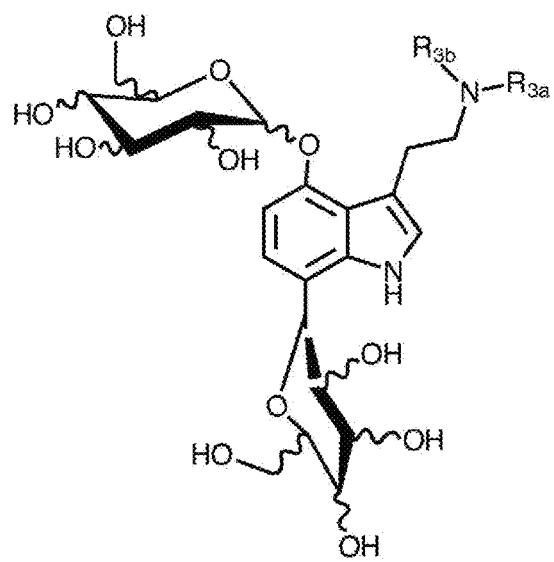

Continuing to refer to the chemical compound having formula (I), in one embodiment, $R_4$ and $R_7$ can be glycosyl groups, wherein the glycosyl groups are independently selected from a glycosyloxy group or a C-linked glycosyl group, and $R_2$, $R_5$ and $R_6$ can be independently selected from a hydrogen atom or an alkyl group or O-alkyl group (see: the example glycosylated psilocybin derivative shown in FIG. 6G (Ra is a glycosyloxy group; $R_7$ is a C-linked glycosyl group; $R_2$, $R_5$ and $R_6$ are hydrogen atoms; and $R_{3a}$ and $R_{3b}$ are a hydrogen atom, an alkyl group, an aryl group, or an acyl group)).

Figure 6H:
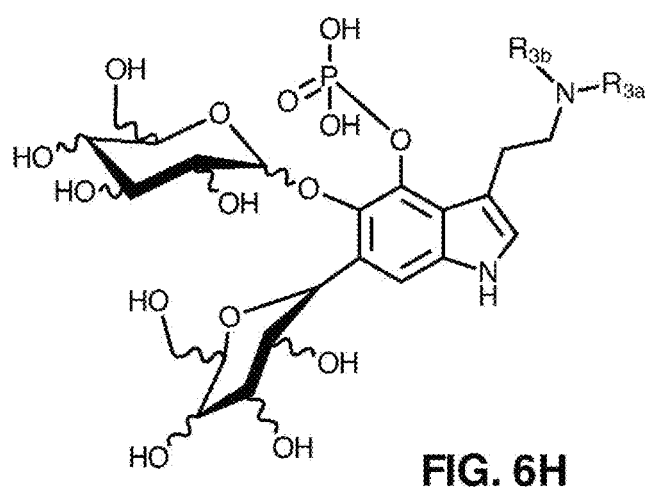

Continuing to refer to the chemical compound having formula (I), in one embodiment, $R_5$ and $R_6$ can be glycosyl groups, wherein the glycosyl groups are independently selected from a glycosyloxy group or a C-linked glycosyl group, and $R_2$ and $R_7$ can be independently selected from a hydrogen atom or an alkyl group or O-alkyl group and $R_4$ can be a phosphate group, a hydrogen atom or an alkyl group or O-alkyl group (see: the example glycosylated psilocybin derivative shown in FIG. 6H ($R_5$ is a glycosyloxy group; $R_6$ is a C-linked glycosyl group; $R_4$ is a phosphate group; $R_2$ and $R_7$ are hydrogen atoms; and $R_{3a}$ and $R_{3b}$ are a hydrogen atom, an alkyl group, an aryl group, or an acyl group)).

Figure 6I:
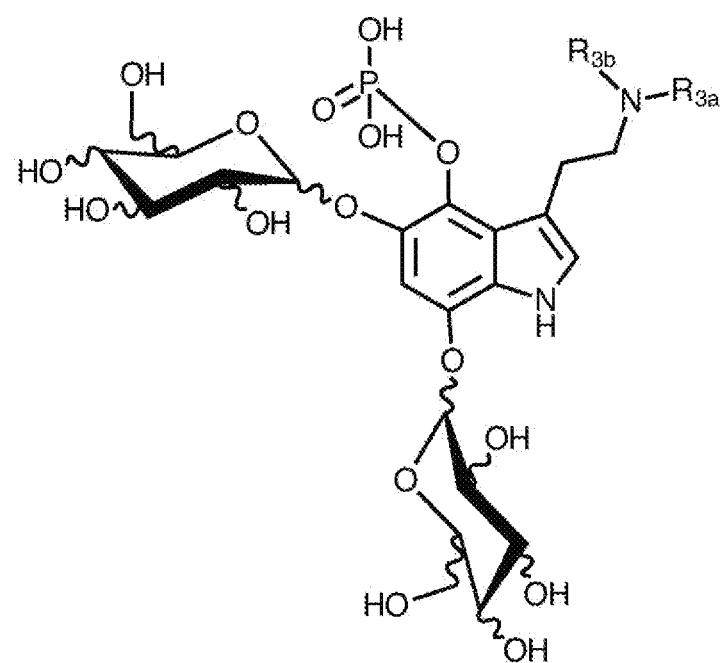

Continuing to refer to the chemical compound having formula (I), in one embodiment, $R_5$ and $R_7$ can be glycosyl groups, wherein the glycosyl groups are independently selected from a glycosyloxy group or a C-linked glycosyl group, and $R_2$ and $R_6$ can be independently selected from a hydrogen atom or an alkyl group or O-alkyl group and $R_4$ can be a phosphate group, a hydrogen atom or an alkyl group or O-alkyl group (see: the example glycosylated psilocybin derivative shown in FIGS. 6I ($R_5$ and $R_7$ are each glycosyloxy groups; $R_4$ is a phosphate group; $R_2$ and $R_6$ are hydrogen atoms; and $R_{3a}$ and $R_{3b}$ are a hydrogen atom, an alkyl group, an aryl group, or an acyl group)).

Figure 6J:
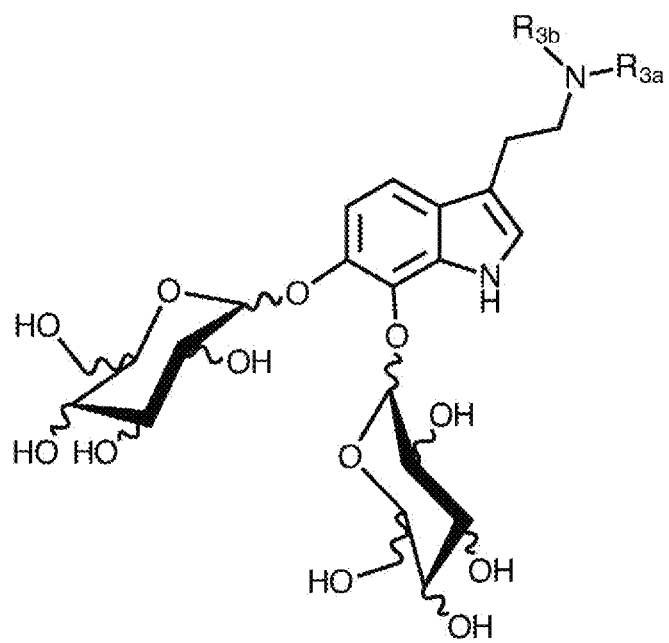

Continuing to refer to the chemical compound having formula (I), in one embodiment, $R_6$ and $R_7$ can be glycosyl groups, wherein the glycosyl are independently selected from a glycosyloxy group or a C-linked glycosyl group, and $R_2$ and $R_5$ can be independently selected from a hydrogen atom or an alkyl group or O-alkyl group and $R_4$ can be a phosphate group, a hydrogen atom or an alkyl group or O-alkyl group (see: the example glycosylated psilocybin derivative shown in FIG. 6J ($R_6$ and $R_7$ are each glycosyloxy groups; $R_2$, $R_4$ and $R_5$ are hydrogen atoms; and $R_{3a}$ and $R_{3b}$ are a hydrogen atom, an alkyl group, an aryl group, or an acyl group)).

It is further noted that in embodiments hereof which include at least two glycosyl groups (as in the example compounds shown in FIGS. 6A-6J), in some embodiments, the glycosyl groups may all be glycosyloxy groups (as in the example compounds shown in FIGS. 6A, 6E, 6I and 6J); in some embodiments, glycosyl groups may all be C-linked glycosyl groups (as in the example compound shown in in FIG. 6F); and in some embodiments, the glycosyl groups may include at least one glycosyloxy group and at least one C-linked glycosyl group (as in the example compounds shown in FIGS. 6B, 6C, 6D, 6G and 6H).

It is further noted that in embodiments hereof which include at least two glycosyl groups, the glycosyl groups in some embodiments may all be identical glycosyl groups (e.g. two glucosyl groups, two galactosyl groups, three galactosyl groups etc.). In other embodiments, the glycosyl groups may be different glycosyl groups (e.g. a glucosyl and a fucosyl group; a fucosyl group and a galactosyl group; a glucosyl group, a fucosyl group and a lactosyl group etc.).

Referring again to the chemical compound having formula (I), in one further embodiment, three of $R_2$, $R_4$, $R_5$, $R_6$ and $R_7$ can be a glycosyl group, wherein the glycosyl groups are independently selected from a glycosyloxy group and C-linked glycosyl group, and wherein the non-glycosylated $R_2$, $R_5$, $R_6$, or $R_7$ substituents are independently selected from a hydrogen atom or an alkyl group or O-alkyl group, and wherein $R_4$, when it is not a glycosyl group, is a phosphate group, a hydrogen atom or an alkyl group or O-alkyl group.

Figure 7A:
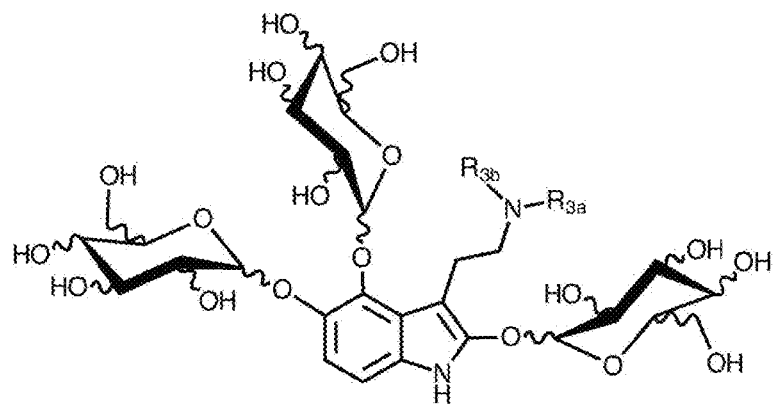
FIGS. 7A, 7B, 7C, 7D, 7E, and 7F depict the chemical structures of certain further example glycosylated psilocybin derivative compounds, notably a 2,4,5-tri-glycosyloxy psilocybin derivative (FIG. 7A); a 2-C-glycosyl-5,6-di-glycosyloxy psilocybin derivative (FIG. 7B); a 2-5-di-glycosyloxy-7-C-glycosyl psilocybin derivative (FIG. 7C); a 4,6-di-C-glycosyl-5-glycosyloxy psilocybin derivative (FIG. 7D); a 4,5,7-tri-glycosyloxy psilocybin derivative (FIG. 7E); and a 4-phospho-5-glycosyloxy-6,7-di-C-glycosyl psilocybin derivative (FIG. 7F). It is noted that in each of FIGS. 7A, 7B, 7C, 7D, 7E, and 7F $R_{3a}$ and $R_{3b}$ can be a hydrogen atom, an alkyl group, an aryl group, or an acyl group.

Thus, referring to the chemical compound having formula (I) again, in one embodiment $R_2$, $R_4$, and $R_5$ can be a glycosyl group, wherein the glycosyl groups are independently selected from a glycosyloxy group and C-linked glycosyl group, and $R_6$ and $R_7$ can be independently selected from a hydrogen atom or an alkyl group or O-alkyl group (see: the example glycosylated psilocybin derivative shown in FIG. 7A ($R_2$, $R_4$ and $R_5$ are each glycosyloxy groups; $R_6$ and $R_7$ are hydrogen atoms; and $R_{3a}$ and $R_{3b}$ are a hydrogen atom, an alkyl group, an aryl group, or an acyl group)).

Figure 7B:
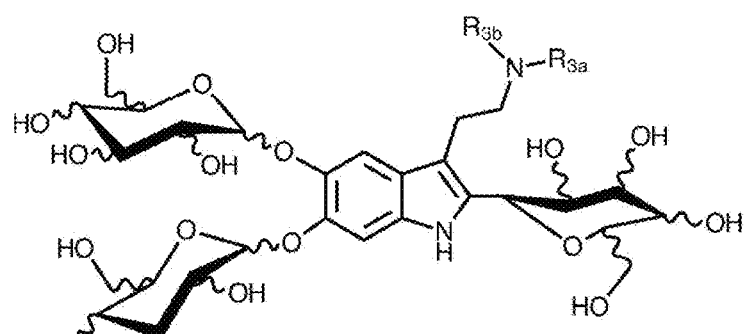

Referring to the chemical compound having formula (I), in one embodiment, $R_2$, $R_5$, and $R_6$ can be a glycosyl group, wherein the glycosyl groups are independently selected from a glycosyloxy group and C-linked glycosyl group, and $R_7$ can be independently selected from a hydrogen atom or an alkyl group or O-alkyl group, and $R_4$ can a phosphate group, a hydrogen atom or an alkyl group or O-alkyl group (see: the example glycosylated psilocybin derivative shown in FIG. 7B ($R_2$ is a C-linked glycosyl group, $R_5$ and $R_6$ are each glycosyloxy groups; $R_4$ and $R_7$ are hydrogen atoms; and $R_{3a}$ and $R_{3b}$ are a hydrogen atom, an alkyl group, an aryl group, or an acyl group)).

Figure 7C:
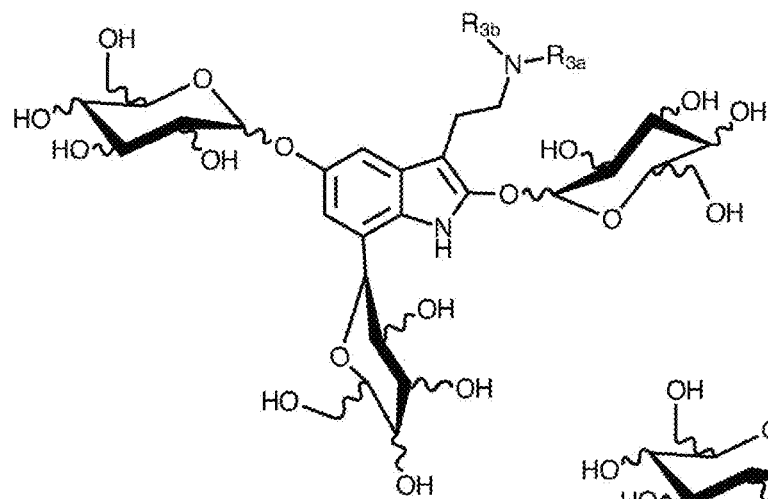

Referring to the chemical compound having formula (I), in one embodiment, $R_2$, $R_5$, and $R_7$ can be a glycosyl group, wherein the glycosyl groups are independently selected from a glycosyloxy group and C-linked glycosyl group, and $R_6$ can be independently selected from a hydrogen atom or an alkyl group or O-alkyl group, and $R_4$ can a phosphate group, a hydrogen atom or alkyl group or O-alkyl group (see: the example glycosylated psilocybin derivative shown in FIG. 7C ($R_2$ and $R_5$ are each glycosyloxy groups and $R_7$ is a C-linked glycosyl group; $R_4$ and $R_6$ are hydrogen atoms; and $R_{3a}$ and $R_{3b}$ are a hydrogen atom, an alkyl group, an aryl group, or an acyl group)).

Figure 7D:
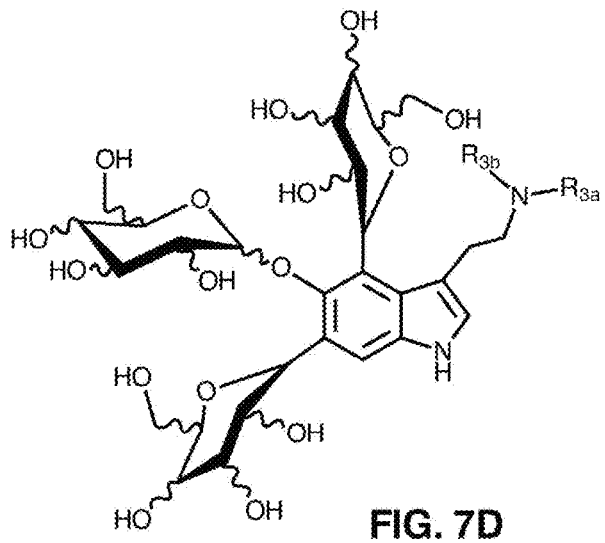

Referring to the chemical compound having formula (I), in one embodiment, $R_4$, $R_5$, and $R_6$ can be a glycosyl group, wherein the glycosyl groups are independently selected from a glycosyloxy group and C-linked glycosyl group, and $R_2$ and $R_7$ can be independently selected from a hydrogen atom or an alkyl group or O-alkyl group (see: the example glycosylated psilocybin derivative shown in FIG. 7D ($R_4$ and $R_6$ are each a C-linked glycosyl group; $R_6$ is a glycosyloxy group; $R_2$ and $R_7$ are hydrogen atoms; and $R_{3a}$ and $R_{3b}$ are a hydrogen atom, an alkyl group, an aryl group, or an acyl group)).

Figure 7E:
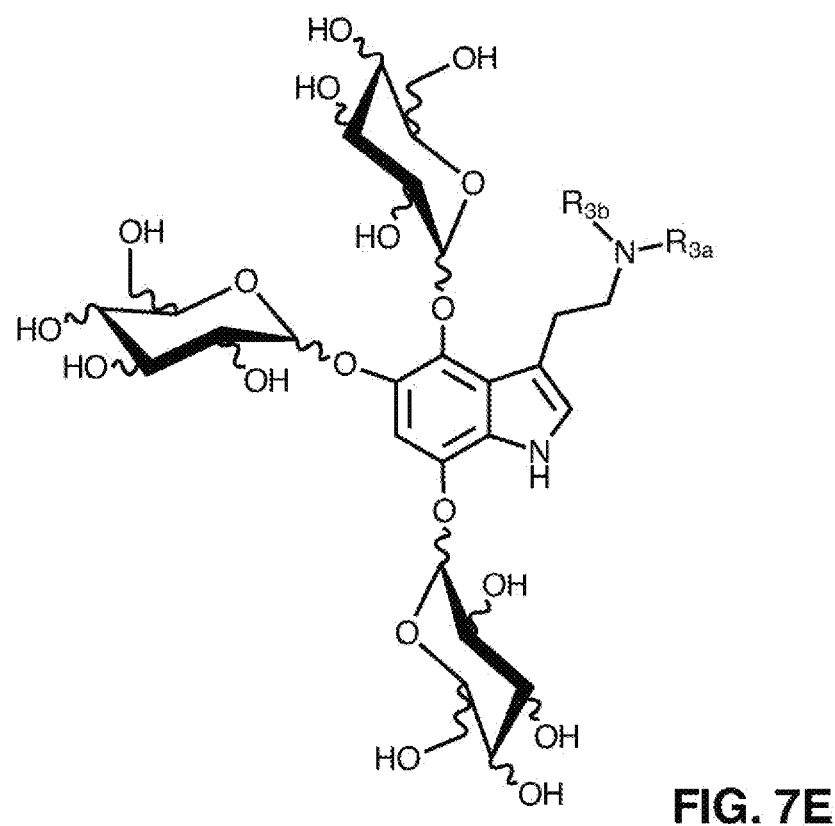

Referring to the chemical compound having formula (I), in one embodiment, $R_4$, $R_5$, and $R_7$ can be a glycosyl group, wherein the glycosyl groups are independently selected from a glycosyloxy group and C-linked glycosyl group, and $R_2$ and $R_6$ can be independently selected from a hydrogen atom or an alkyl group or O-alkyl group (see: the example glycosylated psilocybin derivative shown in FIG. 7E ($R_4$ $R_5$ and $R_7$ are each a glycosyloxy group; $R_2$ and $R_6$ are hydrogen atoms; and $R_{3a}$ and $R_{3b}$ are a hydrogen atom, an alkyl group, an aryl group, or an acyl group)).

Figure 7F:
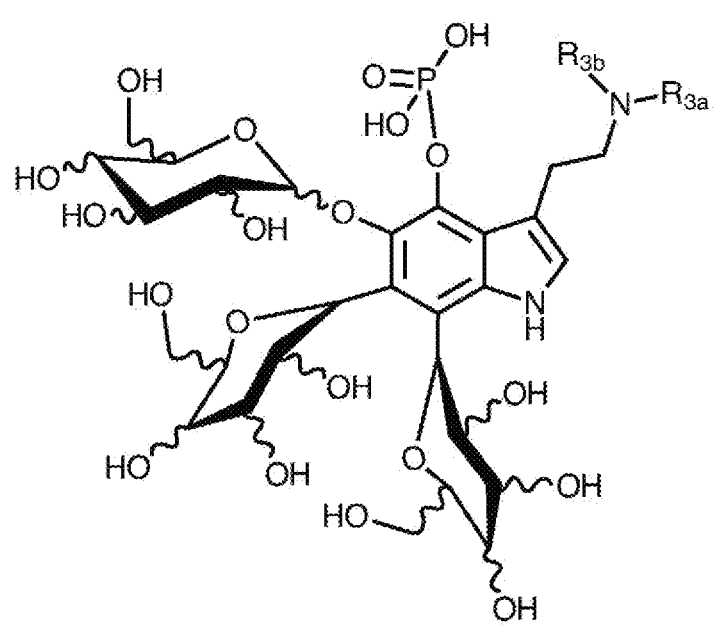

Referring to the chemical compound having formula (I), in one embodiment, $R_5$, $R_6$, and $R_7$ can a glycosyl group, wherein the glycosyl groups are independently selected from a glycosyloxy group and C-linked glycosyl group, and $R_2$ can be a hydrogen atom or an alkyl group or O-alkyl group, and $R_4$ can be a phosphate group, a hydrogen atom or an alkyl group or O-alkyl group (see: the example glycosylated psilocybin derivative shown in FIG. 7F ($R_5$ is a glycosyloxy group, $R_6$ and $R_7$ are each a C-linked glycosyl group; $R_4$ is a phosphate group; $R_2$ is a hydrogen atom; and $R_{3a}$ and $R_{3b}$ are a hydrogen atom, an alkyl group, an aryl group, or an acyl group)).

Referring to the chemical compound having formula (I), in one embodiment, three of $R_2$, $R_4$, $R_5$, $R_6$ and $R_7$ can be a glycosyloxy group, the remaining $R_2$, $R_5$, $R_6$, and $R_7$ being hydrogen atoms or alkyl group or O-alkyl groups, and $R_4$ when it is not a glycosyloxy group, being a phosphate group, a hydrogen atom or an alkyl group or O-alkyl group (see: e.g. the psilocybin derivatives shown in FIGS. 7A and 7E).

In one embodiment, three of $R_2$, Ra, $R_5$, $R_6$ and $R_7$ can be a C-linked glycosyl groups, the remaining $R_2$, $R_5$, $R_6$, and $R_7$ being hydrogen atoms or alkyl group or O-alkyl groups, and $R_4$ when it is not a glycosyl group, being a phosphate group, a hydrogen atom or an alkyl group or O-alkyl group.

In one embodiment, of the three glycosyl groups, at least one of $R_2$, $R_a$, $R_5$, $R_6$ and $R_7$ can be a glycosyloxy group, and at least one of $R_2$, $R_4$, $R_5$, $R_6$ and $R_7$ can be a C-linked glycosyl group, the remaining $R_2$, $R_5$, $R_6$, or $R_7$ being independently selected from a hydrogen atom and an alkyl group or O-alkyl group, and $R_4$ when it is not a glycosyl group, being a phosphate group, a hydrogen atom or an alkyl group or O-alkyl group (see: e.g. the glycosylated psilocybin derivatives shown in FIGS. 7B, 7C, 7D and 7F).

Referring again to the chemical compound having formula (I), in one embodiment, four of $R_2$, $R_4$, $R_5$, $R_6$ and $R_7$ can be a glycosyl group, wherein the glycosyl groups are independently selected from a glycosyloxy group and C-linked glycosyl group, and wherein the non-glycosylated $R_2$, $R_5$, $R_6$, or $R_7$ is a hydrogen atom or an alkyl group or O-alkyl group, and wherein $R_4$, when it is not a glycosyl group, is a phosphate group, a hydrogen atom or an alkyl group or O-alkyl group.

Figure 8A:
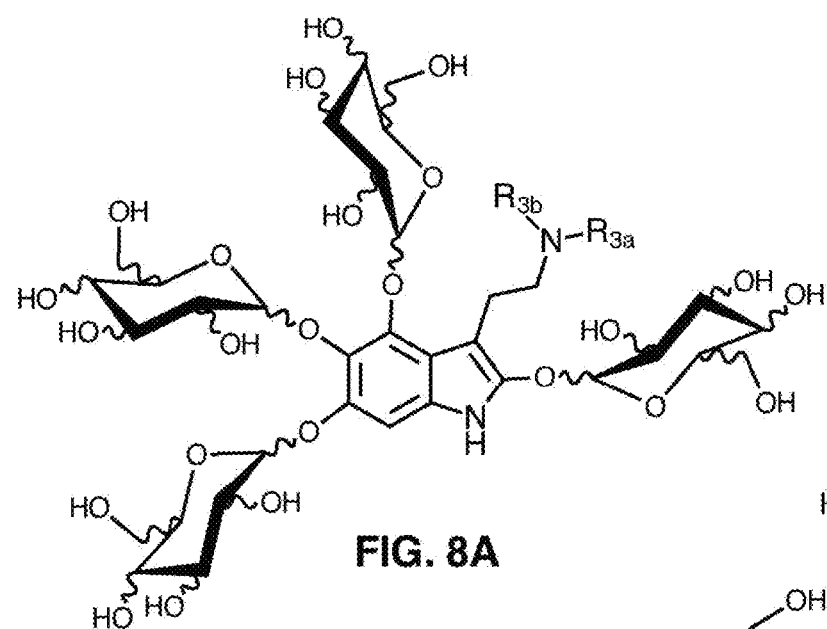
FIGS. 8A, 8B, 8C, 8D, and 8E depict the chemical structures of certain further example glycosylated psilocybin derivative compounds, notably a 2,4,5,6-tetra-glycosyloxy psilocybin derivative (FIG. 8A); a 4-glycosyloxy-5,6,7-tri-C-glyosyl psilocybin derivative (FIG. 8B); a 2,5-di-glycosyloxy-4-phospho-6,7-di-C-glycosyl psilocybin derivative (FIG. 8C); a 2,4-di-glycosyloxy-6,7-di-C-glycosyl psilocybin derivative (FIG. 8D); and a 2,4-di-glycosyloxy-5,7-di-C-glycosyl psilocybin derivative (FIG. 8E). It is noted that in each of FIGS. 8A, 8B, 8C, 8D, and 8E $R_{3a}$ and $R_{3b}$ can be a hydrogen atom, an alkyl group, an aryl group, or an acyl group.

Thus, referring to the chemical compound having formula (I), in one embodiment, $R_2$, $R_4$, $R_5$ and $R_6$ can be a glycosyl group, wherein the glycosyl groups are independently selected from a glycosyloxy group and C-linked glycosyl group, and $R_7$ can be a hydrogen atom or an alkyl group or O-alkyl group (see: the example glycosylated psilocybin derivative shown in FIG. 8A ($R_2$, $R_4$, $R_5$ and $R_6$ are each glycosyloxy groups; $R_7$ is a hydrogen atom; and $R_{3a}$ and $R_{3b}$ are a hydrogen atom, an alkyl group, an aryl group, or an acyl group)).

Figure 8B:
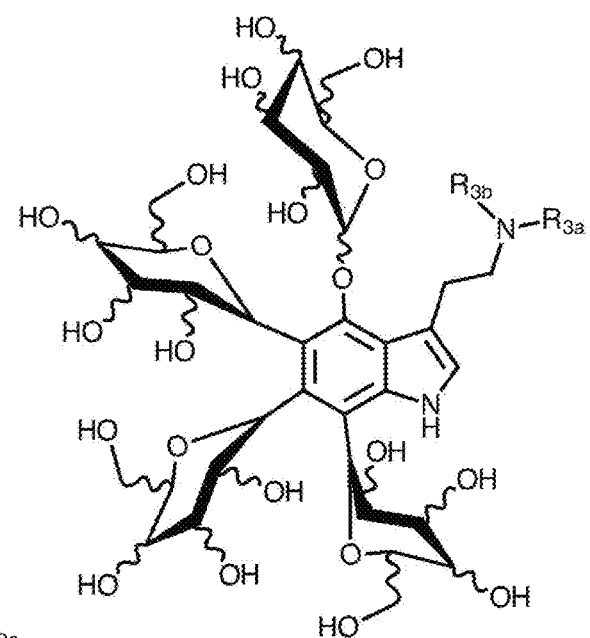

Referring to the chemical compound having formula (I), in one embodiment, $R_4$, $R_5$, $R_6$ and $R_7$ can be can be a glycosyl group, wherein the glycosyl groups are independently selected from a glycosyloxy group and C-linked glycosyl group, and $R_2$ can be a hydrogen atom or an alkyl group or O-alkyl group (see: the example glycosylated psilocybin derivative shown in FIG. 8B ($R_a$ is a glycosyloxy group; $R_5$, $R_6$ and $R_7$ are each C-linked glycosyl groups; $R_2$ is a hydrogen atom; and $R_{3a}$ and $R_{3b}$ are a hydrogen atom, an alkyl group, an aryl group, or an acyl group)).

Figure 8C:
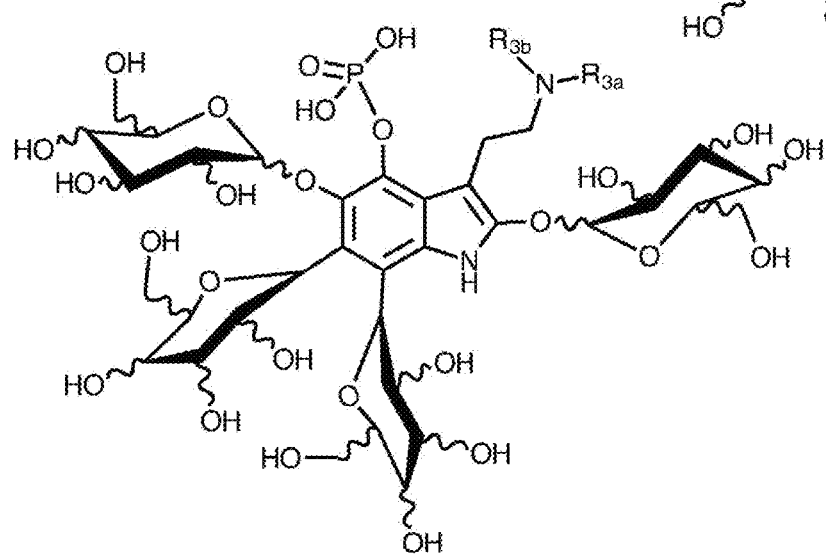

Referring to the chemical compound having formula (I), in one embodiment, $R_2$, $R_5$, $R_6$ and $R_7$ can be can be a glycosyl group, wherein the glycosyl groups are independently selected from a glycosyloxy group and C-linked glycosyl group, and $R_4$ can be a phosphate group, a hydrogen atom or an alkyl group or O-alkyl group (see: the example glycosylated psilocybin derivative shown in FIG. 8C ($R_2$ and are $R_5$ are each glycosyloxy groups; $R_6$ and $R_7$ are each C-linked glycosyl groups; $R_4$ is a phosphate group; and $R_{3a}$ and $R_{3b}$ are a hydrogen atom, an alkyl group, an aryl group, or an acyl group)).

Figure 8D:
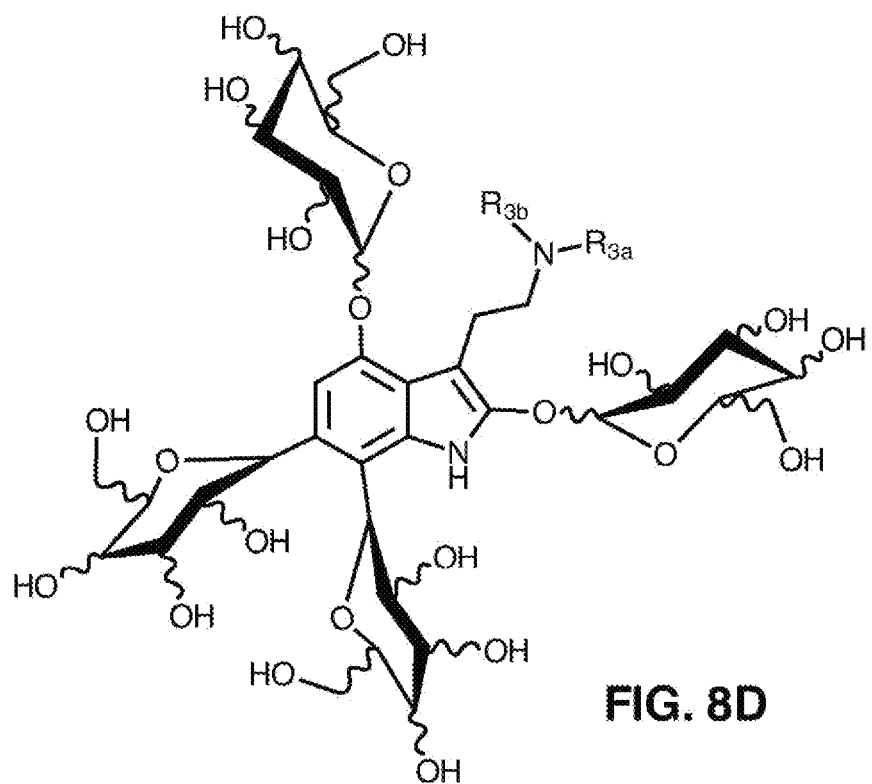

Referring to the chemical compound having formula (I), in one embodiment $R_2$, $R_4$, $R_6$ and $R_7$ can be can be a glycosyl group, wherein the glycosyl groups are independently selected from a glycosyloxy group and C-linked glycosyl group, and $R_5$ can be a hydrogen atom or an alkyl group or O-alkyl group (see: the example glycosylated psilocybin derivative shown in FIG. 8D ($R_2$, $R_4$ and are $R_6$ are each glycosyloxy groups; $R_6$ is a C-linked glycosyl group; $R_5$ is a hydrogen atom; and $R_{3a}$ and $R_{3b}$ are a hydrogen atom, an alkyl group, an aryl group, or an acyl group)).

Figure 8E:
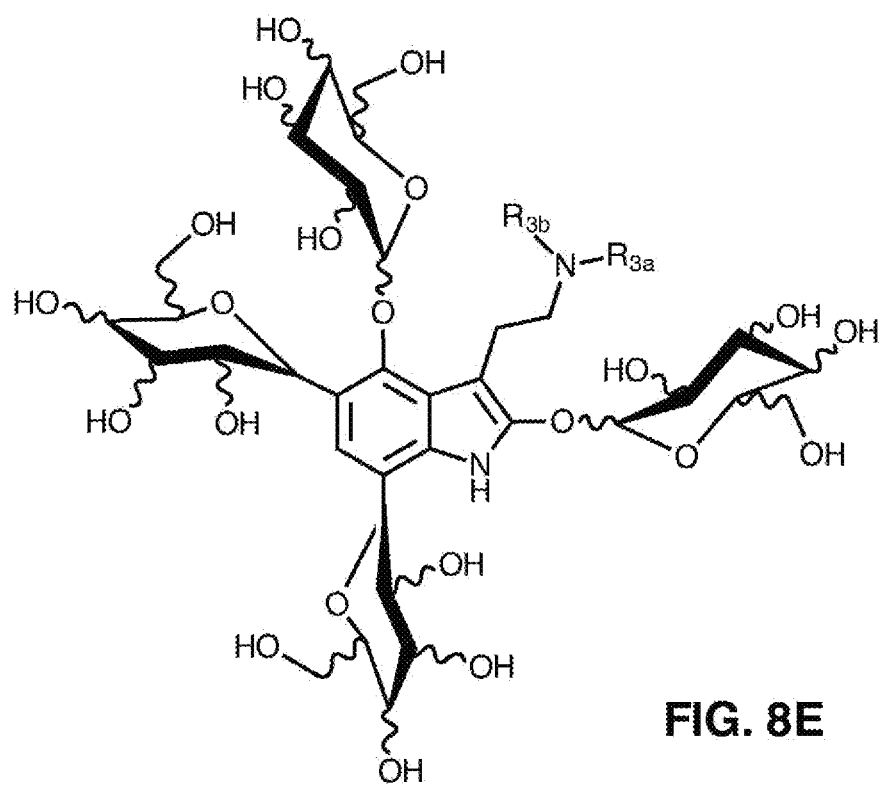

Referring to the chemical compound having formula (I), in one embodiment $R_2$, $R_4$, $R_5$ and $R_7$ can be a glycosyl group, wherein the glycosyl groups are independently selected from a glycosyloxy group and C-linked glycosyl group, and $R_6$ can be a hydrogen atom or an alkyl group or O-alkyl group (see: the example glycosylated psilocybin derivative shown in FIG. 8E ($R_2$ and $R_4$ are each a glycosyloxy group; $R_5$ and $R_7$ are each a C-linked glycosyl group; $R_6$ is a hydrogen atom; and $R_{3a}$ and $R_{3b}$ are a hydrogen atom, an alkyl group, an aryl group, or an acyl group)).

In one embodiment, four of $R_2$, $R_4$, $R_5$, $R_6$ and $R_7$ can be a glycosyloxy group, the remaining $R_2$, $R_5$, $R_6$, and $R_7$ being a hydrogen atom or an alkyl group or O-alkyl group, and $R_4$ when it is not glycosylated, being a phosphate group, a hydrogen atom or an alkyl group or O-alkyl group (see: e.g. the glycosylated psilocybin derivatives shown in FIG. 8A).

In one embodiment, four of $R_2$, $R_4$, $R_5$, $R_6$ and $R_7$ can be a C-linked glycosyl group, the remaining $R_2$, $R_5$, $R_6$, and $R_7$ being a hydrogen atom or an alkyl group or O-alkyl group, and $R_4$ when it is not a glycosylated, being a phosphate group, a hydrogen atom, or an alkyl group or O-alkyl group Referring again to the chemical compound having formula (I), in one embodiment, of the four glycosyl groups at least one of $R_2$, $R_4$, $R_5$, $R_6$ and $R_7$ can be a glycosyloxy group, and, at least one of $R_2$, $R_4$, $R_5$, $R_6$ and $R_7$ can be a C-linked glycosyl group, the remaining $R_2$, $R_5$, $R_6$, or $R_7$ being a hydrogen atom or an alkyl group or O-alkyl group, and $R_4$ when it is not a glycosyl group, being a phosphate group, a hydrogen atom or an alkyl group or O-alkyl group (see: e.g. the glycosylated psilocybin derivative shown in FIGS. 8B, 8C, 8D and 8E).

In one embodiment, all five of $R_2$, $R_4$, $R_5$, $R_6$ and $R_7$ can be a glycosyl group, wherein the glycosyl groups are independently selected from a glycosyloxy group and C-linked glycosyl group In one embodiment, of all five glycosyl groups, at least two, at least three, at least four, or all five glycosyl groups can be glycosyloxy groups.

In one embodiment, of all five glycosyl groups, at least two, at least three, at least four, or all five glycosyl groups can be C-linked glycosyl groups.

It is noted that, in a further aspect hereof, $R_{3A}$ and $R_{3B}$ can be a hydrogen atom, an alkyl group, an aryl group or an acyl group. Thus, for example, $R_{3A}$ and $R_{3B}$ can each be a hydrogen atom, or $R_{3A}$ and $R_{3B}$ can each be an alkyl group, such as a methyl group, ethyl group, propyl group, or longer chain alkyl group, or $R_{3A}$ and $R_{3B}$ can each be an aryl group, such as a phenyl group or a naphthyl group, or $R_{3A}$ and $R_{3B}$ can each be an acyl group, such as an acetyl group. Furthermore, one of $R_{3A}$ and $R_{3B}$ can be a hydrogen atom, and one of $R_{3A}$ and $R_{3B}$ can be an, and aryl group, or an acyl group. Furthermore, $R_{3A}$ and $R_{3B}$ can be an aryl group and an alkyl group, an aryl group and an acyl group, or an alkyl group and an acyl group.

Furthermore, in one embodiment, a glycosylated psilocybin derivative according to the present disclosure can be a chemical compound having the formula (III):

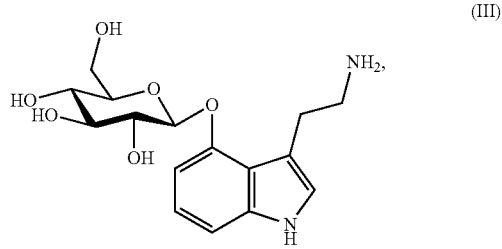

or, a chemical compound having the formula (III), wherein the glycosyloxy group is substituted for a C-linked glycosyl group.

Furthermore, in one embodiment, a glycosylated psilocybin derivative according to the present disclosure can be a chemical compound having the formula (IV):

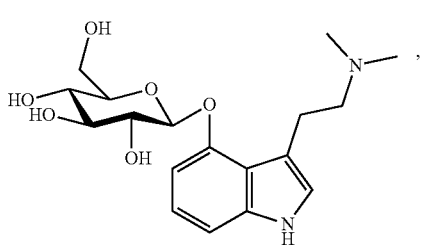

(IV)

or, a chemical compound having the formula (IV), wherein the glycosyloxy group is substituted for a C-linked glycosyl group.

It is noted that the glycosyl groups in compounds (III) and (IV) are known as β-D-glucopyranose.

Furthermore, in one embodiment, a glycosylated psilocybin derivative according to the present disclosure can be a chemical compound having the formula (V):

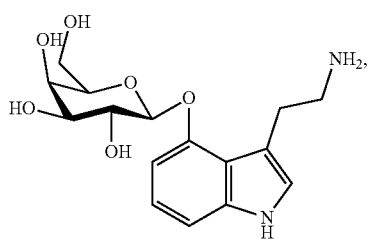

(V)

or, a chemical compound having the formula (V), wherein the glycosyloxy group is substituted for a C-linked glycosyl group.

Furthermore, in one embodiment, a glycosylated psilocybin derivative according to the present disclosure can be a chemical compound having the formula (VI):

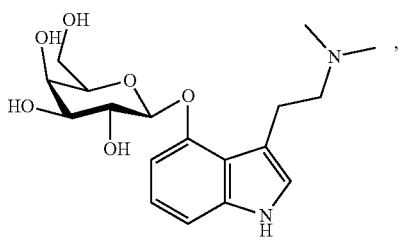

(VI)

or, a chemical compound having the formula (VI), wherein the glycosyloxy group is substituted for a C-linked glycosyl group.

It is noted that the glycosyl groups in compounds (V) and (VI) are known as β-D-galactopyranose.

Furthermore, it is noted that the glycosylated psilocybin derivatives of the present disclosure include salts thereof, including pharmaceutically acceptable salts. Thus, the nitrogen atom of the 2-aminoethyl group extending in turn from the $C_3$ atom may be protonated, and the positive charge may be balanced by, for example, chloride or sulfate ions, to thereby form a chloride salt or a sulfate salt. Furthermore, in compounds wherein $R_4$ is a phosphate group, the phosphate group may be de-protonated, and the negative charge may be balanced by, for example, sodium ions or potassium ions, to thereby form a sodium salt or a potassium salt.

Furthermore, it is noted that when $R_4$ is a phosphate group, the term glycosylated psilocybin derivative also includes compounds having the formula (VII):

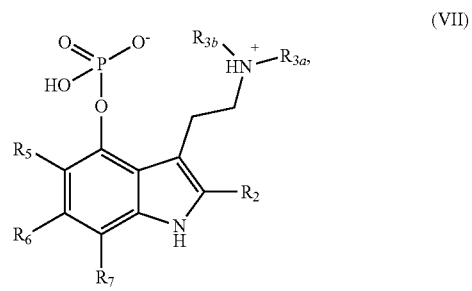

(VII)

wherein at least one of $R_2$, $R_5$, $R_6$, or $R_7$ is a glycosyl group, and wherein any $R_2$, $R_5$, $R_6$, or $R_7$ which are not a glycosyl group are a hydrogen atom or an alkyl group or O-alkyl group, and wherein $R_{3A}$ and $R_{3B}$ are a hydrogen atom, an alkyl group and aryl group or an acyl group. Further include are salts of glycosylated psilocybins having the formula (VII), such as a sodium salt, a potassium salt etc.

Thus, to briefly recap, the present disclosure provides glycosylated psilocybin derivatives. The disclosure provides, in particular, a chemical compound or salt thereof having formula (I):

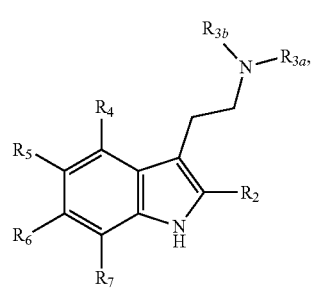

(I)

wherein in an aspect, at least one of $R_2$, $R_4$, $R_5$, $R_6$, or $R_7$ is a glycosyloxy group. In an aspect, in formula (I), each non-glycosylated $R_2$, $R_5$, $R_6$, or $R_7$ is a hydrogen atom or an alkyl group or O-alkyl group. In a further aspect, in formula (I), $R_4$ when it is not glycosylated is a hydrogen atom, an alkyl group or O-alkyl group or a phosphate group. Yet in a further aspect, $R_{3A}$ and $R_{3B}$ are a hydrogen atom, an alkyl group, an aryl group, or an acyl group.

In one embodiment of the disclosure, a chemical compound or salt thereof having formula (I) is included:

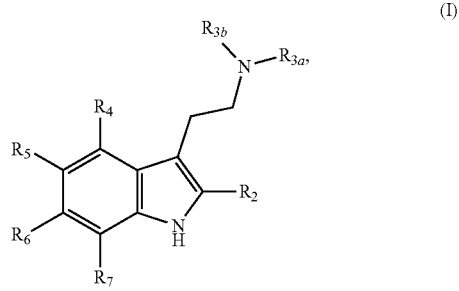

(I)

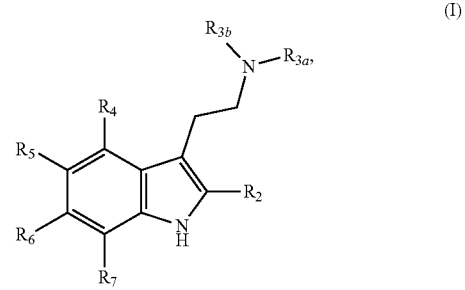

(I)

wherein $R_2$, $R_5$, $R_6$, and $R_7$ are independently or simultaneously H, an alkyl group or O-alkyl group or a glycosyl group, $R_{3A}$ and $R_{3B}$ are a hydrogen atom, an alkyl group, an aryl group, or an acyl group; and $R_4$ is hydrogen atom, alkyl group or O-alkyl group, a glycosyl group or a phosphate group; wherein at least one of $R_2$, $R_4$ $R_5$, $R_6$, and $R_7$ is a glycosyl group.

In one embodiment, $R_2$, $R_5$, $R_6$, and $R_7$ are independently or simultaneously H, $(C_1$-$C_{20})$-alkyl group or $(C_1$-$C_{20})$—O-alkyl group or a glycosyl group. In one embodiment, $R_2$, $R_5$, $R_6$, and $R_7$ are independently or simultaneously H, $(C_1$-$C_{10})$-alkyl group or $(C_1$-$C_{10})$—O-alkyl group or a glycosyl group. In one embodiment, $R_2$, $R_5$, $R_6$, and $R_7$ are independently or simultaneously H, $(C_1$-$C_6)$-alkyl group or $(C_1$-$C_6)$—O-alkyl group or a glycosyl group. In one embodiment, $R_2$, $R_5$, $R_6$, and $R_7$ are independently or simultaneously H, methyl, ethyl, propyl, O-methyl, O-ethyl, O-propyl, or a glycosyl group.

In one embodiment, $R_4$ is H, $(C_1$-$C_{20})$-alkyl group or $(C_1$-$C_{20})$—O-alkyl group, a glycosyl group or a phosphate group. In one embodiment, $R_4$ is H, $(C_1$-$C_{10})$-alkyl group or $(C_1$-$C_{10})$—O-alkyl group, a glycosyl group or a phosphate group. In one embodiment, $R_4$ is H, $(C_1$-$C_6)$-alkyl group or $(C_1$-$C_6)$—O-alkyl group, a glycosyl group or a phosphate group. In one embodiment, $R_4$ is H, methyl, ethyl, propyl, O-methyl, O-ethyl, O-propyl, a glycosyl group, or a phosphate group.

In another embodiment, $R_{3A}$ and $R_{3B}$ are a hydrogen atom, a $(C_1$-$C_{20}$-alkyl group, a $(C_6$-$C_{14})$-aryl group, or a —C(=O) $(C_1$-$C_{20})$-alkyl group. In another embodiment, $R_{3A}$ and $R_{3B}$ are a hydrogen atom, a $(C_1$-$C_{10})$-alkyl group, a $(C_6$-$C_{10})$-aryl group, or a —C(=O)$(C_1$-$C_{10})$-alkyl group or O-alkyl group. In another embodiment, $R_{3A}$ and $R_{3B}$ are a hydrogen atom, a $(C_1$-$C_6)$-alkyl group, a phenyl group, or a —C(=O)$(C_1$-$C_6)$-alkyl group. In another embodiment, $R_{3A}$ and $R_{3B}$ are a hydrogen atom, a methyl group, an ethyl group, a propyl group, a phenyl group, —C(=O)—$CH_3$, —C(=O)—$CH_2CH_3$, or —C(=O)—$CH_2CH_2CH_3$.

The glycosylated psilocybin derivatives of the present disclosure may be used to prepare a pharmaceutical or recreational drug formulation. Thus in one embodiment, the present disclosure further provides in another aspect, pharmaceutical and recreational drug formulations comprising glycosylated psilocybin derivatives. Accordingly, in one aspect, the present disclosure provides in a further embodiment a pharmaceutical or recreational drug formulation comprising a chemical compound having formula (I):

wherein at least one of $R_2$, $R_4$, $R_5$, $R_6$, or $R_7$ is a glycosyl group, and wherein each non-glycosylated $R_2$, $R_5$, $R_6$, or $R_7$ is a hydrogen atom or an alkyl group or O-alkyl group, wherein $R_4$ when it is not glycosylated is a hydrogen atom, alkyl group or O-alkyl group, or a phosphate group, and wherein $R_{3A}$ and $R_{3B}$ are a hydrogen atom, an alkyl group, an aryl group, or an acyl group.

In one embodiment, at least one of $R_2$, Ra, $R_5$, $R_6$, or $R_7$ is a glycosyl group, and wherein each non-glycosylated $R_2$, $R_5$, $R_6$, or $R_7$ is a hydrogen atom or a $(C_1$-$C_{20})$-alkyl group or $(C_1$-$C_{20})$—O-alkyl group, wherein $R_4$ when it is not glycosylated is a hydrogen atom, a $(C_1$-$C_{20})$-alkyl group or $(C_1$-$C_{20})$—O-alkyl group, or a phosphate group.

In another embodiment, each non-glycosylated $R_2$, $R_5$, $R_6$, or $R_7$ is a hydrogen atom or a $(C_1$-$C_{10})$-alkyl group or $(C_1$-$C_{10})$—O-alkyl group. In another embodiment, each non-glycosylated $R_2$, $R_5$, $R_6$, or $R_7$ is a hydrogen atom or a $(C_1$-$C_6)$-alkyl group or $(C_1$-$C_6)$—O-alkyl group. In another embodiment, each non-glycosylated $R_2$, $R_5$, $R_6$, or $R_7$ is a hydrogen atom, a methyl group, ethyl group, a propyl group, an O-methyl group, an O-ethyl group, or an O-propyl group.

In another embodiment, when $R_4$ is not glycosylated, $R_4$ is a hydrogen atom, a $(C_1$-$C_{20})$-alkyl group or $(C_1$-$C_{20})$—O-alkyl group, or a phosphate group. In another embodiment, when $R_4$ is not glycosylated, $R_4$ is a hydrogen atom, a $(C_1$-$C_{10})$-alkyl group or $(C_1$-$C_{10})$—O-alkyl group, or a phosphate group. In another embodiment, when $R_4$ is not glycosylated, $R_4$ is a hydrogen atom, a $(C_1$-$C_6)$-alkyl group or $(C_1$-$C_6)$—O-alkyl group, or a phosphate group. In another embodiment, when $R_4$ is not glycosylated, $R_4$ is a hydrogen atom, a methyl group, an ethyl group, a propyl group, a phosphate group, an O-methyl group, an O-ethyl group, or an O-propyl group.

In another embodiment, $R_{3A}$ and $R_{3B}$ are a hydrogen atom, a $(C_1$-$C_{20})$-alkyl group, a $(C_6$-$C_{14})$-aryl group, or a —C(=O)$(C_1$-$C_{20})$-alkyl group. In another embodiment, $R_{3A}$ and $R_{3B}$ are a hydrogen atom, a $(C_1$-$C_{10})$-alkyl group, a $(C_6$-$C_{10})$-aryl group, or a —C(=O)$(C_1$-$C_{10})$-alkyl group. In another embodiment, $R_{3A}$ and $R_{3B}$ are a hydrogen atom, a $(C_1$-$C_6)$-alkyl group, a phenyl group, or a —C(=O)$(C_1$-$C_6)$-alkyl group. In another embodiment, $R_{3A}$ and $R_{3B}$ are a hydrogen atom, a methyl group, an ethyl group, a propyl group, a phenyl group, —C(=O)—$CH_3$, —C(=O)—$CH_2CH_3$, or —C(=O)—$CH_2CH_2CH_3$.

In one embodiment of the disclosure, a chemical compound or salt thereof having formula (I) is included:

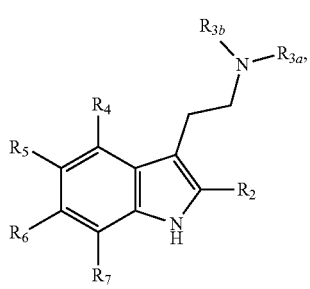

(I)

wherein at least one of $R_2$, Ra, $R_5$, $R_6$, or $R_7$ is a glycosyl group, and wherein each non-glycosylated $R_2$, $R_5$, $R_6$, or $R_7$ is a hydrogen atom or an alkyl group or O-alkyl group, wherein $R_4$ when it is not glycosylated is a hydrogen atom, an alkyl group or O-alkyl group or a phosphate group, and wherein $R_{3A}$ and $R_{3B}$ are a hydrogen atom an alkyl group, an aryl group, or an acyl group, or a slat of the chemical compound, together with a diluent, carrier or excipient.

The dose when using the compounds of the present disclosure can vary within wide limits, and as is customary and is known to those of skill in the art, the dose can be tailored to the individual conditions in each individual case. The dose depends, for example, on the nature and severity of the illness to be treated, on the condition of the patient, on the compound employed or on whether an acute or chronic disease state is treated or prophylaxis is conducted, on the mode of delivery of the compound, or on whether further active compounds are administered in addition to the compounds of the present disclosure. Representative doses of the present disclosure include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to about 100 mg, about 0.001 mg to about 50 mg, and about 0.001 mg to about 25 mg. Representative doses of the present disclosure include, but are not limited to, about 0.0001 to about 1,000 mg, about 10 to about 160 mg, about 10 mg, about 20 mg, about 40 mg, about 80 mg, or about 160 mg. Multiple doses may be administered during the day, especially when relatively large amounts are deemed to be needed, for example 2, 3 or 4, doses. Depending on the subject and as deemed appropriate from the patient's physician or care giver it may be necessary to deviate upward or downward from the doses described herein.

The pharmaceutical or recreational drug formulations may be prepared as liquids, tablets, capsules, microcapsules, nanocapsules, trans-dermal patches, gels, foams, oils, aerosols, nanoparticulates, powders, creams, emulsions, micellar systems, films, sprays, ovules, infusions, teas, decoctions, suppositories, etc. and include a pharmaceutically acceptable salt or solvate of the glycosylated psilocybin compound together with an excipient. The term "excipient" as used herein means any ingredient other than the chemical compound of the disclosure. As will readily be appreciated by those of skill in art, the selection of excipient may depend on factors such as the particular mode of administration, the effect of the excipient on solubility of the chemical compounds of the present disclosure and methods for their preparation will be readily apparent to those skilled in the art. Such compositions and methods for their preparation may be found, for example, in "Remington's Pharmaceutical Sciences", 22nd Edition (Pharmaceutical Press and Philadelphia College of Pharmacy at the University of the Sciences, 2012).

The pharmaceutical and drug formulations comprising the glycosylated psilocybin derivatives of the present disclosure may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, microcapsules, or powders), lozenges (including liquid-filled lozenges), chews, multi- and nano-particulates, gels, solid solutions, liposomal preparations, microencapsulated preparations, creams, films, ovules, suppositories and sprays.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80. When present, surface active agents may comprise from 0.2% (w/w) to 5% (w/w) of the tablet.

Tablets may further contain lubricants such as magnesium stearate, calcium stearate, zinc stearate, sodium stearyl fumarate, and mixtures of magnesium stearate with sodium lauryl sulphate. Lubricants generally comprise from 0.25% (w/w) to 10% (w/w), from 0.5% (w/w) to 3% (w/w) of the tablet.

In addition to the glycosylated psilocybin derivative, tablets may contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1% (w/w) to 25% (w/w) or from 5% (w/w) to 20% (w/w) of the dosage form.

Other possible auxiliary ingredients include anti-oxidants, colourants, flavouring agents, preservatives and taste-masking agents.

For tablet dosage forms, depending on the desired effective amount of the chemical compound, the chemical compound of the present disclosure may make up from 1% (w/w) to 80% (w/w) of the dosage form, more typically from 5% (w/w) to 60% (w/w) of the dosage form.

Exemplary tablets contain up to about 80% (w/w) of the chemical compound, from about 10% (w/w) to about 90%

(w/w) binder, from about 0% (w/w) to about 85% (w/w) diluent, from about 2% (w/w) to about 10% (w/w) disintegrant, and from about 0.25% (w/w) to about 10% (w/w) lubricant.

The formulation of tablets is discussed in "Pharmaceutical Dosage Forms: Tablets", Vol. 1-Vol. 3, by CRC Press (2008).

The pharmaceutical and recreational drug formulations comprising the glycosylated psilocybin derivatives of the present disclosure may also be administered directly into the blood stream, into muscle, or into an internal organ. Thus, the pharmaceutical and recreational drug formulations can be administered parenterally (for example, by subcutaneous, intravenous, intraarterial, intrathecal, intraventricular, intracranial, intramuscular, or intraperitoneal injection). Parenteral formulations are typically aqueous solutions which may contain excipients such as salts, carbohydrates and buffering agents (in one embodiment, to a pH of from 3 to 9), but, for some applications, they may be more suitably formulated as a sterile non-aqueous solution or as a dried form to be used in conjunction with a suitable vehicle such as sterile water.

Formulations comprising the glycosylated psilocybin derivatives of the present disclosure for parenteral administration may be formulated to be immediate and/or modified release. Modified release formulations include delayed-, sustained-, pulsed-, controlled-, targeted and programmed release. Thus the chemical compounds of the disclosure may be formulated as a solid, semi-solid, or thixotropic liquid for administration as an implanted depot providing modified release of the active compound. Examples of such formulations include drug-coated stents and poly(dl-lactic-coglycolic) acid (PGLA) microspheres.

The pharmaceutical or recreational drug formulations of the present disclosure also may be administered topically to the skin or mucosa, i.e. dermally or transdermally. Example pharmaceutical and recreational drug formulations for this purpose include gels, hydrogels, lotions, solutions, creams, ointments, dusting powders, cosmetics, oils, eye drops, dressings, foams, films, skin patches, wafers, implants, sponges, fibres, bandages and microemulsions. Liposomes may also be used. Example carriers include alcohol, water, mineral oil, liquid petrolatum, white petrolatum, glycerin, polyethylene glycol and propylene glycol. Penetration enhancers may be incorporate (see: for example, Finnin, B. and Morgan, T. M., 1999 J. Pharm. Sci, 88 (10), 955-958).

Other means of topical administration include delivery by electroporation, iontophoresis, phonophoresis, sonophoresis and microneedle or needle-free (e.g. Powderject™, Bioject™, etc.) injection.

Pharmaceutical and recreational drug formulations for inhalation or insufflation include solutions and suspensions in pharmaceutically acceptable, aqueous or organic solvents, or mixtures thereof, and powders. The liquid or solid pharmaceutical compositions can contain suitable pharmaceutically acceptable excipients. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally or nasally, from devices that deliver the formulation in an appropriate manner.

In further embodiments, in which the glycosylated psilocybin compounds of present disclosure are used as a recreational drug, the compounds may be included in compositions such as a food or food product, a beverage, a food seasoning, a personal care product, such as a cosmetic, perfume or bath oil, or oils (both for topical administration as massage oil, or to be burned or aerosolized). The chemical compounds of the present disclosure may also be included in a "vape" product, which may also include other drugs, such as nicotine, and flavorings.

The pharmaceutical formulations comprising the chemical compounds of the present disclosure may be used to treat a subject, and in particular to treat a psychiatric disorder in a subject. Accordingly, the present disclosure includes in a further embodiment, a method for treating a psychiatric disorder, the method comprising administering to a subject in need thereof a pharmaceutical formulation comprising a chemical compound or salt thereof having formula (I):

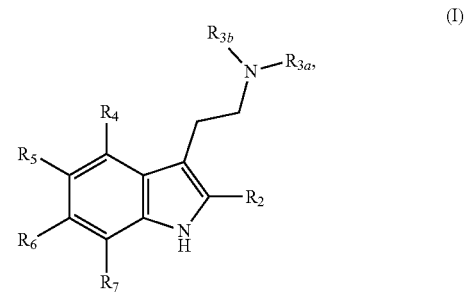

(I)

wherein at least one of $R_2$, $R_4$, $R_5$, $R_6$, or $R_7$ is a glycosyl group, and wherein each non-glycosylated $R_2$, $R_5$, $R_6$, or $R_7$ is a hydrogen atom or an alkyl group or O-alkyl group, wherein $R_4$ when it is not glycosylated is a hydrogen atom, an alkyl group or O-alkyl group or a phosphate group, and wherein $R_{3A}$ and $R_{3B}$ are a hydrogen atom, an alkyl group, an aryl group, or an acyl group, together with a diluent, carrier or excipient.

Psychiatric disorders that may be treated include, for example, neurodevelopmental disorders such as intellectual disability, global development delay, communication disorders, autism spectrum disorder, and attention-deficit hyperactivity disorder (ADHD); bipolar and related disorders, such as mania, and depressive episodes; anxiety disorder, such as generalized anxiety disorder (GAD), agoraphobia, social anxiety disorder, specific phobias (natural events, medical, animal, situational, for example), panic disorder, and separation anxiety disorder; stress disorders, such as acute stress disorder, adjustment disorders, post-traumatic stress disorder (PTSD), and reactive attachment disorder; dissociative disorders, such as dissociative amnesia, dissociative identity disorder, and depersonalization/derealization disorder; somatoform disorders, such as somatic symptom disorders, illness anxiety disorder, conversion disorder, and factitious disorder; eating disorders, such as anorexia nervosa, bulimia nervosa, rumination disorder, pica, and binge-eating disorder; sleep disorders, such as narcolepsy, insomnia disorder, hypersomnolence, breathing-related sleep disorders, parasomnias, and restless legs syndrome; disruptive disorders, such as kleptomania, pyromania, intermittent explosive disorder, conduct disorder, and oppositional defiant disorder; depressive disorders, such as disruptive mood dysregulation disorder, major depressive disorder, persistent depressive disorder (dysthymia), premenstrual dysphoric disorder, substance/medication-induced depressive disorder, postpartum depression, and depressive disorder caused by another medical condition, for example, psychiatric and existential distress within life-threatening cancer situations (ACS Pharmacol. Transl. Sci. 4: 553-562; J Psychiatr Res 137: 273-282); substance-related disorders, such as alcohol-related disorders, *cannabis* related disorders, inhalant-use related disorders, stimulant use disorders, and tobacco use disorders; neurocognitive disorders, such as delirium; schizophrenia; compulsive disorders, such as obsessive compulsive disorders (OCD), body dysmorphic disorder, hoarding disorder, trichotillomania disorder, excoriation disorder, substance/medication induced obsessive-compulsive disorder, and obsessive-compulsive disorder related to another medical condition; and personality disorders, such as antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, schizotypal personality disorder.

In an aspect, the compounds of the present disclosure may be used to be contacted with a 5-HT$_{2A}$ receptor to thereby modulate the 5-HT$_{2A}$ receptor. Such contacting includes bringing a compound of the present disclosure and 5-HT$_{2A}$ receptor together under in vitro conditions, for example, by introducing the compounds in a sample containing a 5-HT$_{2A}$ receptor, for example, a sample containing purified 5-HT$_{2A}$ receptors, or a sample containing cells comprising 5-HT$_{2A}$ receptors. In vitro conditions further include the conditions described in Example 3 hereof. Contacting further includes bringing a compound of the present disclosure and 5-HT$_{2A}$ receptor together under in vivo conditions. Such in vivo conditions include the administration to an animal or human subject, for example, of a pharmaceutically effective amount of the compound of the present disclosure, when the compound is formulated together with a pharmaceutically active carrier, diluent or excipient, as hereinbefore described, to thereby treat the subject. Upon having contacted the 5-HT$_{2A}$ receptor, the compound may activate the 5-HT$_{2A}$ receptor or inhibit the 5-HT$_{2A}$ receptor.

Thus, in a further aspect, the condition that may be treated in accordance herewith can be any 5-HT$_{2A}$ receptor mediated disorder. Such disorders include, but are not limited to schizophrenia, psychotic disorder, attention deficit hyperactivity disorder, autism, and bipolar disorder.

Turning now to methods of making the glycosylated psilocybin derivatives of the present disclosure, it is initially noted that the glycosylated psilocybin derivatives of the present disclosure may be prepared in any suitable manner, including by any organic chemical synthesis methods, bio-synthetic methods, or a combination thereof.

One suitable method of to making the glycosylated psilocybin derivatives of the present disclosure initially involves selecting and obtaining or preparing a hydroxy-containing psilocybin derivative compound. Suitable hydroxy-containing psilocybin derivative compounds include compounds comprising an indole prototype structure (see: FIG. 2), including, for example, a chemical compound or salt thereof having formula (II)

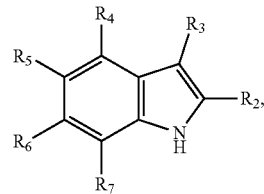

(II)

wherein at least one of $R_2$, Ra, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein $R_3$ is a hydrogen atom, 2-aminoethyl group, or an N-substituted 2-aminoethyl group, and wherein $R_4$ when it is not hydroxylated is a hydrogen atom, an alkyl group or O-alkyl group or a phosphate group. Hydroxy-containing psilocybin derivative compound (II) comprises a plurality of compounds, some examples of which will next be described.

Figure 3A:
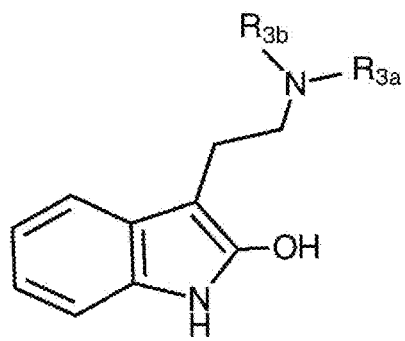
FIGS. 3A, 3B, 3C, 3D, and 3E depict the chemical structures of certain example hydroxy-containing psilocybin derivatives, notably a 2-hydroxy-psilocybin derivative (FIG. 3A); a 4-hydroxy-psilocybin derivative (FIG. 3B); a 5-hydroxy-psilocybin derivative (FIG. 3C); a 6-hydroxy-psilocybin derivative (FIG. 3D); and a 7-hydroxy-psilocybin derivative (FIG. 3E), wherein non-hydroxylated residues $C_2$, $C_4$, $C_5$, $C_6$ and $C_7$ are bonded to a hydrogen atom.

In one example embodiment, the hydroxy-containing psilocybin derivative can be selected to be a chemical compound wherein $R_2$ is a hydroxy group, $R_5$, $R_6$, and $R_7$ are a hydrogen atom or an alkyl group or O-alkyl group, and $R_4$ is hydrogen atom, an alkyl group or O-alkyl group or a phosphate group, and wherein the 2-aminoethyl group comprises $R_{3A}$ and $R_{3B}$ which are a hydrogen atom an alkyl group or O-alkyl group, such as, for example, the hydroxy-containing psilocybin derivative shown in FIG. 3A.

Figure 3B:
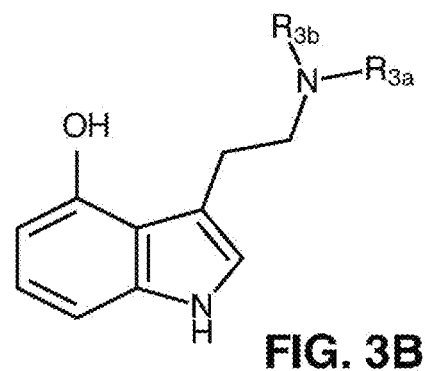

In one example embodiment, the hydroxy-containing psilocybin derivative can be selected to be a chemical compound wherein $R_4$ can be a hydroxy group, $R_2$, $R_5$, $R_6$, and $R_7$ are a hydrogen atom or an alkyl group or O-alkyl group, and wherein the 2-aminoethyl group comprises $R_{3A}$ and $R_{3B}$ which are a hydrogen atom or an alkyl group, such as, for example, the hydroxy-containing psilocybin derivative shown in FIG. 3B.

Figure 3C:
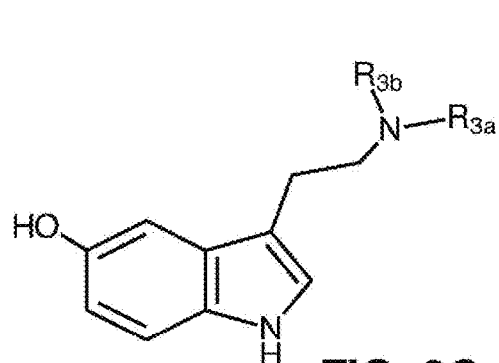

In one example embodiment, the hydroxy-containing psilocybin derivative can be selected to be a chemical compound wherein $R_5$ can be a hydroxy group, $R_2$, $R_6$, and $R_7$ are a hydrogen atom or an alkyl group or O-alkyl group, and $R_4$ is hydrogen atom, an alkyl group or O-alkyl group or a phosphate group, and wherein the 2-aminoethyl group comprises $R_{3A}$ and $R_{3B}$ which are a hydrogen atom or an alkyl group, such as, for example, the hydroxy-containing psilocybin derivative shown in FIG. 3C.

Figure 3D:
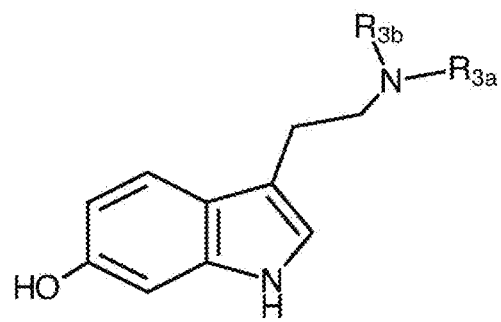

In one example embodiment, the hydroxy-containing psilocybin derivative can be selected to be a chemical compound wherein $R_6$ can be a hydroxy group, $R_2$, $R_5$, and $R_7$ are a hydrogen atom or an alkyl group or O-alkyl group, and $R_4$ is hydrogen atom, an alkyl group or O-alkyl group or a phosphate group, and wherein the 2-aminoethyl group comprises $R_{3A}$ and $R_{3B}$ which are a hydrogen atom or an alkyl group, such as, for example, the hydroxy-containing psilocybin derivative shown in FIG. 3D.

Figure 3E:
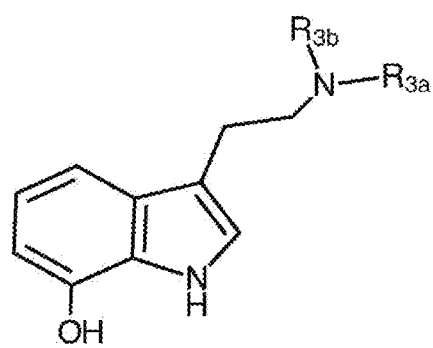

In one example embodiment, the hydroxy-containing psilocybin derivative can be selected to be a chemical compound wherein $R_7$ can be a hydroxy group, $R_2$, $R_5$, and $R_6$ are a hydrogen atom or an alkyl group or O-alkyl group, and $R_4$ is a hydrogen atom, an alkyl group or O-alkyl group or a phosphate group, and wherein the 2-aminoethyl group comprises which $R_{3A}$ and $R_{3B}$ are a hydrogen atom or an alkyl group, such as, for example, the hydroxy-containing psilocybin derivative shown in FIG. 3E.

The hydroxy-containing psilocybin derivative compounds may be provided in a more or less chemically pure form, for example, in the form of a hydroxy-containing psilocybin derivative preparation having a purity of at least about 95%, at least about 96%, at least about 97%, at least about 98%, at least about 99%, or at least 99.9%. The hydroxy-containing psilocybin derivative may be chemically synthesized, or obtained from a fine chemical manufacturer.

Turning now to the glycosyl compounds, in general, in accordance herewith any glycosyl compound may be selected, obtained or prepared and used. Suitable glycosyl compounds include, for example, hexosyl or pentosyl compounds. Further suitable compounds include mono-saccharides, disaccharides, tri-saccharides and poly-saccharides.

In an example embodiment, glycosyl compounds which may be selected are glucose and glucosyl containing compounds and glucose and glucosyl derivatives, such as uridine diphosphate glucose (UDP-glucose).

In a further example embodiment, glycosyl compounds which may be selected are glucuronic acid and derivatives thereof.

In a further example embodiment, glycosyl compounds which may be selected are galactose and galactosyl containing compounds and galactose and galactosyl derivatives, such as uridine diphosphate galactose (UDP-galactose).

In a further example embodiment, glycosyl compounds which may be selected are mannose and derivatives thereof.

In a further example embodiment, glycosyl compounds which may be selected are fucose and fucosyl containing compounds and fucose and fucosyl derivatives.

In a further example embodiment, glycosyl compounds which may be selected are xylose and derivatives thereof, In a further example embodiment, glycosyl compounds which may be selected are arabinose and derivatives thereof.

In a yet further example embodiment, glycosyl compounds which may be selected are and rhamnose and derivatives thereof.

The glycosyl compound may be provided in a more or less chemically pure form, for example, in the form of a glycosyl compound preparation having a purity of at least about 95%, at least about 96%, at least about 97%, at least about 98%, at least about 99%, or at least 99.9%. The glycosyl compound may be chemically synthesized, or obtained from a fine chemical manufacturer.

Thus, initially, in an aspect hereof, a hydroxy-containing psilocybin derivative and a glycosyl compound and glycosyl transferase are provided, and the hydroxy-containing psilocybin derivative compound and a glycosyl compound are contacted to react in a chemical reaction resulting in the formation of a glycosylated psilocybin derivative compound.

Figure 9:
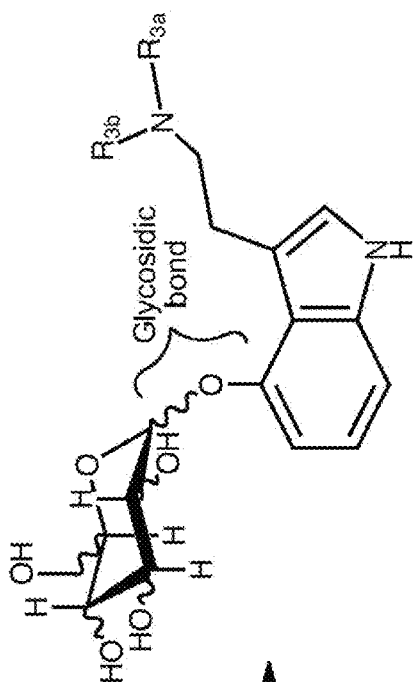
FIG. 9 depicts an example chemical reaction for synthesizing a glycosylated psilocybin derivative, notably a reaction wherein a 4-hydroxy-psilocybin derivative is reacted with a glycosyl compound to form a 4-glycosyl-psilocybin derivative.
Figure 9:
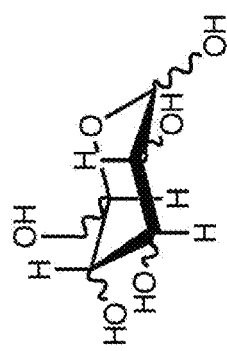
Figure 9:
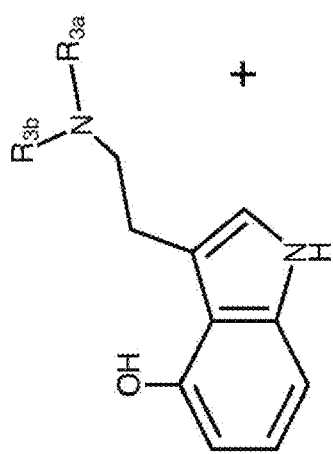

Referring now to FIG. 9, shown therein is an example chemical reaction wherein glucose is reacted with a 4-hydroxy-psilocybin derivative in a chemical reaction which results in the formation of a 4-glycosylated psilocybin derivative. It is noted in that in the chemical reaction a glycosidic bond is formed. Thus, it will be clear that in one embodiment, the glycosylated psilocybin derivative can be formed in a reaction between a glycosyl compound and a hydroxy-containing psilocybin derivative, wherein the hydroxy group of the hydroxy-containing psilocybin derivative reacts with the glycosyl compound to form a glycosidic bond. It is noted that the reaction depicted in FIG. 9 shows a reaction between the 4-hydroxy-psilocybin derivative depicted an FIG. 3B and glucose, resulting the glycosylated 4-glycosyloxy-psilocybin product shown in FIG. 4B.

Thus, it will now be clear that, in an aspect hereof, the hydroxy-containing psilocybin derivatives disclosed herein may be reacted with glycosyl compounds to form the glycosylated psilocybin derivatives of the present disclosure. Thus, in addition to 4-hydroxy-psilocybin shown in FIG. 3B, the example hydroxy-containing psilocybin derivatives shown in FIGS. 3A, 3C, 3D, and 3E may be reacted with glucose to form the glycosylated psilocybin derivatives shown in FIGS. 4A, 4C, 4D and 4E, respectively.

Figure 11A:
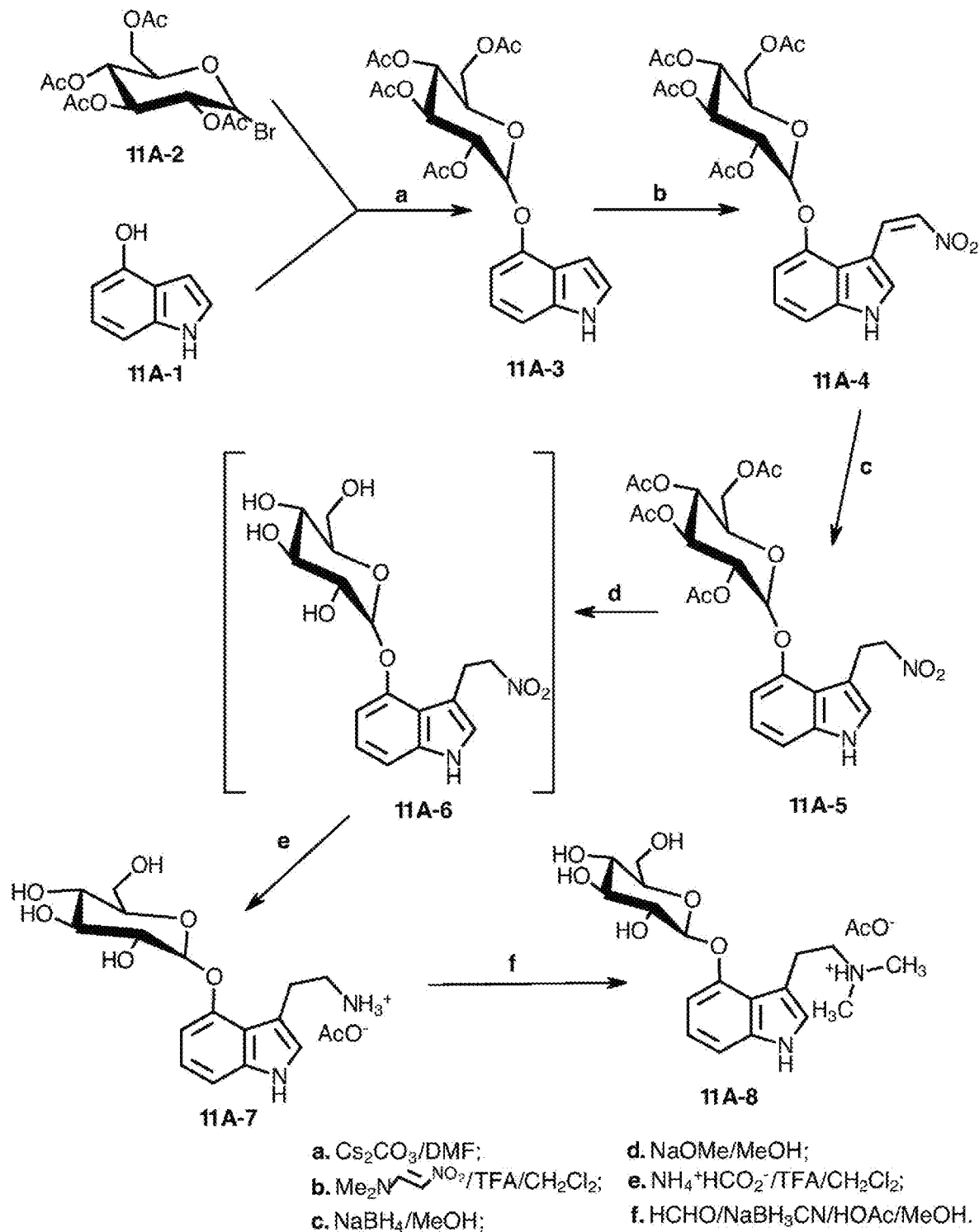
FIGS. 11A and 11B depict example chemical synthesis processes for the synthesis of certain example glycosylated psilocybin derivatives, notably an example process for example glucosyl psilocybin derivatives (denoted as compounds 11A-7 and 11A-8) (FIG. 11A) and an example process for example galactosyl psilocybin derivatives (denoted as compounds 11B-7 and 11B-8) (FIG. 11B).

Referring now to FIG. 11A, shown therein is an example of chemical synthesis of 4-O-β-D-glucopyranosylated psilocybin derivative compounds of formula (III) and (IV), isolated in acetic acid salt forms. The synthesis involves the use of 4-hydroxyindole (11A-1) as a starting material. First, the glycosylation of hydroxyindole (11A-1) with 2,3,4,6-tetra-O-acetyl-α-D-glucopyranosyl bromide (11A-2) in DMF using cesium carbonate as a base can provide the desired β-D-glucopyranoside 11A-3. A subsequent 3-nitrovinylation can be carried out by reacting compound 11A-3 with 1-(dimethylamino)-2-nitroethylene under the catalysis of trifluoroacetic acid to furnish the desired compound 11A-4. The alkene functionality of compound 11A-4 can then be reduced by sodium borohydride in methanol to provide compound 11A-5. The synthesis can continue by removing all the 0-acetate protecting groups of compound 11A-5 to provide the intermediate tetra-ol 11A-6 which can subsequently be reduced using ammonium formate and 10% palladium on charcoal in methanol at 60° C. to yield the targeted 4-O-β-D-glucopyranosyltryptamine derivative 11A-7 (see: the chemical compound having formula (III)), isolated in the acetic acid salt form. Furthermore, the primary amine functionality of compound 11A-7 can be subjected to a reductive amination using an excess of formaldehyde and sodium cyanoborohydride in methanol to furnish the targeted N,N-dimethyl-4-O-β-D-galactopyranosyltryptamine compound 11A-8 (see: the chemical compound having formula (IV)), isolated in the acetic acid salt form.

Figure 11B:
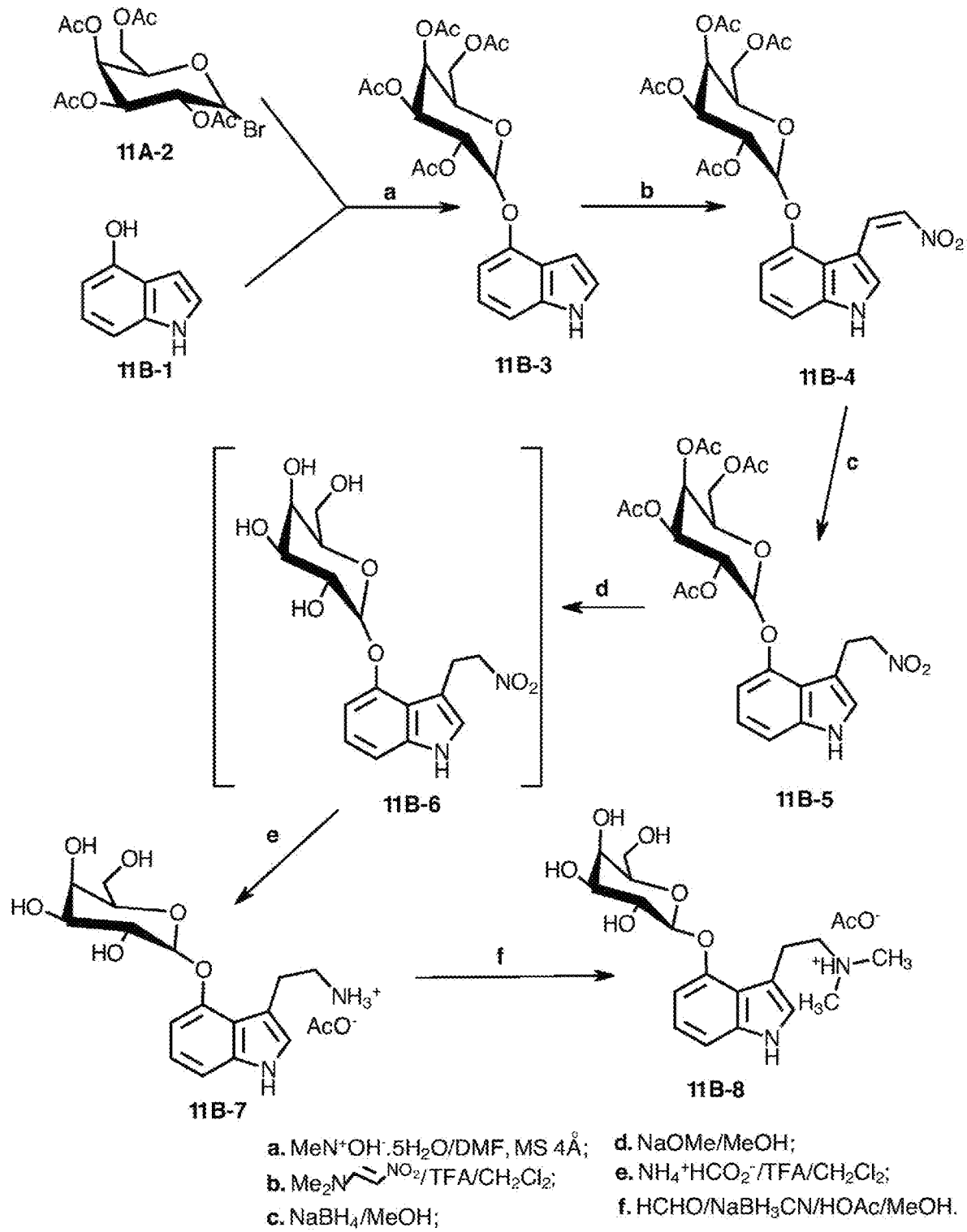

Referring now to FIG. 11B, shown therein is an example of chemical synthesis of 4-O-δ-D-galactopyranosylated psilocybin derivative compounds of formula (V) and (VI), isolated in acetic acid salt forms. The synthesis involves the use of 4-hydroxyindole (11B-1) as a starting material. First, the glycosylation of hydroxyindole (11B-1) with 2,3,4,6-tetra-O-acetyl-α-D-galactopyranosyl bromide (11B-2) in DMF using tetramethylammonium hydroxide pentahydrate as a base can provide the desired β-D-galactopyranoside 11B-3. A subsequent 3-nitrovinylation can be carried out by reacting compound 11B-3 with 1-(dimethylamino)-2-nitroethylene under the catalysis of trifluoroacetic acid to furnish the desired compound 11B-4. The alkene functionality of compound 11B-4 can then be reduced by sodium borohydride in methanol to afford compound 11B-5. The synthesis can continue by removing all the 0-acetate protecting groups of compound 11 B-5 to provide the intermediate tetra-ol 11B-6 which can be subsequently reduced using ammonium formate and 10% palladium on charcoal in methanol at 60° C. to yield the targeted 4-O-β-D-galactopyranosyltryptamine derivative 11B-7 (see: the chemical compound having formula (V)), isolated in the acetic acid salt form. Furthermore, the primary amine functionality of compound 11B-7 can be subjected to a reductive amination using an excess of formaldehyde and sodium cyanoborohydride in methanol to furnish the targeted N,N-dimethyl-4-O-β-D-galactopyranosyltryptamine compound 11B-8 (see: the chemical compound having formula (VI)), isolated in the acetic acid salt form.

It is noted that following synthesis the desired glycosyl derivative psilocybin compounds may be separated from other reactants and obtained in more or less pure form, for example, in at least 95%, at least 96%, at least 97%, at least 98%, or at least 99% pure form, using purification methods generally known to those of skill in the art.

Thus, It is noted that the reactions depicted in FIGS. 11A and 11B show reaction sequences starting from the 4-hydroxyindole and 2,3,4,6-tetra-O-acetyl-α-D-glycosyl bromide, resulting in the 4-O-glycosyl-psilocybin products shown in FIG. 4B. It is noted that formation of β-4-O-glycosyl-psilocybin products involved the use of a 4-hydroxyindole as a starting material. Other 4-O-β-D-glucosyl/galactosyl-psilocybin derivatives can be formed by following a similar reaction sequence reaction using a 4-hydroxyindole derivative that contains one or more compatible substituent(s) on the ring, such as alkyl, halides etc. The amount of formaldehyde in the final reductive amination step can be reduced to allow mono N-alkylation, and the formaldehyde can be switched to any other aldehyde/ketone to obtain variants of substituents on the nitrogen. The amine functionality can also be N-alkylated using an appropriate alkylating reagent such as an alkyl halide, alkyl p-tosylate/mesylate/triflate, or conjugated reagents such as α,β-unsaturated ester/amide/aldehyde/ketone (Michael additions) to afford higher substituted amines or quaternary ammonium salts. Multiple N-alkylations can be carried out in one-pot or stepwise manner using the same or different alkyl halides. The amine functionality can also be N-acylated using an appropriate acylating reagent such as an acid anhydride or acyl halide.

Thus, it will now be clear that, in an aspect hereof, other glycosyl psilocybin derivatives can be formed by following a similar reaction sequence reaction using an indole derivative that contains one or more hydroxyl groups on the indole ring, as a starting material. The 2,3,4,6-tetra-O-acetyl-α-D-glucopyranosyl/galactopyranosyl bromides can be changed to other glycosyl halides to form the desired glycosidic bond. The glycosyl bromide can be changed to other types of glycosyl donors such as glycosyl imidates, thioglycoside, glycosyl fluoride, glycosyl 1-O-acetate etc. with different protecting group patterns. Using well-established activation conditions, the corresponding α- or β-glycosylated psilocybin derivatives disclosed herein may be synthesized. If a Lewis acid is used to promote the glycosylation, the corresponding C-glycosides can also be prepared by following literature conditions (see: Ref: (1) T. Matsumoto, M. Katsuki, and K. Suzuki, Tetrahedron Lett., 29, 6935-6938 (1988); (2) Y. Li, G. Wei, B. Yu, Carbohydr. Res., 341, 2717-2722). The amount of aldehyde/ketone used in the final reductive amination step can be controlled to allow mono- or di-alkylation. Instead of using reductive amination, the amine functionality can also be N-alkylated using an appropriate alkylating reagent such as an alkyl halides, alkyl p-tosylate/mesylate/triflate or / conjugated reagents to afford higher substituted amines or quaternary ammonium salts. Multiple N-alkylations can be carried out in one-pot or stepwise manner using the same or different alkyl halides. The amine functionality can also be N-acylated using an appropriate acylating reagent such as an acid anhydride or acyl halide. Thus, in addition to 4-hydroxy-psilocybin shown in FIG. 3B, the example glycosylated psilocybin derivatives shown in FIGS. 4A, 4C, 4D and 4E, respectively may be formed using different hydroxylated indoles as a starting material.

In general, the reactants are reacted under reaction conditions which permit the reactants to chemically react with each other and form a product, i.e. the glycosylated psilocybin derivatives of the present disclosure. Such reactions conditions may be selected, adjusted and optimized as known by those of skill in the art. Thus, for example, as is known to those of skill in the art, it is noted that the reaction may be catalyzed by initially preparing a glycosyl derivative compound to enhance the reactivity between the glycosyl compound and the hydroxy-containing psilocybin derivative. Thus, for example, the anomeric carbon of the glycosyl compound may be complexed with a halogen, such as bromide and chloride, and furthermore the reaction may be performed in the presence of, for example, $Ag_2CO_3$ or another heavy metal based compound, which can act as an acid (HCl or HBr) scavenger. Other glycosyl compound derivatives that may be used include acylate (such as acetate), imidate (such as trichloroacetimidate), thioalkyl or thioaryl of glycosyl compound derivatives.

The reactions may be conducted in any suitable reaction vessel (e.g. a tube, bottle). Suitable solvents that may be used are polar solvents such as, for example, dichloromethane, dichloroethane, toluene, and so called participating solvents such as acetonitrile and diethyl ether. Suitable temperatures may range from, for example, e.g. from about −78° C. to about 60° C. Furthermore, catalysts, also known as promoters, may be included in the reaction such as iodonium dicollidine perchlorate (IDCP), any silver or mercury salts, trimethylsilyl trifluoromethanesulfonate (TMS-triflate, TMSOTf), or trifluoronmethanesulfonic acid (triflic acid, TfOH), N-iodosuccinimide, methyl triflate. Furthermore, reaction times may be varied. As will readily be appreciated by those of skill in the art, the reaction conditions may be optimized, for example by preparing several glycosyl compound preparations and hydroxy-containing psilocybin derivative preparations and reacting these in different reaction vessels under different reaction conditions, for example, different temperatures, using different solvents etc., evaluating the obtained glycosylated psilocybin derivative reaction product, adjusting reaction conditions, and selecting a desired reaction condition. Further general guidance regarding appropriate reaction conditions for performing glycosylation reactions may be found in Demchenko, A., handbook of chemical glycosylation: advances in stereoselectivity and therapeutic relevance, 2008, Wiley-VCH Verlag GmbH.

Figure 10:
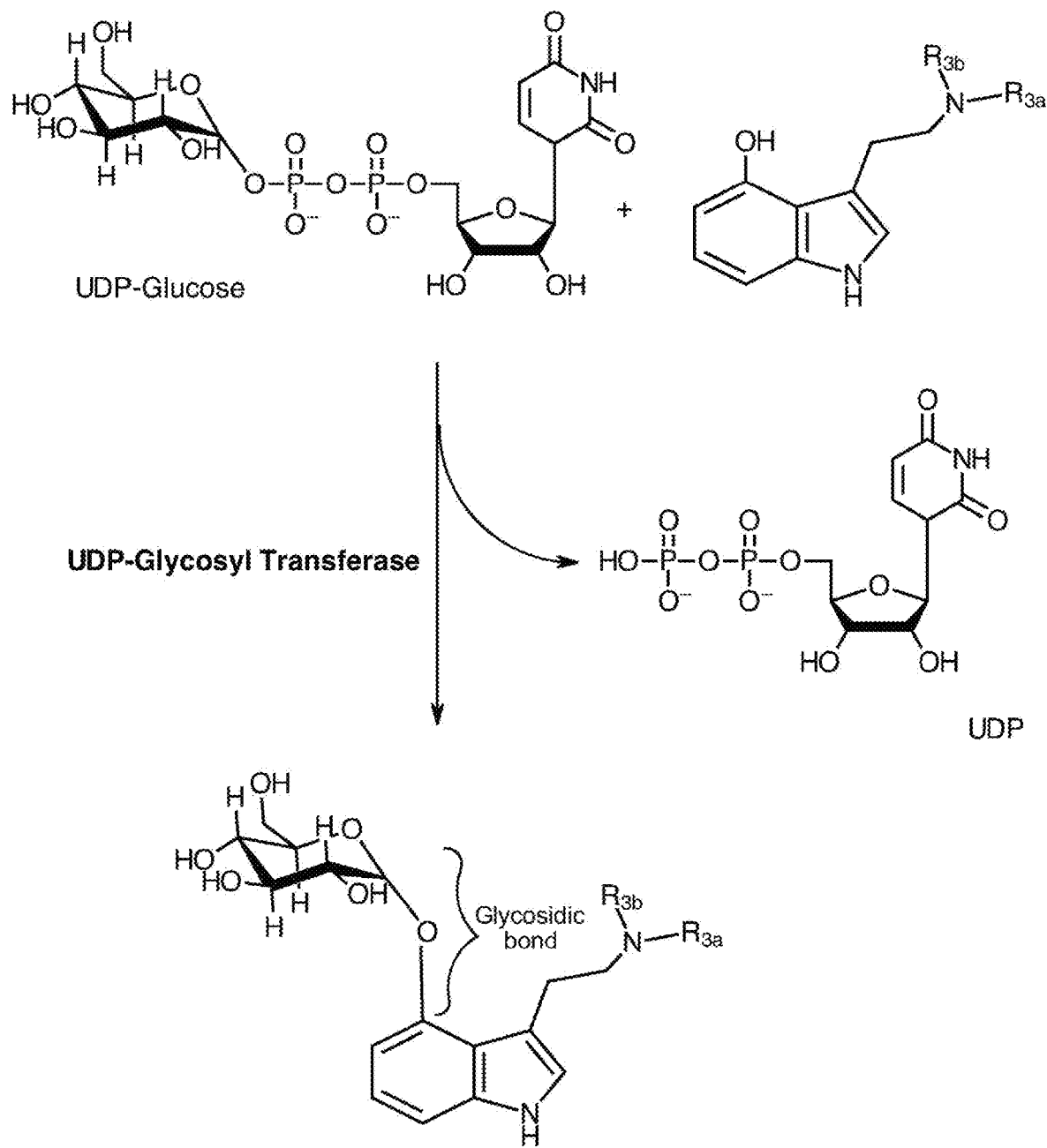
FIG. 10 depicts an example biochemical reaction for synthesizing a glycosylated psilocybin derivative, notably a 4-hydroxy-psilocybin derivative is reacted with a UDP-glucose to form a 4-glucose-psilocybin derivative.

In one example embodiment, the reaction may be catalyzed by a glucosyl transferase. Referring now to FIG. 10, shown therein is an example chemical reaction catalyzed by a UDP glycosyl transferase wherein the glucose moiety of UDP-glucose is transferred to a 4-hydroxy-psilocybin derivative in a chemical reaction which results in the formation of a glycosidic bond, and which is catalyzed by a UDP glycosyl transferase. Thus, it will be clear that in one embodiment, the glycosylated psilocybin derivative can be formed in a reaction between a UDP-glycosyl compound and a hydroxy-containing psilocybin derivative, wherein the hydroxy group reacts with the glycosyl group of the UDP-glycosyl compound to form a glycosidic bond, and wherein the reaction is catalyzed by the UDP-glycosyl transferase.

The reaction shown in FIG. 10 can be carried out in vitro. Thus, the reaction constituents, i.e. a hydroxy-containing psilocybin derivative, a glycosyl compound, and a glycosyl transferase can be contacted and reacted in vitro, for example, in a tube, bottle, or dish, or other suitable reaction vessel. Suitable in vitro reaction conditions are generally reaction conditions which are approximately physiological conditions. In general, in vitro physiological conditions can comprise, for example, 50-200 mM NaCl or KCl, pH 6.5-8.5, 20-45° C., or 30-40° C. and 0.001-10 mM divalent cation (e.g., $Mg^{++}$, $Ca^{++}$); preferably about 150 mM NaCl or KCl, pH 7.2-7.6, 5 mM divalent cation, and often include 0.01-1.0 percent nonspecific protein (e.g., BSA). Furthermore a non-ionic detergent (Tween, NP-40, Triton X-100) can often be present, usually at about 0.001 to 2%, typically 0,05-0.2% (v/v). Particular aqueous conditions may be selected by the practitioner according to conventional methods. For general guidance, the following buffered aqueous conditions may be applicable: 10-250 mM NaCl, 5-50 mM Tris HCl, pH 5-8, with optional addition of divalent cation(s) and/or metal chelators and/or non-ionic detergents and/or membrane fractions and/or anti-foam agents and/or scintillants. All reaction constituents may be mixed, for example by gentle stirring or shaking the reaction vessel. Reaction times may vary, but generally the glycosylated psilocybin compound can be formed in less than about 30 minutes, for examples less than about 20 minutes, or less than about 5 minutes. Furthermore those of skill in the art will be able to modulate or optimize reaction conditions, for example, by preparing multiple reaction vessels, performing the in vitro reaction under multiple reaction conditions and evaluating the formation of glycosylated psilocybin compound under these different reaction conditions. Subsequently a desired reaction condition may be selected.

In one embodiment of the present disclosure the glycosylated psilocybin derivatives may be formed biosynthetically. Accordingly, the present disclosure further includes in one embodiment, a method of making a glycosylated psilocybin derivative the method comprising:

(a) contacting a hydroxy-containing psilocybin derivative compound with a host cell comprising a glycosyl transferase, wherein the hydroxy-containing psilocybin derivative compound or salt thereof has the chemical formula (II):

(II)

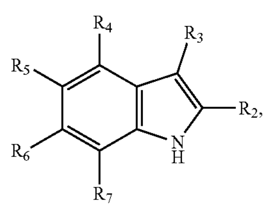

wherein at least one of $R_2$, Ra, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein $R_3$ is a hydrogen atom, a 2-aminoethyl group, or an N-substituted 2-aminoethyl amino group, wherein $R_4$ when it is not hydroxylated is a hydrogen atom, an alkyl group or O-alkyl group or a phosphate group, and (b) growing the host cell to produce a glycosylated psilocybin derivative compound or salt thereof having formula (I):

(I)

wherein at least one of $R_2$, $R_4$, $R_5$, $R_6$, or $R_7$ is a glycosyl group, and wherein each non-glycosylated $R_2$, $R_5$, $R_6$, or $R_7$ is a hydrogen atom or an alkyl group or O-alkyl group, wherein $R_4$ when it is not glycosylated is a hydrogen atom, an alkyl group or O-alkyl group or a phosphate group, and wherein $R_{3A}$ and $R_{3B}$ are a hydrogen atom, an alkyl group, an aryl group, an acyl group.

Implementation of the foregoing example embodiment initially involves providing hydroxy-containing psilocybin precursor compounds and host cells comprising a glycosyl transferase. Accordingly, next, exemplary hydroxy-containing psilocybin compounds and example host cells that may be selected and used in accordance with the present disclosure will be described. Thereafter, example methodologies and techniques will be described to contact and use the hydroxy-containing psilocybin precursor compounds and cells to produce example glycosylated psilocybin compounds.

In general any hydroxy-containing compounds of the formula (II) may be used including any and all of the hereinbefore described hydroxy compounds, such as, for example the compounds shown in FIGS. 3A-3E.

Turning now to the host cells that can be used in accordance with the present disclosure, it is initially noted that a variety of host cells may be selected in accordance with the present disclosure, including microorganism host cells, plant host cells, and animal host cells.

In accordance herewith the host cell include a glycosyl transferase. Such cells can be obtained in at least two ways. First, in some embodiments, host cells may be selected in which a glycosyl transferase is naturally present. Second, in some embodiments, a host cell that not naturally produces a suitable glycosyl transferase may modulated to produce a glycosyl transferase. Thus, for example, a nucleic acid sequence encoding a glycosyl transferase may be introduced into a host cell, and upon cell growth the host cells can make the glycosyl transferase.

Typically, a nucleic acid sequence encoding a glycosyl transferase further includes one or more additional nucleic acid sequences, for example, a nucleic acid sequences controlling expression of the glycosyl transferase, and these one or more additional nucleic acid sequences together with the nucleic acid sequence encoding the glycosyl transferase can be said to form a chimeric nucleic acid sequence.

A host cell which upon cultivation expresses the chimeric nucleic acid can be selected and used in accordance with the present disclosure. Suitable host cells in this respect include, for example, microbial cells, such as bacterial cells, yeast cells, for example, and algal cells or plant cells. A variety of techniques and methodologies to manipulate host cells to introduce nucleic acid sequences in cells and attain expression exists and are well known to the skilled artisan. These methods include, for example, cation based methods, for example, lithium ion or calcium ion based methods, electroporation, biolistics, and glass beads based methods. As will be known to those of skill in the art, depending on the host cell selected, the methodology to introduce nucleic acid material in the host cell may vary, and, furthermore, methodologies may be optimized for uptake of nucleic acid material by the host cell, for example, by comparing uptake of nucleic acid material using different conditions. Detailed guidance can be found, for example, in Sambrook et al., Molecular Cloning, a Laboratory Manual, Cold Spring Harbor Laboratory Press, 2012, Fourth Ed. It is noted that the chimeric nucleic acid is a non-naturally occurring chimeric nucleic acid sequence and can be said to be heterologous to the host cell.

In some embodiments, the glycosyl transferase can be selected a nucleic acid sequence selected from the nucleic acid sequences consisting of:
(a) SEQ.ID NO: 1, SEQ.ID NO: 3, SEQ.ID NO: 5, SEQ.ID NO: 7, and SEQ.ID NO: 9;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 2, SEQ.ID NO: 4, SEQ.ID NO: 6, SEQ.ID NO: 8, and SEQ.ID NO: 10;
(f) a nucleic acid sequence that encodes a functional variant of any one of the amino acid sequences set forth in SEQ.ID NO: 2, SEQ.ID NO: 4, SEQ.ID NO: 6, SEQ.ID NO: 8, and SEQ.ID NO: 10; and
(g) a nucleic acid sequence that hybridizes under stringent conditions to any one of the nucleic acid sequences set forth in (a), (b), (c), (d), (e) or (f).

Thus any of the nucleic acid sequences set forth in (a), (b), (c), (d), (e), (f) or (g) may be selected and introduced into a host cell.

One example host cell that conveniently may be used is *Escherichia coli*. The preparation of the *E. coli* vectors may be accomplished using commonly known techniques such as restriction digestion, ligation, gel electrophoresis, DNA sequencing, the polymerase chain reaction (PCR) and other methodologies. A wide variety of cloning vectors is available to perform the necessary steps required to prepare a recombinant expression vector. Among the vectors with a replication system functional in *E. coli*, are vectors such as pBR322, the pUC series of vectors, the M13 mp series of vectors, pBluescript etc. Suitable promoter sequences for use in *E. coli* include, for example, the T7 promoter, the T5 promoter, tryptophan (trp) promoter, lactose (lac) promoter, tryptophan/lactose (tac) promoter, lipoprotein (lpp) promoter, and λ phage PL promoter. Typically, cloning vectors contain a marker, for example, an antibiotic resistance marker, such as ampicillin or kanamycin resistance marker, allowing selection of transformed cells. Nucleic acid sequences may be introduced in these vectors, and the vectors may be introduced in *E. coli* by preparing competent cells, electroporation or using other well known methodologies to a person of skill in the art. *E. coli* may be grown in an appropriate medium, such as Luria-Broth medium and harvested. Recombinant expression vectors may readily be recovered from cells upon harvesting and lysing of the cells.

Another example host cell that may be conveniently used is a yeast cell. Example yeast host cells that can be used are yeast cells belonging to the genus *Candida, Kiuyverornyces, Saccharomyces, Schizosaccharomyces, Pichia, Hansenula*, and *Yarrowia*. In specific example embodiments, the yeast cell can be a *Saccharomyces cerevisiae* cell, a *Yarrowia lipolytica* cell, or *Pichia pastoris* cell.

A number of vectors exist for the expression of recombinant proteins in yeast host cells. Examples of vectors that may be used in yeast host cells include, for example, Yip type vectors, YEp type vectors, YRp type vectors, YCp type vectors, pGPD-2, pAO815, pGAPZ, pGAPZα, pHIL-D2, pHIL-S1, pPIC3.5K, pPIC9K, pPICZ, pPICZα, pPIC3K, pHWO10, pPUZZLE and 2 μm plasmids. Such vectors are known to the art and are, for example, described in Gregg et al., Mol Biotechnol. (2000) 16(1): 23-52. Suitable promoter sequences for use in yeast host cells are also known and described, for example, in Mattanovich et al., Methods Mot Biol., 2012, 824:329-58, and in Romanos et al., 1992, Yeast 8: 423-488. Examples of suitable promoters for use in yeast host cells include promoters of glycolytic, enzymes, like triosephosphate isomerase (TPI), phosphoglycerate Kinase (PGK), glyceraldehyde-3-phosphate dehydrogenase (GAPDH or GAP) and variants thereof, lactase (LAC) and galactosidase (GAL), *P. pastoris* glucose-6-phosphate isomerase promoter (PPG), the 3-phosphoglycerate kinase promoter (PP K), the glycerol aldehyde phosphate dehydrogenase promoter (PGAP), translation elongation factor promoter (PTEF), *S. cerevisiae* enolase (ENO-1), *S cerevisiae* galactokinase (GAL1), *S. cerevisiae* alcohol dehydrogenase/glyceraldehyde-3-phosphate dehydrogenase (ADH1, ADH2/GAP), *S. cerevisiae* triose phosphate isomerase (TPI), *S. cerevisiae* metallothionein (CUP1), and *S. cerevisiae* 3-phosphoglycerate kinase (PGK), and the maltase gene promoter (MAL), Marker genes suitable for use in yeast host cells are also known to the art. Thus, antibiotic resistance markers, such as ampicillin resistance markers, can be used in yeast, as well as marker genes providing genetic functions for essential nutrients, for example, leucine (LEU2), tryptophan (TRP1 and TRP2), uracil (URA3, URA5, URA6), histidine (HIS3), and the like. Methods for introducing vectors into yeast host cells can, for example, be found in S. Kawai et al., 2010, Bioeng. Bugs 1(6): 395-403.

Further, guidance with respect to the preparation of expression vectors and introduction thereof into host cells, including in *E. coli* cells, yeast cells, and other host cells, may be found in, for example: Sambrook et al., Molecular Cloning, a Laboratory Manual, Cold Spring Harbor Laboratory Press, 2012, Fourth Ed.

Thus, to briefly recap, a host cell comprising a chimeric nucleic acid comprising (i) a nucleic acid sequence controlling expression in a host cell and (ii) a nucleic acid sequence encoding a glycosyl transferase, can be prepared in accordance with the present disclosure.

In accordance herewith, host cells are grown to multiply and to express a chimeric nucleic acid. Expression of the chimeric nucleic acid results in the biosynthetic production in the host cell of a glycosyl transferase. Growth media and growth conditions can vary depending on the host cell that is selected, as will be readily appreciated to those of ordinary skill in the art. Growth media typically contain a carbon source, one or several nitrogen sources, essential salts including salts of potassium, sodium, magnesium, phosphate and sulphate, trace metals, water soluble vitamins, and process aids including but not limited to antifoam agents, protease inhibitors, stabilizers, ligands and inducers. Example carbon sources are e.g. mono- or disaccharides. Example nitrogen sources are, e.g. ammonia, urea, amino adds, yeast extract, corn steep liquor and fully or partially hydrolyzed proteins. Example trace metals are e.g., Fe, Zn, Mn, Cu, Mo and $H_3BO_3$. Example water soluble vitamins are e.g. biotin, pantothenate, niacin, thiamine, p-aminobenzoic acid, choline, pyridoxine, folic add, riboflavin and ascorbic add. Further, specific example media include liquid culture media for the growth of yeast cells and bacterial cells including, Luria-Bertani (LB) broth for bacterial cell cultivation, and yeast extract peptone dextrose (YEPD or YPD), for yeast cell cultivation. Further media and growth conditions can be found in Sambrook et al., Molecular Cloning, a Laboratory Manual, Cold Spring Harbor Laboratory Press, 2012, Fourth Ed.

In order for the host cells to produce the glycosylated psilocybin, the cells are provided with a hydroxyl-containing psilocybin derivative. Thus, in accordance herewith, host cells may be contacted with a hydroxyl-containing psilocybin derivative. The psilocybin precursor compound can be exogenously supplied, for example, by including a hydroxyl-containing psilocybin derivative in the growth medium of the host cells, and growing the host cells in a medium including the hydroxyl-containing psilocybin derivative.

Upon production by the host cells of the glycosylated psilocybin compounds in accordance with the methods of the present disclosure, the glycosylated psilocybin compounds may be extracted from the host cell suspension, and separated from other constituents within the host cell suspension, such as media constituents and cellular debris. Separation techniques will be known to those of skill in the art and include, for example, solvent extraction (e.g. butane, chloroform, ethanol), column chromatography based techniques, high-performance liquid chromatography (HPLC), for example, and/or countercurrent separation (CCS) based systems. The recovered glycosylated psilocybin compounds may be obtained in a more or less pure form, for example, a preparation of glycosylated psilocybin compounds of at least about 60% (w/v), about 70% (w/v), about 80% (w/v), about 90% (w/v), about 95% (w/v) or about 99% (w/v) purity may be obtained. Thus, in this manner, glycosylated psilocybin derivatives in more or less pure form may be prepared.

It will now be clear form the foregoing that novel glycosylated psilocybin derivatives are disclosed herein, as well as methods of making glycosylated psilocybin derivatives. The glycosylated psilocybin compounds may be formulated for use as a pharmaceutical drug or recreational drug.

Summary of Sequences

SEQ.ID NO: 1 sets forth a human nucleic acid sequence encoding a human glycosyl transferase polypeptide.

SEQ.ID NO: 2 sets forth a deduced amino acid sequence of a human glycosyl transferase polypeptide.

SEQ.ID NO: 3 sets forth a human nucleic acid sequence encoding another glycosyl transferase polypeptide.

SEQ.ID NO: 4 sets forth a deduced amino acid sequence of another human glycosyl transferase polypeptide.

SEQ.ID NO: 5 sets forth a human nucleic acid sequence encoding another glycosyl transferase polypeptide.

SEQ.ID NO: 6 sets forth a deduced amino acid sequence of another human glycosyl transferase polypeptide.

SEQ.ID NO: 7 sets forth a human nucleic acid sequence encoding another glycosyl transferase polypeptide.

SEQ.ID NO: 8 sets forth a deduced amino acid sequence of another human glycosyl transferase polypeptide.

SEQ.ID NO: 9 sets forth a human nucleic acid sequence encoding another glycosyl transferase polypeptide.

SEQ.ID NO: 10 sets forth a deduced amino acid sequence of another human glycosyl transferase polypeptide.

```
                                                     SEQUENCE LISTING
                                                                                                SEQ. ID NO: 1
ATGGCTCGCGCAGGGTGGACCAGCCCCGTTCCTTTATGTGTGTGTCTACTGCTGACCTGTGGCTTTGCCGAGG
CAGGGAAGCTGCTGGTAGTGCCCATGGATGGGAGTCACTGGTTCACCATGCAGTCGGTGGTGGAGAAACTTAT
CCTCAGGGGGCATGAGGTGGTTGTAGTCATGCCAGAGGTGAGTTGGCAACTGGAAAGATCACTGAATTGCACA
GTGAAGACTTACTCAACCTCGTACACTCTGGAAGATCAGAACCGGGAATTCATGGTTTTCGCCCATGCTCAAT
GGAAAGCACAGGCACAAAGTATATTTTCTCTATTAATGAGTTCATCCAGTGGTTTTCTTGACTTATTTTTTC
GCATTGCAGGAGTTTGTTTAATGACCGAAAATTAGTAGAATACTTAAAGGAGAGTTCTTTTGATGCAGTGTTT
CTGGATCCTTTTGATACCTGTGGCTTAATTGTTGCTAAATATTTCTCCCTCCCCTCTGTGGTCTTCACCAGGG
GAATATTTTGCCACCATCTTGAAGAAGGTGCACAGTGCCCTGCTCCTCTTTCCTATGTCCCCAATGATCTCTT
AGGGTTCTCAGATGCCATGACTTTCAAGGAGAGATGTGAACCACATCGTGCACTTGGAGGACCATTTATTT
TGCCAGTATCTTTTTAGAAATGCCCTAGAAATAGCCTCTGAAATTCTCCAAACCCCTGTCACGGCATATGATC
TCTACAGTCACACATCAATTTGGTTGTTGCGAACGGACTTTGTTTTGGACTATCCCAAACCCGTGATGCCCAA
CATGATCTTCATTGGTGGTATCAACTGTCATCAGGGAAAGCCATTGCCTATGGAATTTGAAGCCTACATTAAT
GCTTCTGGAGAACATGGAATTGTGGTTTTCTCTTTGGGATCAATGGTCTCAGAAATTCCAGAGAAGAAAGCTA
TGGCAATTGCTGATGCTTTGGGCAAAATCCCTCAGACAGTCCTGTGGCGGTACACTGGAACCCGACCATCGAA
TCTTGCGAACAACACGATACTTGTTAAGTGGCTACCCCAAAACGATCTGCTTGGTCACCCGATGACCCGTGCC
TTTATCACCCATGCTGGTTCCCATGGTGTTTATGAAAGCATATGCAATGGCGTTCCCATGGTGATGATGCCCT
TGTTTGGTGATCAGATGGACAATGCAAAGCGCATGGAGACTAAGGGAGCTGGAGTGACCCTGAATGTTCTGGA
AATGACTTCTGAAGATTTAGAAAATGCTCTAAAAGCAGTCATCAATGACAAAAGTTACAAGGAGAACATCATG
CGCCTCTCCAGCCTTCACAAGGACCGCCCGGTGGAGCCGCTGGACCTGGCCGTGTTCTGGGTGGAGTTTGTGA
TGAGGCACAAGGGCGCGCCACACCTGCGCCCCGCAGCCCACGACCTCACCTGGTACCAGTACCATTCCTTGGA
CGTGATTGGTTTCCTCTTGGCCGTCGTGCTGACAGTGGCCTTCATCACCTTTAAATGTTGTGCTTATGGCTAC
CGGAAATGCTTGGGGAAAAAAGGGCGAGTTAAGAAAGCCCACAAATCCAAGACCCATTGA

SEQ. ID NO: 2
MARAGWTSPVPLCVCLLLTCGFAEAGKLLVVPMDGSHWFTMQSVVEKLILRGHEVVVVMPEVSWQLERSLNCT
VKTYSTSYTLEDQNREFMVFAHAQWKAQAQSIFSLLMSSSSGFLDLFFSHCRSLFNDRKLVEYLKESSFDAVF
LDPFDTCGLIVAKYFSLPSVVFTRGIFCHHLEEGAQCPAPLSYVPNDLLGFSDAMTFKERVWNHIVHLEDHLF
CQYLFRNALEIASEILQTPVTAYDLYSHTSIWLLRTDFVLDYPKPVMPNMIFIGGINCHQGKPLPMEFEAYIN
ASGEHGIVVFSLGSMVSEIPEKKAMAIADALGKIPQTVLWRYTGTRPSNLANNTILVKWLPQNDLLGHPMTRA
FITHAGSHGVYESICNGVPMVMMPLFGDQMDNAKRMETKGAGVTLNVLEMTSEDLENALKAVINDKSYKENIM
RLSSLHKDRPVEPLDLAVFWVEFVMRHKGAPHLRPAAHDLTWYQYHSLDVIGFLLAVVLTVAFITFKCCAYGY
RKCLGKKGRVKKAHKSKTH

SEQ. ID NO: 3
ATGGCTTGCACAGGGTGGACCAGCcCcCTTCCTCTATGTGTGTGTCTGCTGCTGACCTGTGGCTTTGCCGAGG
CAGGGAAGCTACTGGTAGTGCCCATGGATGGGAGCCACTGGTTCACCATGAGGTCGGTGGTGGAGAAACTCAT
TCTCAGGGGGCATGAGGTGGTTGTAGTCATGCCAGAGGTGAGTTGGCAACTGGGAAGATCACTGAATTGCACA
GTGAAGACTTATTCAACTTCATATACCCTGGAGGATCTGGACCGGGAGTTCAAGGCTTTTGCCCATGCTCAAT
GGAAAGCACAAGTACGAAGTATATATTCTCTATTAATGGGTTCATACAATGACATTTTTGACTTATTTTTTC
AAATTGCAGGAGTTTGTTTAAAGACAAAAAATTAGTAGAATACTTAAAGGAGAGTTCTTTTGATGCAGTGTTT
CTCGATCCTTTTGATAACTGTGGCTTAATTGTTGCCAAATATTTCTCCCTCCCCTCCGTGGTCTTCGCCAGGG
```

```
                         SEQUENCE LISTING

GAATACTTTGCCACTATCTTGAAGAAGGTGCACAGTGCCCTGCTCCTCTTTCCTATGTCCCCAGAATTCTCTT
AGGGTTCTCAGATGCCATGACTTTCAAGGAGAGAGTACGGAACCACATCATGCACTTGGAGGAACATTTATTA
TGCCACCGTTTTTTCAAAAATGCCCTAGAAATAGCCTCTGAAATTCTCCAAACACCTGTTACGGAGTATGATC
TCTACAGCCACACATCAATTTGGTTGTTGCGAACGGACTTTGTTTTGGACTATCCCAAACCCGTGATGCCCAA
CATGATCTTCATTGGTGGTATCAACTGCCATCAGGGAAAGCCGTTGCCTATGGAATTTGAAGCCTACATTAAT
GCTTCTGGAGAACATGGAATTGTGGTTTTCTCTTTGGGATCAATGGTCTCAGAAATTCCAGAGAAGAAAGCTA
TGGCAATTGCTGATGCTTTGGGCAAAATCCCTCAGACAGTCCTGTGGCGGTACACTGGAACCCGACCATCGAA
TCTTGCGAACAACACGATACTTGTTAAGTGGCTACCCCAAAACGATCTGCTTGGTCACCCGATGACCCGTGCC
TTTATCACCCATGCTGGTTCCCATGGTGTTTATGAAAGCATATGCAATGGCGTTCCCATGGTGATGATGCCCT
TGTTTGGTGATCAGATGGACAATGCAAAGCGCATGGAGACTAAGGGAGCTGGAGTGACCCTGAATGTTCTGGA
AATGACTTCTGAAGATTTAGAAATGCTCTAAAAGCAGTCATCAATGACAAAAGTTACAAGGAGAACATCATG
CGCCTCTCCAGCCTTCACAAGGACCGCCCGGTGGAGCCGCTGGACCTGGCCGTGTTCTGGGTGGAGTTTGTGA
TGAGGCACAAGGGCGCGCCACACCTGCGCCCCGCAGCCCACGACCTCACCTGGTACCAGTACCATTCCTTGGA
CGTGATTGGTTTCCTCTTGGCCGTCGTGCTGACAGTGGCCTTCATCACCTTTAAGTTGTGCTTATGGCTAC
CGGAAATGCTTGGGGAAAAAAGGGCGAGTTAAGAAAGCCCACAAATCCAAGACCCATTGA

SEQ. ID NO: 4
MACTGWTSPLPLCVCLLLTCGFAEAGKLLVVPMDGSHWFTMRSVVEKLILRGHEVVVVMPEVSWQLGRSLNCT
VKTYSTSYTLEDLDREFKAFAHAQWKAQVRSIYSLLMGSYNDIFDLFFSNCRSLFKDKKLVEYLKESSFDAVF
LDPFDNCGLIVAKYFSLPSVVFARGILCHYLEEGAOCPAPLSYVPRILLGFSDAMTFKERVRNHIMHLEEHLL
CHRFFKNALEIASEILQTPVTEYDLYSHTSTWLLRTDFVLDYPKPVMPNMIFIGGINCHQGKPLPMEFEAYIN
ASGEHGIVVFSLGSMVSEIPEKKAMAIADALGKIPQTVLWRYTGTRPSNLANNTILVKWLPQNDLLGHPMTRA
FITHAGSHGVYESICNGVPMVMMPLFGDOMDNAKRMETKGAGVTLNVLEMTSECLENALKAVINDKSYKENIM
RLSSLHKDRPVEPLDLAVFWVEFVMRHKGAPHLRPAAHDLTWYQYHSLDVIGFLLAVVLTVAFITFKCCAYGY
RKCLGKKGRVKKAHKSKTH

SEQ. ID NO: 5
ATGGCTCGCACAGGGTGGACCAGCCCCATTCCCCTATGTGTTTCTCTGCTGCTGACCTGTGGCTTTGCTGAGG
CAGGGAAGCTGCTGGTAGTGCCCATGGATGGGAGTCACTGGTTCACCATGCAGTCGGTGGTGGAGAAACTTAT
CCTCAGGGGCATGAGGTGGTTGTAGTCATGCCAGAGGTGAGTTGGCAACTGGGAAAATCACTGAATTGCACA
GTGAAGACTTACTCAACCTCATACACTCTGGAGGATCTGGACCGGGAATTCATGGATTTCGCCGATGCTCAAT
GGAAAGCACAAGTACGAAGTTTGTTTTCTCTATTTCTGAGTTCATCCAATGGTTTTTTTAACTTATTTTTTC
GCATTGCAGGAGTTTGTTTAATGACCGAAATTAGTAGAATACTTAAAGGAGAGTTCTTTTGATGCGGTGTTT
CTTGATCCTTTTGATGCCTGTGGCTTAATTGTTGCCAAATATTTCTCCCTCCCCTCTGTGGTCTTCGCCAGGG
GAATAGCTTGCCACTATCTTGAAGAAGGTGCACAGTGCCCTGCTCCTCTTTCCTATGTCCCCAGAATTCTCTT
AGGGTTCTCAGATGCCATGACTTTCAAGGAGAGAGTACGGAACCACATCATGCACTTGGAGGAACATTTATTT
TGCCAGTATTTTTCCAAAAATGCCCTAGAAATAGCCTCTGAAATTCTCCAAACACCTGTCACAGCATATGATC
TCTACAGCCACACATCAATTTGGTTGTTGCGAACAGACTTTGTTTTGGACTATCCCAAACCCGTGATGCCCAA
TATGATCTTCATTGGTGGTATCAACTGCCATCAGGGAAAGCCATTGCCTATGGAATTTGAAGCCTACATTAAT
GCTTCTGGAGAACATGGAATTGTGGTTTTCTCTTTGGGATCAATGGTCTCAGAAATTCCAGAGAAGAAAGCTA
TGGCAATTGCTGATGCTTTGGGCAAAATCCCTCAGACAGTCCTGTGGCGGTACACTGGAACCCGACCATCGAA
TCTTGCGAACAACACGATACTTGTTAAGTGGCTACCCCAAAACGATCTGCTTGGTCACCCGATGACCCGTGCC
TTTATCACCCATGCTGGTTCCCATGGTGTTTATGAAAGCATATGCAATGGCGTTCCCATGGTGATGATGCCCT
TGTTTGGTGATCAGATGGACAATGCAAAGCGCATGGAGACTAAGGGAGCTGGAGTGACCCTGAATGTTCTGGA
AATGACTTCTGAAGATTTAGAAATGCTCTAAAAGCAGTCATCAATGACAAAAGTTACAAGGAGAACATCATG
CGCCTCTCCAGCCTTCACAAGGACCGCCCGGTGGAGCCGCTGGACCTGGCCGTGTTCTGGGTGGAGTTTGTGA
TGAGGCACAAGGGCGCGCCACACCTGCGCCCCGCAGCCCACGACCTCACCTGGTACCAGTACCATTCCTTGGA
CGTGATTGGTTTCCTCTTGGCCGTCGTGCTGACAGTGGCCTTCATCACCTTTAAGTTGTGCTTATGGCTAC
CGGAAATGCTTGGGGAAAAAAGGGCGAGTTAAGAAAGCCCACAAATCCAAGACCCATTGA

SEQ. ID NO: 6
MAKTGWTSPLPLCVSLLLTCGFAEAGKLLVVPMDGSHWETMQSVVEKLLLRGHEVVVVMPEVSWQLGKSLNCT
VKTYSTSYTLEDLDREFMDFADAQWKAQVRSLFSLFLSSSNGFFNLFFSHCRSLFNDRKLVEYLKESSFDAVF
LDPFDACGLIVAKYFSLPSVVFARGIACHYIEEGAQCPAPLSYVPRILLGFSDAMTFKERVRNHIMHLEEHLF
CQYFSKNALEIASEILQTPVTAYDLYSHTSIWLLRTDFVLDYPKPVMPNMIFIGGINCHQGKPLPMEFEAYIN
ASGEHGIVVFSLGSMVSEIPEKKAMAIADALGKIPQTVLWRYTGTRPSNLANNTILVKWLPQNDLLGHPMTRA
FTTHAGSHGVYESICNGVPMVMMPIFGDOMDNAKRMETKGAGVTLNVIEMTSEDLENALKAVTNDKSYKENIM
RLSSLHKDRPVEPLDLAVFWVEFVMRHKGAPHLRPAAHDLTWYQYHSLDVIGFLLAWLTVAFITFKCCAYGR
KCLGKKGRVKKAHKSKTH

SEQ. ID NO: 7
ATGGCTCGTGCAGGGTGGACTGGCCTCCTTCCCCTATATGTGTGTCTACTGCTGACCTGTGGCTTTGCCAAGG
CAGGGAAGCTGCTGGTAGTGCCCATGGATGGGAGCCACTGGTTCACCATGCAGTCGGTGGTGGAGAAACTCAT
CCTCAGGGGGCATGAGGTGGTCGTAGTCATGCCAGAGGTGAGTTGGCAACTGGGAAGATCACTGAATTGCACA
GTGAAGACTTACTCAACCTCATACACTCTGGAGGATCAGGACCGGGAGTTCATGGTTTTTGCCGATGCTCGCT
GGACGGCACCATTGCGAAGTGCATTTCTCTATTAACAAGTTCATCCAATGGTATTTTTGACTTATTTTTTTC
AAATTGCAGGAGTTTGTTTAATGACCGAAATTAGTAGAATACTTAAAGGAGAGTTGTTTTGATGCAGTGTTT
CTCGATCCTTTTGATGCCTGTGGCTTAATTGTTGCCAAATATTTCTCCCTCCCCTCTGTGGTCTTCGCCAGGG
GAATATTTTGCCACTATCTTGAAGAAGGTGCACAGTGCCCTGCTCCTCTTTCCTATGTCCCCAGACTTCTCTT
AGGGTTCTCAGACGCCATGACTTTCAAGGAGAGTATGAACCACATCATGCACTTGGAGGAACATTTATTT
TGCCCCTATTTTTTCAAAAATGTCTTAGAAATAGCCTCTGAAATTCTCCAAACCCCTGTCACGGCATATGATC
```

SEQUENCE LISTING

```
TCTACAGCCACACATCAATTTGGTTGTTGCGAACTGACTTTGTTTTGGAGTATCCCAAACCCGTGATGCCCAA
TATGATCTTCATTGGTGGTATCAACTGTCATCAGGGAAAGCCAGTGCCTATGGAATTTGAAGCCTACATTAAA
GCTTCTGGAGAACATGGAATTGTGGTTTTCTCTTTGGGATCAATGGTCTCAGAAATTCCAGAGAAGAAAGCTA
TGGCAATTGCTGATGCTTTGGGCAAAATCCCTCAGACAGTCCTGTGGCGGTACACTGGAACCCGACCATCGAA
TCTTGCGAACAACACGATACTTGTTAAGTGGCTACCCCAAAACGATCTGCTTGGTCACCCGATGACCCGTGCC
TTTATCACCCATGCTGGTTCCCATGGTGTTTATGAAAGCATATGCAATGGCGTTCCCATGGTGATGATGCCCT
TGTTTGGTGATCAGATGGAGAATGCAAAGCGCATGGAGACTAAGGGAGCTGGAGTGAGCGTGAATGTTCTGGA
AATGACTTCTGAAGATTTAGAAAATGCTCTAAAAGCAGTCATCAATGACAAAAGTTACAAGGAGAACATCATG
CGCCTCTCCAGCCTTCACAAGGACCGCCCGGTGGAGCCGCTGGACCTGGCCGTGTTCTGGGTGGAGTTTGTGA
TGAGGCACAAGGGCGCGCCACACCTGCGCCCCGCAGCCCACGACCTCACCTGGTACCAGTACCATTCCTTGGA
CGTGATTGGTTTCCTCTTGGCCGTCGTGCTGACAGTGGCCTTCATCACCTTTAAATGTTGTGCTTATGGCTAC
CGGAAATGCTTGGGGAAAAAAGGGCGAGTTAAGAAAGCCCACAAATCCAAGACCCATTGA
```

SEQ. ID NO: 8
```
MARAGWTGLLPLYVCLLLTCGFAKAGKLLVVPMDGSHWETMQSVVEKLILRGHEVVVVMPEVSWQLGRSLNCT
VKTYSTSYTLEDQDREFMVFADARWTAPLRSAFSLLTSSSNGIFDLFFSNCRSLFNDRKLVEYLKESCFDAVF
LDPFDACGLIVAKYFSLPSVVFARGIFCHYIEEGAQCPAPLSYVPRLLLGFSDAMTFKERVWNHIMHLEEHLF
CPYFFKNVLEIASEILQTPVTAYDLYSHTSIWLLRTDFVLEYPKPVMPNMIFIGGINCHQGKPVPMEFEAYIN
ASGEHGIVVFSLGSMVSEIPEKKAMAIADALGKIPQTVLWRYTGTRPSNLANNTILVKWLPQNDLLGHPMTRA
FTTHAGSHGVYESICNGVPMVMMPIFGDOMDNAKRMETKGAGVTLNVIEMTSEDLENALKAVTNDKSYKENIM
RLSSLHKDRPVEPLDLAVFWVEFVMRHKGAPHLRPAAHDLTWYQYHSLDVIGFLLAWLTVAFITFKCCAYGYR
KCLGKKGRVKKAHKSKTH
```

SEQ. ID NO: 9
```
ATGGCCTGCCTCCTTCGCTCATTTCAGAGAATTTCTGCAGGGGTTTTCTTCTTAGCACTTTGGGGCATGGTTG
TAGGTGACAAGCTGCTGGTGGTCCCTCAGGACGGAAGCCACTGGCTTAGTATGAAGGATATAGTTGAGGTTCT
CAGTGACCGGGGTCATGAGATTGTAGTGGTGGTGCCTGAAGTTAATTTGCTTTTGAAAGAATCCAAATACTAC
ACAAGAAAAATCTATCCAGTGCCGTATGACCAAGAAGAGCTGAAGAACCGTTACCAATCATTTGGAAACAATC
ACTTTGCTGAGCGATCATTCCTAACTGCTCCTCAGACAGAGTACAGGAATAACATGATTGTTATTGGCCTGTA
CTTCATCAACTGCCAGAGCCTCCTGCAGGACAGGGACACCCTGAACTTCTTTAAGGAGAGCAAGTTTGATGCT
CTTTTCACAGACCCAGCCTTACCCTGTGGGGTGATCCTGGCTGAGTATTTGGGCCTACCATCTGTGTACCTCT
TCAGGGGTTTTCCGTGTTCCCTGGAGCATACATTCAGCAGAAGCCCAGACCCTGTGTCCTACATTCCCAGGTG
CTACACAAAGTTTTCAGACCACATGACTTTTTCCCAACGAGTGGCCAACTTCCTTGTTAATTTGTTGGAGCCC
TATCTATTTTATTGTCTGTTTTCAAAGTATGAAGAACTCGCATCAGCTGTCCTCAAGAGAGATGTGGATATAA
TCACCTTATATCAGAAGGTCTCTGTTTGGCTGTTAAGATATGACTTTGTGCTTGAATATCCTAGGCCGGTCAT
GCCCAACATGGTCTTCATTGGAGGTATCAACTGTAAGAAGAGGAAAGACTTGTCTCAGGAATTTGAAGCCTAC
ATTAATGCTTCTGGAGAACATGGAATTGTGGTTTTCTCTTTGGGATCAATGGTCTCAGAAATTCCAGAGAAGA
AAGCTATGGCAATTGCTGATGCTTTGGGCAAAATCCCTCAGACAGTCCTGTGGCGGTACACTGGAACCCGACC
ATCGAATCTTGCGAACAACACGATACTTGTTAAGTGGCTACCCCAAAACGATCTGCTTGGTCACCCGATGACC
CGTGCCTTTATCACCCATGCTGGTTCCCATGGTGTTTATGAAAGCATATGCAATGGCGTTCCCATGGTGATGA
TGCCCTTGTTTGGTGATCAGATGGACAATGCAAAGCGCATGGAGACTAAGGGAGCTGGAGTGAGCCTGAATGT
TCTGGAAATGACTTCTGAAGATTTAGAAAATGCTCTAAAAGCAGTCATCAATGACAAAAGTTACAAGGAGAAC
ATCATGCGCCTCTCCAGCCTTCACAAGGACCGCCCGGTGGAGCCGCTGGACCTGGCCGTGTTCTGGGTGGAGT
TTGTGATGAGGCACAAGGGCGCGCCACACCTGCGCCCCGCAGCCCACGACCTCACCTGGTACCAGTACCATTC
CTTGGACGTGATTGGTTTCCTCTTGGCCGTCGTGCTGACAGTGGCCTTCATCACCTTTAAATGTTGTGCTTAT
GGCTACCGGAAATGCTTGGGGAAAAAAGGGCGAGTTAAGAAAGCCCACAAATCCAAGACCCATTGA
```

SEQ. ID NO: 10
```
MACLLRSFQRISAGVFFLALWGMVVGDKLLVVPQDGSHWLSMKDIVEVLSDRGHEIVVVVPEVNLLLKESKYY
TRKIYPVPYDQEELKNRYQSFGNNHFAERSFLTAPQTEYRNNMIVIGLYFINCQSLLQDRDTLNFFKESKFDA
LFTDPALPCGVILAEYLGLPSVYLFRGFPCSLEHTFSRSPDDPVSYIPRCYTKFSDHMTFSQRVANFLVNLLEP
YLFYCLFSKYEELASAVLKRDVDIITLYQKVSVWLLRYDFVLEYPRPVMPNMVFIGGINCKKRKDLSQEFEAY
INASGEHGIVVFSLGSMVSEIPEKKAMAIADALGKIPQTVLWRYTGTRPSNLANNTILVKWLPQNDLLGHPMT
RAFITHAGSHGVYESICNGVPMVMMPLFGDQMDNAKRMETKGAGVTLNVLEMTSEDLENALKAVINDKSYKEN
IMRLSSLHKDRPVEPLDLAVFWVEFVMRHKGAPHLRPAADLTWYQYHSLDVIGFLLAVVLTVAFITFKCCAYG
YRKCLGKKGRVKKAHKSKTH
```

Hereinafter are provided examples of specific implementations for performing the methods of the present disclosure, as well as implementations representing the compositions of the present disclosure. The examples are provided for illustrative purposes only, and are not intended to limit the scope of the present disclosure in any way.

EXAMPLES

Example 1—Processes for Making β-4-O-Glucosyl-Psilocybin Derivatives

This example refers to FIG. 11A and describes an example process for making β-4-O-glucosyl-psilocybin derivatives, notably compounds having the formula (III):

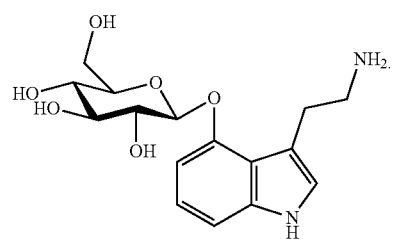

(III)

It is noted that in FIG. 11A, compound (III) corresponds with compound 11A-7.

A flame-dried round-bottom flask under argon atmosphere was charged with 4-hydroxy indole (11A-1) (5.00 g, 37.6 mmol, 1.00 eq), tetramethylammonium hydroxide pentahydrate (6.81 g, 37.6 mmol, 1.00 eq), and anhydrous DMF (100.0 mL). To aid dissolution, the stirring mixture was heated to for 15 minutes, yielding a dark-blue solution. Flame-activated 4 Å molecular sieves (5.00 g) were added to the reaction flask and allowed to stir for 5 minutes at room temperature. In a separate flame-dried vial, the 2,3,4,6-tetra-O-acetyl-α-D-glucopyranosyl bromide 11A-2 (18.53 g, 45.1 mmol, 1.20 eq) was dissolved in anhydrous DMF (30.0 mL) and subsequently added to the reaction mixture dropwise. The reaction mixture was allowed to stir at room temperature for 3 hours. The molecular sieves were removed via vacuum filtration and the collected filtrate was poured onto deionized water (140 mL). This solution was extracted with dichloromethane (5×30 mL), and the combined organic extracts were dried with $MgSO_4$ and concentrated under vacuum. The crude mixture was purified by column chromatography on silica gel using 30% EtOAc—toluene containing 0.25% triethylamine as an eluent. The obtained product was further purified by a second column chromatography on silica gel using 0.5% MeOH—dichloromethane containing 0.25% triethylamine as the eluent to afford the desired glycoside 11A-3 as a white solid (1.85 g, 3.99 mmol, 11%). $^1$H NMR (400 MHz, $CDCl_3$): δ (ppm)=8.22 (s, 1H), 7.17-7.12 (m, 2H), 7.10 (d, J=7.7 Hz, 1H), 6.72 (dd, J=7.6, 0.9 Hz, 1H), 6.57 (ddd, J=3.1, 2.1, 0.9 Hz, 1H), 5.43-5.38 (m, 1H), 5.33 (t, J=9.3 Hz, 1H), 5.25-5.18 (m, 2H), 4.32 (dd, J=12.2, 5.3 Hz, 1H), 4.20 (dd, J=12.2, 2.5 Hz, 1H), 3.89 (ddd, J=9.9, 5.3, 2.5 Hz, 1H), 2.11-2.03 (m, 12H).

To a solution of glycoside 11A-3 (900 mg, 1.94 mmol, 1.00 eq) and 1-(dimethylamino)-2-nitroethylene (248 mg, 2.14 mmol, 1.10 eq) in anhydrous dichloromethane (2.0 mL) under argon, was added trifluoracetic acid (3.32 g, 29.1 mmol, 15.0 eq), and the resulting mixture was stirred at room temperature for 3 hours until completion as determined by TLC (4:1 EtOAc/hexanes). The reaction mixture was diluted with EtOAc (15 mL) and slowly poured onto saturated $NaHCO_3$(100 mL). The biphasic solution was separated, the aqueous phase extracted with EtOAc (4×25 mL), the organic extracts were combined and washed with brine (30 mL), dried with $MgSO_4$, and concentrated under reduced pressure. The mixture was purified by column chromatography on silica gel using a gradient of 45%→60% EtOAc—hexanes as an eluent to yield the desired product 11A-4 as an orange solid (137 mg, 0.256 mmol, 13%). $^1$H NMR (400 MHz, Acetone-$d_6$): δ (ppm)=11.31 (s, 1H), 8.57 (dd, J=13.5, 0.7 Hz, 1H), 8.20-8.11 (m, 2H), 7.98-7.90 (m, 1H), 7.31 (dd, J=8.2, 0.9 Hz, 1H), 7.24 (t, J=8.0 Hz, 1H), 7.02 (dd, J=7.8, 0.9 Hz, 1H), 6.66 (d, J=10.6 Hz, 1H), 5.75 (d, J=8.0 Hz, 1H), 5.48 (t, J=9.5 Hz, 1H), 5.38 (dd, J=9.6, 8.0 Hz, 1H), 5.24 (dd, J=9.9, 9.3 Hz, 1H), 4.33 (dd, J=11.9, 5.2 Hz, 1H), 4.26 (ddd, J=10.0, 5.2, 2.2 Hz, 1H), 4.19 (dd, J=11.9, 2.2 Hz, 1H), 2.05 (s, 3H), 2.01 (s, 3H), 2.01 (s, 3H), 1.97 (s, 3H).

Compound 11A-4 (137 mg, 0.256 mmol, 1.00 eq) was dissolved in a solution of ethanol (1.0 mL)-THF (1.0 mL) at 0° C., and sodium borohydride (48 mg, 1.27 mmol, 5.00 eq) was added. The reaction was stirred at 0° C. for 1 hour, and then warmed up to room temperature for 2 hours. The reaction mixture was poured onto ice-water (20 mL) and extracted with dichloromethane (4×10 mL). The combined organic extracts were washed with brine (15 mL), dried with $MgSO_4$, and concentrated under reduced pressure. The residue was purified by column chromatography on silica gel using a gradient of 30%→50% EtOAc—hexanes as the eluent to afford compound 11A-5 as a white solid (45 mg, 0.0839 mmol, 33%). $^1$H NMR (400 MHz, Acetone-$d_6$): δ (ppm)=10.21 (s, 1H), 7.16-7.03 (m, 3H), 6.79 (dd, J=7.9, 0.8 Hz, 1H), 5.76 (dd, J=7.9, 0.4 Hz, 1H), 5.49 (t, J=9.5 Hz, 1H), 5.35 (dd, J=9.7, 7.9 Hz, 1H), 5.22-5.15 (m, 1H), 4.87-4.74 (m, 2H), 4.35-4.23 (m, 2H), 4.20-4.13 (m, 1H), 3.54-3.39 (m, 2H), 2.08 (s, 3H), 2.05 (s, 3H), 2.01 (s, 3H), 2.00 (s, 3H).

Compound 11A-5 (45 mg, 0.084 mmol, 1.0 eq) was dissolved in anhydrous methanol (1.5 mL) with the help of sonication. A methanolic solution of sodium methoxide (1.5 M, 0.10 mL, 0.15 mmol, 1.8 eq) was added and the reaction was stirred at room temperature for 10 minutes. TLC (10% MeOH—dichloromethane revealed that the starting material was consumed. Acetic acid was added until a pH of 5-6 was achieved. The reaction mixture was concentrated under reduced pressure to afford compound 11A-6 as an amber oil that was used directly in the following step without purification.

To a vigorously stirring solution of above crude compound 11A-6 in methanol (5.0 mL) was added 10% palladium on activated charcoal (70 mg, 0.066 mmol) and ammonium formate (140 mg, 2.22 mmol), and the resulting mixture was heated to 50° C. for 1 hour. The reaction mixture was cooled to room temperature, filtered to remove the catalyst, and concentrated under reduced pressure. The mixture was purified by size exclusion chromatography on Sephadex LH-20 using methanol as the eluent to yield compound 11A-7 as a white solid (23 mg, 0.058 mmol, 69% over 2 steps). $^1$H NMR (400 MHz, $D_2O$): δ (ppm)=7.18-7.06 (m, 3H), 6.73 (dd, J=7.5, 0.9 Hz, 1H), 5.25 (d, J=7.3 Hz, 1H), 3.84 (dd, J=12.5, 2.2 Hz, 1H), 3.67 (dd, J=12.4, 5.7 Hz, 1H), 3.63-3.52 (m, 3H), 3.48-3.39 (m, 1H), 3.29 (ddt, J=10.3, 7.0, 4.9 Hz, 2H), 3.25-3.11 (m, 2H), 1.86 (s, 7H). $^{13}$C NMR (100 MHz, $D_2O$): δ (ppm)=150.6, 138.6, 124.2, 122.8, 116.8, 108.8, 107.0, 102.9, 100.0, 99.4, 76.1, 73.1, 69.4, 60.6, 40.8, 24.2, 22.8.

Example 2—Processes for Making β-4-O-Galactosyl-Psilocybin Derivatives

This example refers to FIG. 11B and describes an example process for making β-4-O-galactosyl-psilocybin derivatives, notably compounds having the formula (V) and (VI):

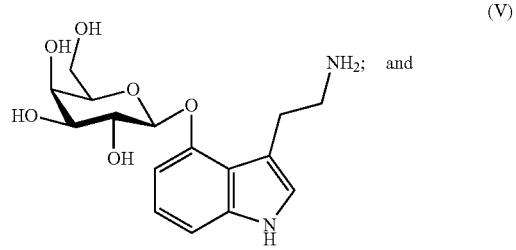

(V)

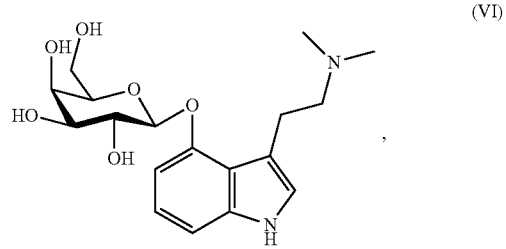

(VI)

It is noted that in FIG. 11B, compounds (V) and (VI) correspond with compounds 11B-7 and 11B-8, respectively.

To a solution of 4-hydroxyindole (11B-1, 1.0 g, 7.51 mmol) in DMF (10.0 mL) was added tetramethyammonium hydroxide pentahydrate (1.36 g, 7.51 mmol) under argon, and the mixture was stirred at ambient temperature for 10 mins. Molecular sieves 4A (2.0 g) was added and the mixture was stirred for another 10 mins. Then 2,3,4,6-Tetra-O-acetyl-β-D-galactopyranosyl bromide (11B-2, 4.63 g, 11.3 mmol, 1.5 equiv.) was added in small portions, and the reaction was continued for 18 hours. The reaction mixture was diluted with EtOAc (~100 mL) and filtered off to remove the insoluble materials. The organic solution was washed with 10% brine (2×50 mL), dried over anhydrous $Na_2SO_4$ and evaporated. The residue was purified by column chromatography on silica gel using a gradient of EtOAc-hexanes (10→40%) as the eluent to afford the desired glycoside 11B-3 (1.41 g, 41% yield). $^1$H NMR (400 MHz, $CDCl_3$) δ 8.38 (s, 1H), 7.17-7.12 (m, 2H), 7.09 (t, J=7.9 Hz, 1H), 6.73 (dd, J=7.6, 0.7 Hz, 1H), 6.58 (m, 1H), 5.63 (dd, J=10.5, 8.0 Hz, 1H), 5.48 (dd, J=1.0, 3.5 Hz, 1H), 5.17 (d, J=7.9 Hz, 1H), 5.14 (dd, J=10.4, 3.4 Hz, 1H), 4.28 (dd, J=11.2, 7.0 Hz, 1H), 4.20 (dd, J=11.2, 6.3 Hz, 1H), 4.12-4.06 (ddd, J=6.7, 6.7, 1.0 Hz, 1H), 2.19 (s, 3H), 2.07 (s, 3H), 2.07 (s, 4H), 2.03 (s, 3H). $^{13}$C NMR (101 MHz, $CDCl_3$) δ 170.4, 170.35, 170.2, 169.6, 150.6, 137.5, 123.6, 122.4, 119.5, 106.8, 104.9, 100.5, 99.6, 71.0, 70.8, 68.8, 67.0, 61.4, 20.8, 20.7 (x2), 20.6. HRMS (ESI) m/z for $C_{22}H_{25}NO_{10}Na$ (M+Na)$^+$ calcd 486.1371, found 486.1370.

A solution of compound 11B-3 (PZ11088, 95.4 mg, 0.206 mmol) and 1-(dimethylamino)-2-nitroethylene (26.3 mg, 0.226 mmol, 1.1 equiv.) in anhydrous dichloromethane (0.8 mL) was cooled to 0° C., and trifluoroacetic acid (0.5 mL) was added. After stirring for 20 mins, the mixture was diluted with EtOAc (40 mL), and washed with a solution of 2N NaOH (1×10 mL) followed by 10% aqueous $NaHCO_3$ (1×10 mL), dried over anhydrous $Na_2SO_4$ and evaporated. The residue was purified by column chromatography on silica gel using a gradient of EtOAc-hexanes (10→50%) containing 0.1% $Et_3N$ as the eluent to afford the desired compound 11B-4 (36.8 mg, 33% yield). $^1$H NMR (400 MHz, Acetone-$d_6$) δ 11.27 (s, 1H), 8.59 (dd, J=13.4, 0.5 Hz, 1H), 8.16 (s, 1H), 7.98 (d, J=13.5 Hz, 1H), 7.29 (dd, J=8.1, 0.9 Hz, 1H), 7.23 (t, J=8.0 Hz, 1H), 7.01 (dd, J=7.8, 0.7 Hz, 1H), 5.71 (d, J=8.1 Hz, 1H), 5.60 (dd, J=10.2, 8.1 Hz, 1H), 5.50 (dd, J=3.5, 1.0 Hz, 1H), 5.33 (dd, J=10.2, 3.5 Hz, 1H), 4.48 (td, J=6.5, 1.1 Hz, 1H), 4.23-4.13 (m, 2H), 2.21 (d, J=3.1 Hz, 3H), 1.97 (s, 3H), 1.96 (s, 3H), 1.96 (s, 3H). $^{13}$C NMR (101 MHz, Acetone-$d_6$) δ 170.0, 169.6, 169.4, 168.5, 151.3, 133.8, 133.79 (x2), 130.4, 130.2, 124.0, 107.8, 107.78, 106.9, 99.5, 71.1, 71.0, 68.9, 67.4, 61.3, 19.9, 19.7, 19.66, 19.6.

To a solution of compound 11B-4 (PZ11098-2, 36.8 mg, 0.0689 mmol) in methanol (1.0 mL) was added $NaBH_4$ (13.0 mg, 0.343 mmol, 5 equiv.) in small portions, and reaction was stirred for 1 hour at ambient temperature. Then AcOH (2 drops) was added, and the reaction mixture was diluted with EtOAc (20 mL), washed with a solution of 10% brine (2×10 mL), dried over anhydrous $Na_2SO_4$ and evaporated. The residue was purified by column chromatography on silica gel using a gradient of EtOAc-hexanes (10→50%) containing 0.1% $Et_3N$ as the eluent to afford the desired compound 11B-5 (25.2 mg, 68% yield). $^1$H NMR (400 MHz, Acetone-$d_6$) δ 10.21 (s, 1H), 7.11 (m, 2H), 7.05 (t, J=7.9 Hz, 1H), 6.78 (d, J=7.3 Hz, 1H), 5.71 (d, J=8.0 Hz, 1H), 5.53 (dd, J=10.4, 8.0 Hz, 1H), 5.50 (dd, J=3.6, 1.0 Hz, 1H), 5.34 (dd, J=10.4, 3.6 Hz, 1H), 4.87-4.73 (m, 2H), 4.49 (ddd, J=6.5, 6.5, 1.1 Hz, 1H), 4.23-4.14 (m, 2H), 3.54-3.40 (m, 2H), 2.19 (s, 3H), 2.09 (s, 3H), 1.98 (s, 3H), 1.97 (s, 3H). $^{13}$C NMR (101 MHz, Acetone-$d_6$) δ 169.9, 169.4 (x3), 150.8, 138.9, 128.9, 128.1, 123.2, 122.2, 106.7, 103.0, 97.8, 76.8, 70.9, 70.89, 68.8, 67.4, 61.3, 24.7, 19.9, 19.7, 19.65, 19.6.

To a solution of compound 11B-5 (PZ11102, 41 mg, 0.0764 mmol) in anhydrous methanol (3.0 mL) was added a solution of NaOMe in anhydrous MeOH (~1.0 M, 30 mL), and reaction was stirred at ambient temperature for 1 hour. AcOH (2 drops) was added, and the reaction mixture was evaporated to dryness under reduced pressure. NMR spectra of the crude compound 11B-6 showed a complete removal of the O-acetates. $^1$H NMR (400 MHz, $CD_3OD$) δ 8.55 (s, 1H), 7.05-6.97 (m, 2H), 6.96 (s, 1H), 6.80-6.71 (m, 1H), 5.13 (d, J=7.8 Hz, 1H), 4.88 (t, J=7.0 Hz, 2H), 3.98 (d, J=3.0, 0.7 Hz, 1H), 3.90 (dd, J=9.6, 7.8 Hz, 1H), 3.80 (m, 2H), 3.74 (ddd, J=6.2, 5.2, 0.7 Hz, 1H), 3.65 (dd, J=3.4, 9.6 Hz, 1H), 3.64-3.47 (m, 2H). Selected $^{13}$C NMR (101 MHz, $CD_3OD$) b 154.4, 135.7, 129.2, 128.5, 122.5, 121.9, 109.2, 105.7, 104.0, 102.7, 101.2, 77.1, 75.4, 74.0, 71.1, 68.9, 60.9, 25.2.

To a solution of the crude residue 11B-6 (PZ11104) obtained from above in MeOH (3.0 mL), was added 10% Pd/C (35 mg) and ammonium formate (85 mg), and the mixture was heated at 60° C. After 30 mins, the solution was filtered off through a syringe membrane, and evaporated to dryness. The residue was purified by size exclusion chromatography on Sephadex LH-20 using methanol as an eluent to afford the desired compound 11B-7 which was freeze-dried as white solid (24.6 mg, 81%). $^1$H NMR (400 MHz, $D_2O$) b 7.12-7.07 (dd, J=0.8, 7.6 Hz, 1H), 7.05 (m, 2H), 6.66 (d, J=0.8, 7.6 Hz, 1H), 5.07 (d, J=7.9 Hz, 1H), 3.85 (d, J=3.4 Hz, 1H), 3.77 (dd, J=9.8, 7.9 Hz, 1H), 3.64 (m, 3H), 3.58 (dd, J=9.9, 3.4 Hz, 1H), 3.29-3.21 (m, 2H), 3.19-3.03 (m, 2H), 1.78 (s, 3H). $^{13}$C NMR (101 MHz, $D_2O$) δ 181.4, 150.7, 138.5, 124.1, 122.8, 116.7, 108.8, 106.8, 102.7, 99.8, 75.3, 73.0, 70.6, 68.4, 60.7, 40.8, 24.2, 23.2. HRMS (ESI) m/z for $C_{16}H_{23}N_2O_6$ (M+H)$^+$ calcd 339.1551, found 339.1568.

To a solution of compound 11B-7 (PZ11105, 19.2 mg, 0.0568 mmol) in MeOH (1.0 mL) at 0° C., was added 37% formaldehyde in water (12 mL, 0.137 mmol), AcOH (13 mL, 1.17 mmol) and $NaBH_3CN$ (7.6 mg, 0.115 mmo), and the reaction was continued at ambient temperature overnight. A solution of 10% $NaHCO_3$ was added to adjust the pH of the solution to 8-9, and the mixture was concentrated under reduced pressure. The residue was purified by size exclusion chromatography on Sephadex LH-20 using methanol as an eluent to afford the desired compound 11B-8 which was freeze-dried as white solid (19.3 mg, 94%). $^1$H NMR (400 MHz, $D_2O$) δ 7.16-7.02 (m, 3H), 6.69 (dd, J=0.9, 7.6 Hz, 1H), 5.14 (d, J=7.9 Hz, 1H), 3.89 (dd, J=0.6, 3.5 Hz, 1H), 3.78 (dd, J=7.9, 9.8 Hz, 1H), 3.75 (ddd, J=0.8, 6.1, 6.1 Hz, 1H), 3.71-3.60 (m, 3H), 3.38 (m, 2H), 3.19 (m, 2H), 2.75 (s, 6H), 1.80 (s, 3H). $^{13}$C NMR (101 MHz, $D_2O$) δ 150.7, 138.5, 124.1, 122.9, 116.6, 108.1, 106.9, 102.8, 100.0, 75.4, 73.0, 70.7, 68.5, 60.8, 58.9, 42.7, 23.2, 21.9. HRMS (ESI) m/z for $C_{18}H_{27}N_2O_6$ (M+H)$^+$ calcd 367.1867, found 367.1857.

Example 3—Efficacy of a
β-4-O-Glucosyl-Psilocybin Derivative

This example describes the performance of calcium mobilization assays to demonstrate activation of 5-HT$_{2A}$ receptor by a first example glycosylated psilocybin derivative, namely a β-4-O-glucosyl-psilocybin compound having the formula (III) (see: Example 1). The 5-HT$_{2A}$ receptor belongs to the class of serotonin receptors and is known to be playing a role in the mediation of responses to serotonogenic compounds.

Cell lines for pharmacology assays. CHO-K1/Galpha15 (GenScript, M00257) (−5-$HT_{2A}$) and CHO-K1/5-$HT_{2A}$ (GenScript, M00250) (+5-$HT_{2A}$) cells lines were used in both toxicology/growth inhibition (MTT) and calcium release assays. Briefly, CHO-K1/Galpha15 is a control cell line that constitutively expresses Galpha15 which is a promiscuous Gq protein. It is engineered as a host cell, allowing transfected receptor(s) to signal through the Gq signal transduction pathway and mobilize intracellular calcium from the endoplasmic reticulum (ER). These control cells lack any transgene encoding 5-$HT_{2A}$ receptors, thus preventing calcium mobilization in response to 5-$HT_{2A}$ activation. Conversely, CHO-K1/5-$HT_{2A}$ cells stably express 5-$HT_{2A}$ receptor in the CHO-K1 host background. This design enables Gq-11 expressed in CHO-K1 cells to mobilize intracellular calcium changes when 5-$HT_{2A}$ receptors are activated by ligands.

Cell lines were maintained in Ham's F12 media plus 10% FBS in the presence of 100 ug/ml hygromycin for CHO-K1/Ga15 or 400 ug/ml G418 for CHO-K1/5-$HT_{2A}$ unless indicated otherwise for specific assays. Cell maintenance was carried out as recommended by the cell supplier. Briefly, vials with cells were removed from the liquid nitrogen and thawed quickly in 37° C. water bath. Just before cells were completely thawed, vial exteriors were decontaminated with 70% ethanol spray. Cell suspension was then retrieved from the vial and added to warm (37° C.), 'complete' (non-dropout) growth media, and centrifuged at 1,000 rpm for 5 minutes. The supernatant was discarded and the cell pellet was then resuspended in another 10 ml of complete growth media, and added to a 10 cm cell culture dish (Greiner Bio-One #664160). The media was changed every third day until the cells reached ~90% confluence. The ~90% confluent cells were then split 10:1, and used either for maintenance or pharmacological study.

Figure 12A:
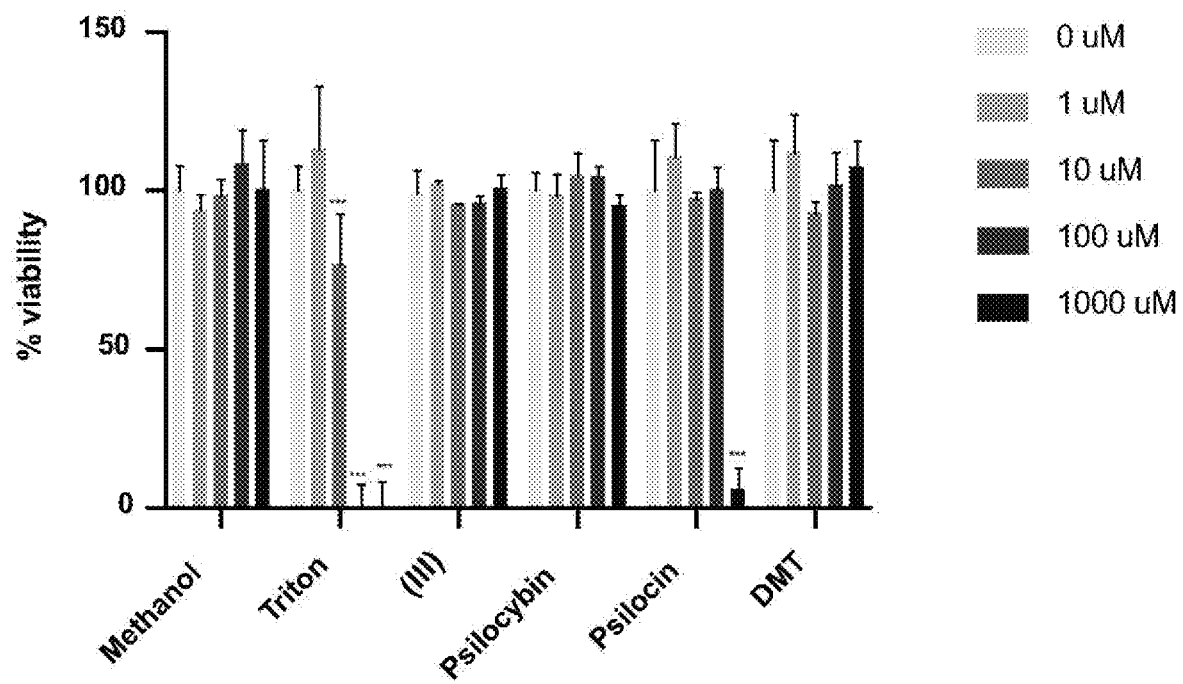
FIGS. 12A-12C depict certain graphs obtained in the performance of experimental assays to evaluate the efficacy of an example glucosyl psilocybin derivative, notably cell viability assays (FIG. 12A), and 5-$HT_{2a}$ receptor modulation assays involving activation by psilocin (positive control) (FIG. 12B), and activation by the example glucosyl psilocybin derivative (FIG. 12C).

Assessment of cell viability upon treatment of glycosylated psilocybin derivatives. To establish suitable ligand concentrations for the calcium release assays, MTT (3-(4, 5-dimethylthiazol-2-yl)-2,5-diphenyltetrazolium) assays were first performed. Results of these assays were conducted using both control ligands (e.g. psilocybin, psilocin, DMT) and novel derivatives, in part as a pre-screen for any remarkable toxic effects on cell cultures up to concentrations of 1 mM. A known cellular toxin (Triton X-100, Pyrgiotakis G. et al., 2009, Ann. Biomed. Eng. 37: 1464-1473) was included as a general marker of toxicity. Modified Chinese Hamster Ovary cells (CHO-K1/Ga15) were cultured using standard procedures using the manufacture's protocols (Genscript, M00257). Briefly, cells were cultured in Ham's F12 medium supplemented with 10% fetal bovine serum and 100 mg/ml Hygromycin B, and grown at 37° C. in the presence of 5% $CO_2$. To test the various compounds with the cell line, cells were seeded in a clear 96-well culture plate at 10,000 cells per well. After allowing cells to attach and grow for 24 hours, assay compounds were added at 1 μM, 10 μM, 100 μM, and 1 mM final concentrations. Methanol concentrations used are 0.001, 0.01, 0.1, and 1%. Triton concentrations used are 0.0001, 0.001, 0.01 and 0.1%. Cells were incubated with compounds for 48 hours before accessing cell viability with the MTT assay following the manufacture's protocol (MTT Cell Growth Assay Kit; Millipore Sigma, CT02). MTT reagent was added to cells and allowed to incubate for 4 hours before solubilization with isopropanol plus 0.04 N HCl. Absorbance readings were performed at 570 nm with the reference at 630 nm on a SpectraMax iD3 plate reader. Non-treated cells were assigned 100% viability. Results of the cell viability assays are shown in FIG. 12A. Bar graphs show the mean +/−SD (n=3). Significance (P<0.0001), as indicated by (***) was determined using 2-way ANOVA with Dunnett's multiple comparisons test. The results using β-4-O-glucosyl-psilocybin are indicated as "(III)" on the x-axis.

Figure 12B:
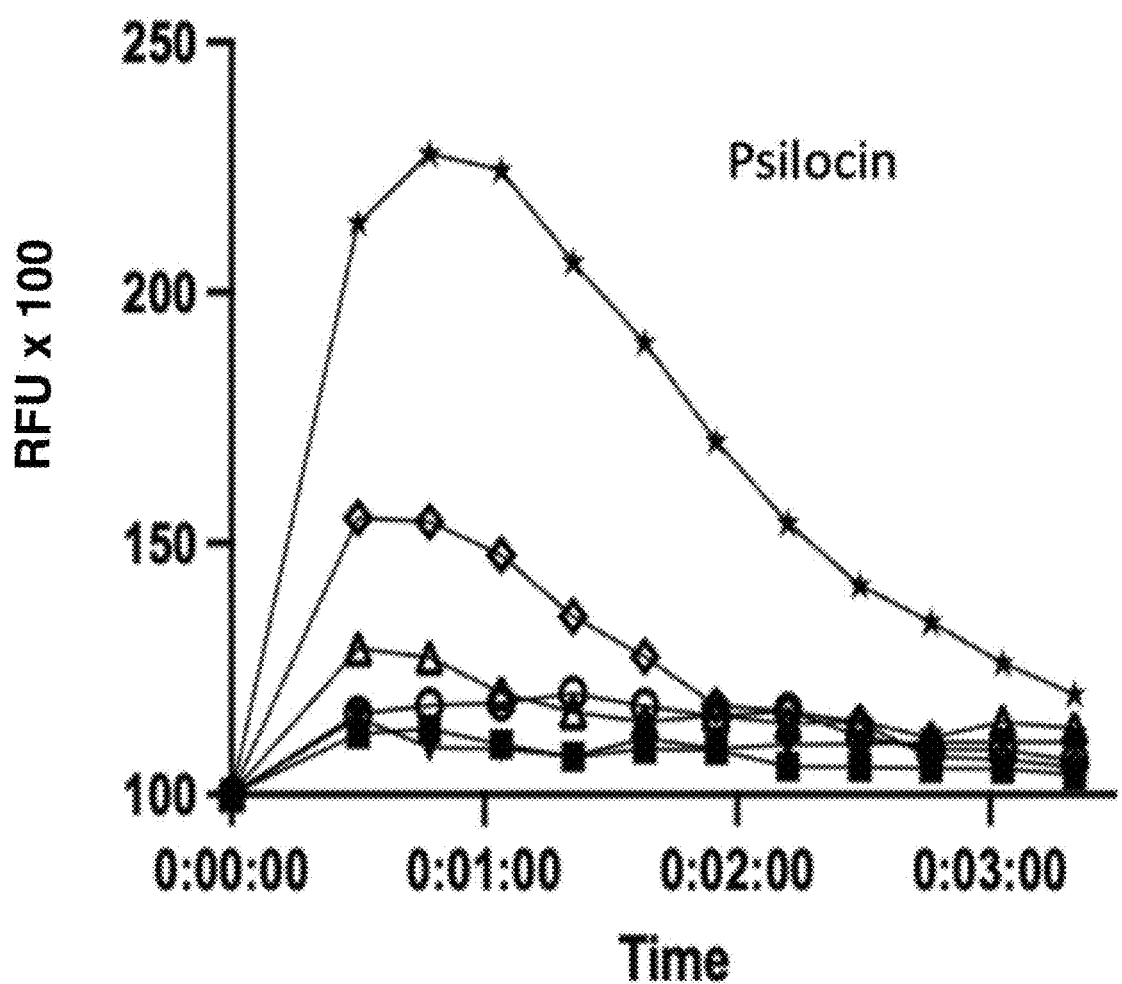
Figure 12C:
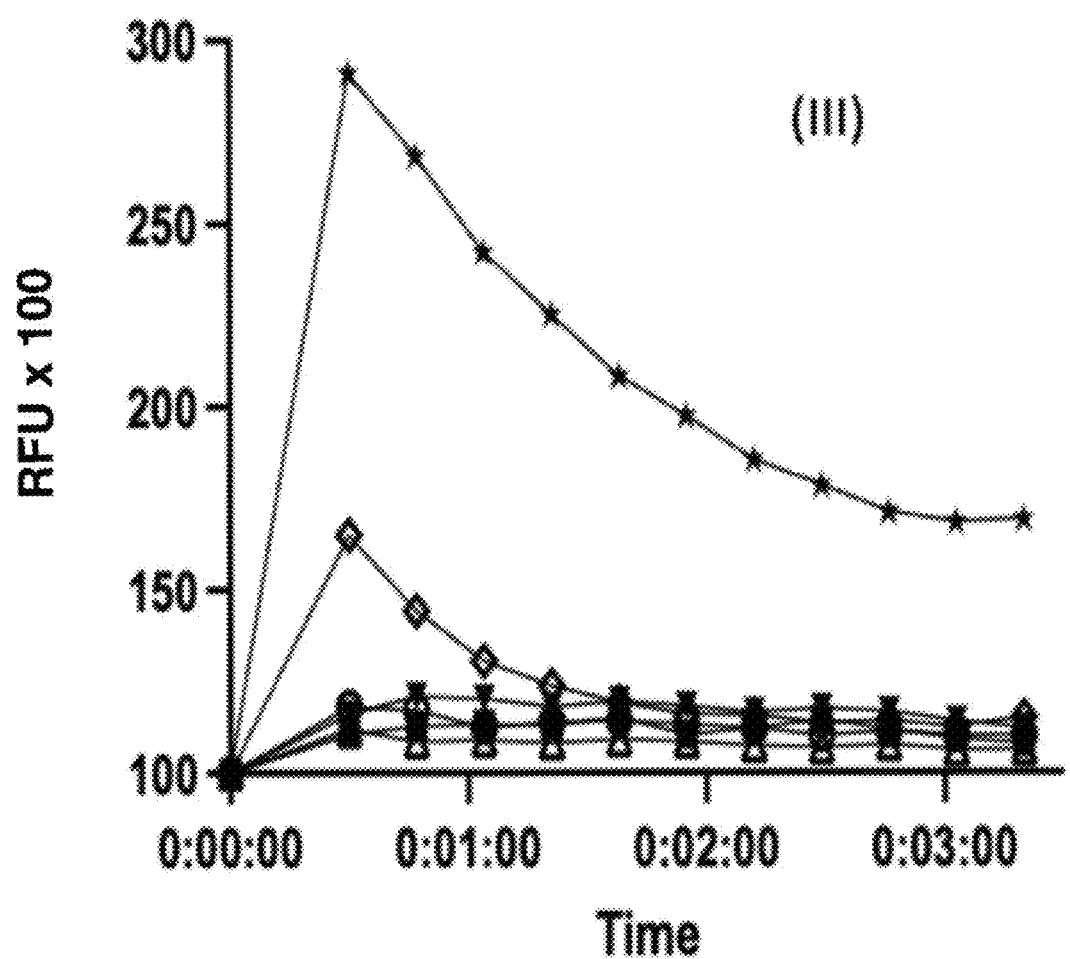

Increase in cytosolic calcium concentration by 5-$HT_{2A}$ activation. Changes in intracellular calcium concentration due to the treatment with assay compounds was measured using Fluo-8 dye (Abcam, #ab112129) according to the manufacturer's instructions. Briefly, CHO-K1 cells stably expressing 5-$HT_{2A}$ (Genscript #M00250) (+5-$HT_{2A}$) or lacking 5-$HT_{2A}$ (Genscript, M00257) (−5-$HT_{2A}$) were seeded on black walled clear bottom 96-well plates (Thermo Scientific #NUNC165305), allowing 70,000 cells/well in 100 ul media (HAM's F12, GIBCO #11765-047) with 1% FBS (Thermo Scientific #12483020). Cultures were maintained in a humidified incubator at 37° C. and 5% $CO_2$. Fluo-8 dye was loaded into the cultures for 30 min at 37° C., followed by 30 min additional incubation at room temperature. Next, different dilutions of novel molecules and controls were prepared in serum-free culture media and added to the cells. Fluorescence (ex 490 nm/em 525 nm) obtained after the addition of molecules was expressed relative to values obtained before addition of the molecules (relative Fluo-8 fluorescence=Fmax/F0, where Fmax=maximum fluorescence and F0=baseline fluorescence). Fluorescence intensities were measured using a Spectramax ID3 plate reader (www.moleculardevices.com). Relative fluorescence (RFU) was plotted with respected to time (seconds) illustrating time-dependent calcium flux. Psilocin, a known agonist with binding activity at 5-$HT_{2A}$ (Rickli A. et al., 2016, Europ. Neuropsychopharmacol., 26: 1326-1337) was used as a positive control to establish assay functionality. The Example compound (Ill) was then evaluated. Results are shown in FIGS. 12B and 12C. The results using different concentrations of psilocin and β-4-O-glucosyl-psilocybin (indicated as "(III)") are shown in FIG. 12B and FIG. 12C, respectively as black squares (0.001 μM), black triangles (0.01 μM), open circles (0.1 μM), open triangles (1 μM), open diamonds (10 μM), and black stars (100 μM). Intracellular calcium flux peaked in both cases in under 60 seconds, and response increased with dosage. Corresponding data for −5-$HT_{2A}$ cells (CHO-K1/Galpha15, GenScript, M00257) did not exhibit a response to either psilocin or β-4-O-glucosyl-psilocybin.

Example 4—Efficacy of a First β-4-O-Galactosyl-Psilocybin Derivative

Figure 13A:
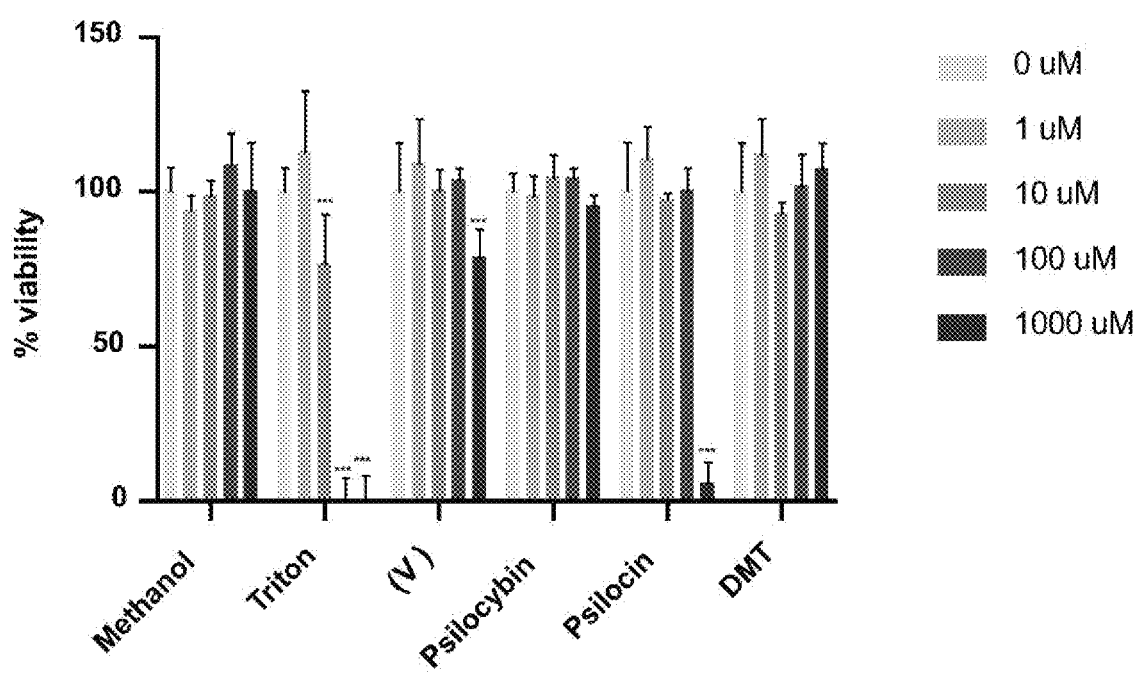
FIGS. 13A and 13B depict certain graphs obtained in the performance of experimental assays to evaluate the efficacy of a first example galactosyl psilocybin derivative, notably cell viability assays (FIG. 13A), and a 5-$HT_{2a}$ receptor modulation assay involving activation by the first example galactosyl psilocybin derivative (FIG. 13B).

This example describes the performance of calcium mobilization assays to demonstrate activation of 5-$HT_{2A}$ receptor by a second example glycosylated psilocybin derivative, namely a first β-4-O-galactosyl-psilocybin derivative compound having the formula (V) (see: Example 2). The assay methods were as described in Example 3. Briefly, to establish suitable ligand concentrations for the calcium release assays, MTT (3-(4,5-dimethylthiazol-2-yl)-2,5-diphenyltetrazolium) assays were first performed. CHO-K1/Ga15 cells were treated with 1 μM, 10 μM, 100 μM, and 1 mM of derivative for 48 hours and cell viability was measured by MTT assay (n=3). Methanol concentrations used are 0.001, 0.01, 0.1, and 1%. Triton concentrations used are 0.0001, 0.001, 0.01 and 0.1%. Results of the cell viability assays are shown in FIG. 13A. Bar graphs show the mean +/−SD.

Significance (P<0.001) was determined by 2-way ANOVA followed by Dunnett's multiple comparison test and is indicated by ***. The results using the first β-4-O-galactosyl-psilocybin (compound V) are indicated as "(V)" on the x-axis.

Figure 13B:
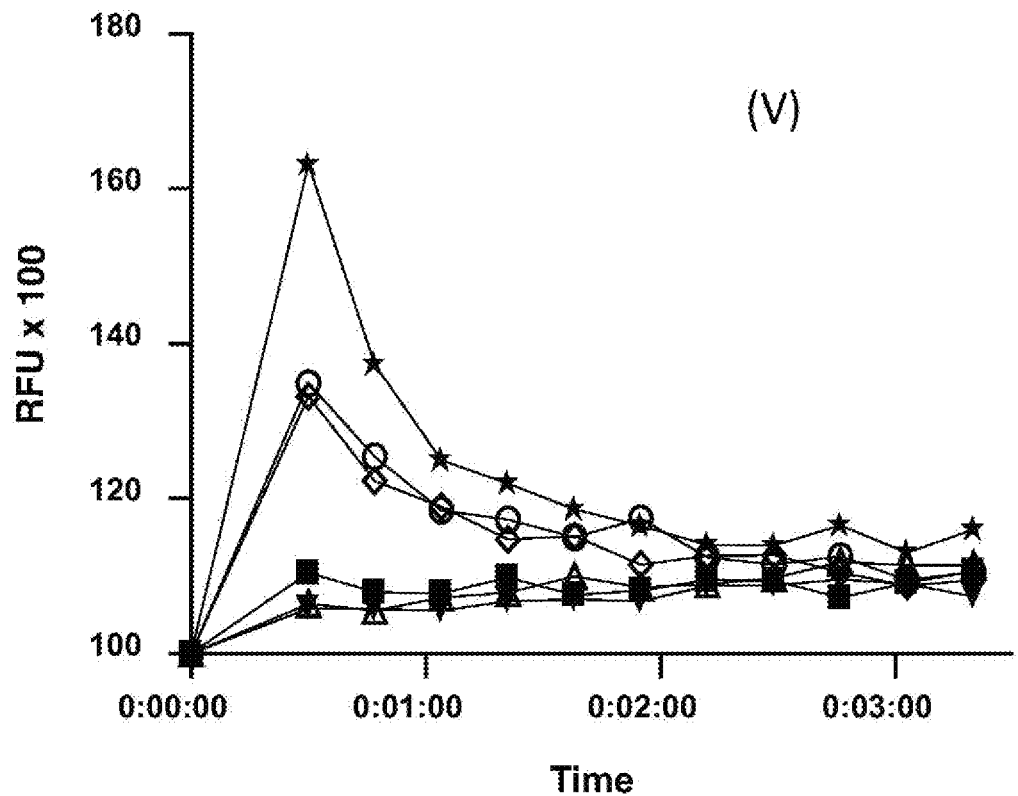

To assess changes in cytosolic calcium concentration in response to 5-$HT_{2A}$ activation, the derivative was evaluated in the same manner as psilocin and Example compound with formula (III) (see: Example 3). The results are shown in FIG. 13B. Responses to different concentrations of the first β-4-O-galactosyl-psilocybin (compound V) are shown as black squares (0.001 μM), black triangles (0.01 μM), open circles (0.1 μM), open triangles (1 μM), open diamonds (10 μM), and black stars (100 μM). Intracellular calcium flux peaked in under 60 seconds, and response increased with dosage. Corresponding data for −5-$HT_{2A}$ cells (CHO-K1/Galpha15, GenScript, M00257) did not exhibit a response to the first β-4-O-galactosyl-psilocybin (compound V).

Example 5—Efficacy of a Second β-4-O-Galactosyl-Psilocybin Derivative

Figure 14A:
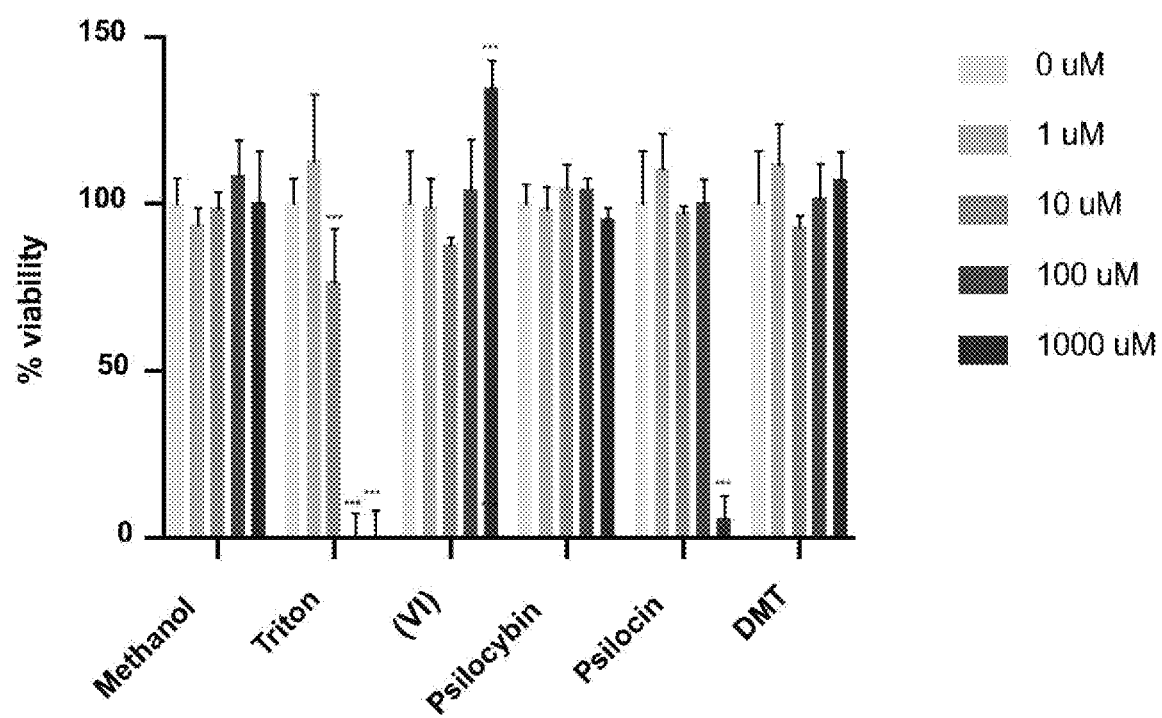
FIGS. 14A-14C depict certain graphs obtained in the performance of experimental assays to evaluate the efficacy of a second example galactosyl psilocybin derivative, notably cell viability assays (FIG. 14A), and 5-$HT_{2a}$ receptor modulation assays involving activation by psilocin (positive control) (FIG. 14B), and activation by the second example galactosyl psilocybin derivative (FIG. 14C).

This example describes the performance of calcium mobilization assays to demonstrate activation of 5-$HT_{2A}$ receptor by a second example glycosylated psilocybin derivative, namely a second β-4-O-galactosyl-psilocybin compound having the formula (VI) (see: Example 2). The assay methods were as described in Example 3, with additional analysis of calcium mobilization data as described herein. Briefly, to establish suitable ligand concentrations for the calcium release assays, MTT (3-(4,5-dimethylthiazol-2-yl)-2,5-diphenyltetrazolium) assays were first performed. CHO-K1/Ga15 cells were treated with 1 μM, 10 μM, 100 μM, and 1 mM of derivative for 48 hours and cell viability was measured by MTT assay (n=3). Methanol concentrations used are 0.001, 0.01, 0.1, and 1%. Triton concentrations used are 0.0001, 0.001, 0.01 and 0.1%. Results of the cell viability assays are shown in FIG. 14A. Bar graphs show the mean +/−SD. Significance (P<0.001) was determined by 2-way ANOVA followed by Dunnett's multiple comparison test and is indicated by ***. The results using the second β-4-O-galactosyl-psilocybin (compound VI) are indicated as "(VI)" on the x-axis.

Figure 14B:
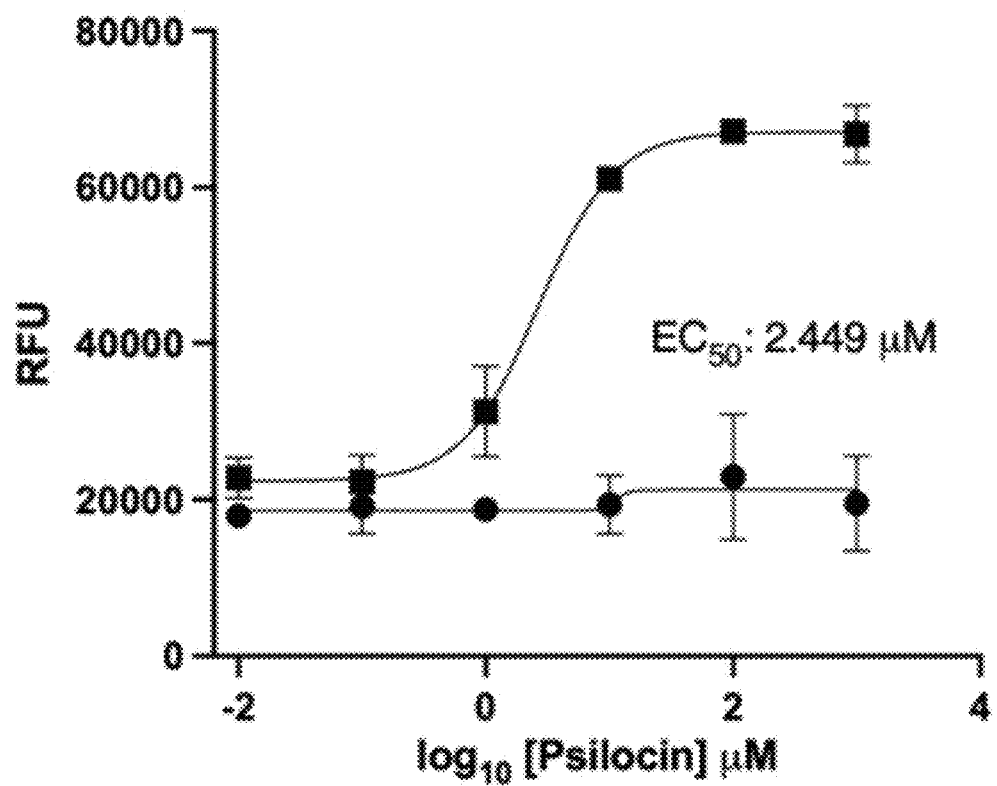
Figure 14C:
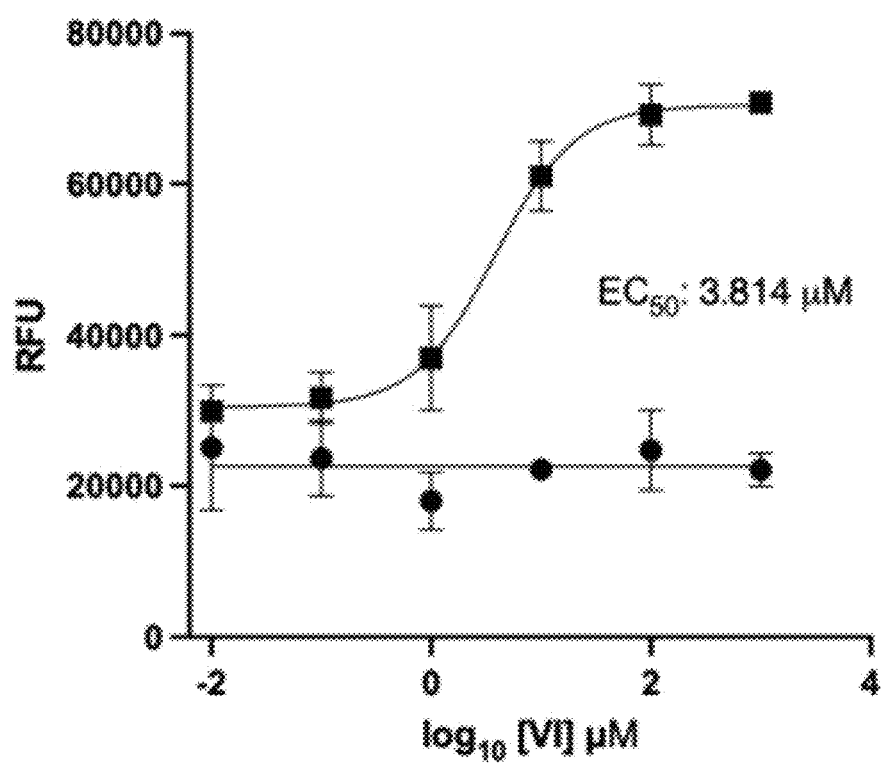

To assess changes in cytosolic calcium concentration in response to 5-$HT_{2A}$ activation, the derivative was evaluated in the same manner as in Example 3, with additional, curve-fitting analysis as follows. Relative fluorescence (RFU) was subjected to four parameter logistic curve fittings to determine $EC_{50}$ (3.814 uM) with the aid of GraphPad Prism (Version 9.2.0). The results are shown in FIG. 14B (control) and FIG. 14C (β-4-O-galactosyl-psilocybin (compound VI)). Squares represent data acquired using CHO-K1/5-$HT_{2A}$ (GenScript, M00250) (+5-$HT_{2A}$) and circles represent data acquired using CHO-K1/Galpha15 (GenScript, M00257) (−5-$HT_{2A}$). Standard deviation about the mean is indicated. Psilocin, a known agonist with binding activity to 5-$HT_{2A}$ (Rickli et al., 2016, European Neuropsychopharmacology 26: 1327-1337), was used as a positive control to assess assay functionality ($EC_{50}$ 2.449 uM) (FIG. 14B).

The invention claimed is:

1. A chemical compound of formula (I):

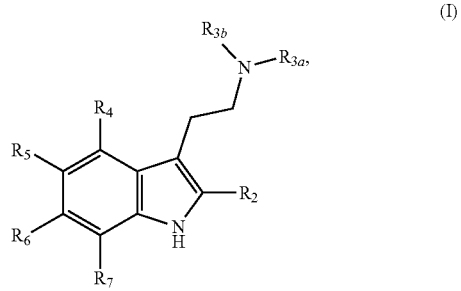

(I)

or a salt thereof, wherein $R_4$ is a galactosyl group, and wherein $R_2$, $R_5$, $R_6$ and $R_7$ are independently a hydrogen atom, an alkyl group or O-alkyl group, or a glycosyl group, and wherein $R_{3a}$ and $R_{3b}$ are independently a hydrogen atom, an alkyl group, an aryl group, or an acyl group.

2. A chemical compound according to claim 1, wherein the galactosyl group is a galactosyloxy group.

3. A chemical compound according to claim 1, wherein the galactosyl group is a C-linked galactosyl group.

4. A chemical compound according to claim 1, wherein the galactosyl group is bonded in the furanose or pyranose form from its anomeric carbon atom.

5. A chemical compound according to claim 1, wherein the galactosyl group is a di or tri-saccharide, wherein the second and/or third glycosyl group is independently selected from a glucosyl group, glucuronic acid group, a galactosyl group, a mannosyl group, a fucosyl group, a xylosyl group, an arabinosyl group, a rhamnosyl group, a glucosaminyl group and a galactosaminyl group.

6. A chemical compound according to claim 2, wherein the galactosyl group is a di or tri-saccharide, wherein the second and/or third glycosyl group is independently selected from a glucosyl group, glucuronic acid group, a galactosyl group, a mannosyl group, a fucosyl group, a xylosyl group, an arabinosyl group, a rhamnosyl group, a glucosaminyl group and a galactosaminyl group.

7. A chemical compound according to claim 1, wherein $R_2$, $R_5$, $R_6$, and $R_7$ each are a hydrogen atom.

8. A chemical compound according to claim 1, wherein one or at least one of $R_2$, $R_5$, $R_6$, and $R_7$ is an alkyl group, and the remaining of $R_2$, $R_5$, $R_6$, and $R_7$ are a hydrogen atom.

9. A chemical compound according to claim 8, wherein the one or at least one alkyl group is a $C_1$-$C_6$ alkyl group.

10. A chemical compound according to claim 8, wherein the one or at least one alkyl group is a methyl (—$CH_3$) group.

11. A chemical compound according to claim 1, wherein one or at least one of $R_2$, $R_5$, $R_6$, and $R_7$ is an O-alkyl group, and the remaining of $R_2$, $R_5$, $R_6$, and $R_7$ are a hydrogen atom.

12. A chemical compound according to claim 11, wherein the one or at least one O-alkyl group is a $C_1$-$C_6$ O-alkyl group.

13. A chemical compound according to claim 11, wherein the one or at least one alkyl group is a methoxy (—$OCH_3$) group.

14. A chemical compound according to claim 1, wherein one or at least one of $R_2$, $R_5$, $R_6$, and $R_7$ is a glycosyl group, and the remaining of $R_2$, $R_5$, $R_6$, and $R_7$ are a hydrogen atom.

15. A chemical compound according to claim 14, wherein the glycosyl group is a C-linked glycosyl group.

16. A chemical compound according to claim 14, wherein the glycosyl group is a glycosyl group bonded in the furanose or pyranose form from its anomeric carbon atom.

17. A chemical compound according to claim 14, wherein the glycosyl group is selected from a mono-saccharide, di-saccharide, or tri-saccharide.

18. A chemical compound according to claim 14, wherein the glycosyl group is selected from a pentosyl group, a hexosyl group, and a heptosyl group.

19. A chemical compound according to claim 14, wherein the glycosyl group is selected from a glucosyl group, glucuronic acid group, a galactosyl group, a mannosyl group, a fucosyl group, a xylosyl group, an arabinosyl group, a rhamnosyl group, a glucosaminyl group and a galactosaminyl group.

20. A chemical compound according to claim 1, wherein and $R_{3a}$ and $R_{3b}$ are two hydrogen atoms; a hydrogen atom and a $C_1$-$C_6$ alkyl group; or two $C_1$-$C_6$ alkyl groups.

21. A chemical compound according to claim 1, wherein and $R_{3a}$ and $R_{3b}$ are two hydrogen atoms; a hydrogen atom and a phenyl group; or two phenyl groups.

22. A chemical compound according to claim 1, wherein the chemical compound has formula (VI):

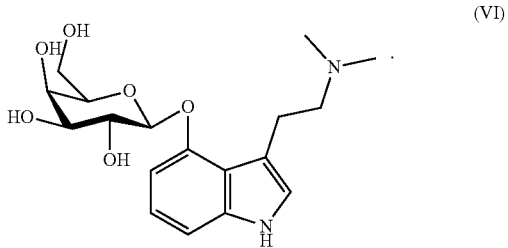

(VI)

23. A chemical compound or salt thereof according to claim 1, wherein the compound is at least about 95% pure.

24. A pharmaceutical or recreational drug formulation comprising an effective amount of a chemical compound according to claim 1, together with a pharmaceutically acceptable diluent, excipient, or carrier.

25. A method for treating a psychiatric disorder, the method comprising administering to a subject in need thereof a pharmaceutical formulation comprising a chemical compound according to claim 1, wherein the pharmaceutical formulation is administered in an effective amount to treat the psychiatric disorder in the subject.

26. A pharmaceutical or recreational drug formulation comprising an effective amount of a chemical compound according to claim 22, together with a pharmaceutically acceptable diluent, excipient, or carrier.

* * * * *

SEQUENCE LISTING

```
Sequence total quantity: 10
SEQ ID NO: 1            moltype = DNA  length = 1593
FEATURE                 Location/Qualifiers
source                  1..1593
                        mol_type = genomic DNA
                        organism = Homo sapiens
SEQUENCE: 1
atggctgcg  cagggtggac  cagccccgtt  cctttatgtg  tgtgtctact  gctgacctgt   60
ggctttgccg  aggcagggaa  gctgctggta  gtgcccatgg  atgggagtca  ctggttcacc  120
atgcagtcgg  tggtggagaa  acttatcctc  aggggggcatg  aggtggttgt  agtcatgcca  180
gaggtgagtt  ggcaactgga  aagatcactg  aattgcacag  tgaagactta  ctcaacctcg  240
tacactctgg  aagatcagaa  ccgggaattc  atggttttcg  cccatgctca  atggaaagca  300
caggcacaaa  gtatattttc  tctattaatg  agttcatcca  gtggttttct  tgacttattt  360
ttttcgcatt  gcaggagttt  gtttaatgac  cgaaaattag  tagaatactt  aaaggagagt  420
tcttttgatg  cagtgtttct  ggatccttt  gatacctgtg  gcttaattgt  tgctaaatat  480
ttctccctcc  cctctgtggt  cttcaccagg  ggaatatttt  gccaccatct  tgaagaaggt  540
gcacagtgcc  ctgctcctct  ttcctatgtc  cccaatgatc  tcttagggtt  ctcagatgcc  600
atgactttca  aggagagagt  atggaaccac  atcgtgcact  tggaggacca  tttatttttgc  660
cagtatcttt  ttagaaatgc  cctagaaata  gcctctgaaa  ttctccaaac  ccctgtcacg  720
gcatatgatc  tctacagtca  cacatcaatt  tggttgttgc  gaacggactt  tgttttggac  780
tatcccaaac  ccgtgatgcc  caacatgatc  ttcattggtg  gtatcaactg  tcatcaggga  840
aagccattgc  ctatggaatt  tgaagcctac  attaatgctt  ctggagaaca  tggaattgtg  900
gttttctctt  tgggatcaat  ggtctcagaa  attccagaga  agaaagctat  ggcaattgct  960
gatgctttgg  gcaaaatccc  tcagacagtc  ctgtggcggt  acactggaac  ccgaccatcg  1020
aatcttgcga  acaacacgat  acttgttaag  tggctacccc  aaaacgatct  gcttggtcac  1080
ccgatgaccc  gtgcctttat  cacccatgct  ggttccatg  gtgtttatga  aagcatatgc  1140
aatggcgttc  ccatggtgat  gatgcccttg  tttggtgatc  agatggacaa  tgcaaagcgc  1200
atggagacta  agggagctgg  agtgaccctg  aatgttctgg  aaatgacttc  tgaagattta  1260
gaaaatgctc  taaaagcagt  catcaatgac  aaaagttaca  aggagaacat  catgcgcctc  1320
tccagccttc  acaaggaccg  cccggtggag  ccgctggacc  tggccgtgtt  ctgggtggag  1380
tttgtgatga  ggcacaaggg  cgcgccacac  ctgcgccccg  cagcccacga  cctcacctgg  1440
taccagtacc  attccttgga  cgtgattggt  ttcctccttg  ccgtcgtgct  gacagtggcc  1500
ttcatcacct  ttaaatgttg  tgcttatggc  taccggaaat  gcttgggaa  aaaagggcga  1560
gttaagaaag  cccacaaatc  caagacccat  tga                              1593

SEQ ID NO: 2            moltype = AA  length = 530
FEATURE                 Location/Qualifiers
source                  1..530
                        mol_type = protein
                        organism = Homo sapiens
```

```
SEQUENCE: 2
MARAGWTSPV PLCVCLLLTC GFAEAGKLLV VPMDGSHWFT MQSVVEKLIL RGHEVVVVMP    60
EVSWQLERSL NCTVKTYSTS YTLEDQNREF MVFAHAQWKA QAQSIFSLLM SSSSGFLDLF   120
FSHCRSLFND RKLVEYLKES SFDAVFLDPF DTCGLIVAKY FSLPSVVFTR GIFCHHLEEG   180
AQCPAPLSYV PNDLLGFSDA MTFKERVWNH IVHLEDHLFC QYLFRNALEI ASEILQTPVT   240
AYDLYSHTSI WLLRTDFVLD YPKPVMPNMI FIGGINCHQG KPLPMEFEAY INASGEHGIV   300
VFSLGSMVSE IPEKKAMAIA DALGKIPQTV LWRYTGTRPS NLANNTILVK WLPQNDLLGH   360
PMTRAFITHA GSHGVYESIC NGVPMVMMPL FGDQMDNAKR METKGAGVTL NVLEMTSEDL   420
ENALKAVIND KSYKENIMRL SSLHKDRPVE PLDLAVFWVE FVMRHKGAPH LRPAAHDLTW   480
YQYHSLDVIG FLLAVVLTVA FITFKCCAYG YRKCLGKKGR VKKAHKSKTH              530

SEQ ID NO: 3            moltype = DNA   length = 1593
FEATURE                 Location/Qualifiers
source                  1..1593
                        mol_type = genomic DNA
                        organism = Homo sapiens
SEQUENCE: 3
atggcttgca cagggtggac cagcccccctt cctctatgtg tgtgtctgct gctgacctgt    60
ggctttgccg aggcagggaa gctactggta gtgcccatgg atgggagcca ctggttcacc   120
atgaggtcgg tggtggagaa actcattctc aggggggcatg aggtggttgt agtcatgcca  180
gaggtgagtt ggcaactggg aagatcactg aattgcacag tgaagactta ttcaacttca   240
tatacccctgg aggatctgga ccgggagttc aaggctttta ccccatgctca atggaaagca   300
caagtacgaa gtatatattc tctattaatg ggttcataca atgacatttt tgacttattt   360
ttttcaaatt gcaggagttt gtttaaagac aaaaaaattag tagaatactt aaaggagagt  420
tcttttgatg cagtgtttct cgatccttttt gataactgtg gcttaattgt tgccaaatat  480
ttctccctcc cctccgtggt cttcgccagg ggaaatacttc ccactatct tgaagaaggt  540
gcacagtgcc ctgctcctct ttcctatgtc cccagaattc tcttagggtt ctcagatgcc   600
atgactttca aggagagagt acggaaccac atcatgcact tggaggaaca tttattatgc   660
caccgttttt tcaaaaatgc cctagaaata gcctctgaaa ttctccaaac acctgttacg   720
gagtatgatc tctacagcca cacatcaatt tggttgttgc gaaacgactt tgttttgacg   780
tatcccaaac ccgtgatgcc caacatgatc ttcattggtg gtatcaactg ccatcaggga   840
aagccgttgc ctatggaatt tgaagcctac attaatgctt ctggagaaca tggaattgtg   900
gttttctctt tgggatcaat ggtctcagaa attccagaga gaaagctat ggcaattgct   960
gatgctttgg gcaaaatccc tcagacagtc ctgtggcggt acactggaac ccgaccatcg  1020
aatcttgcga acaacacgat acttgttaag tggctacccc aaaacgatct gcttggtcac  1080
ccgatgaccc gtgccttttat cacccatgct ggttcccatg gtgtttatga agcatatgc   1140
aatggcgttc ccatggtgat gatgcccttg tttggtgatc agatggacaa tgcaaagcgc  1200
atggagacta agggagctgg agtgaccctg aatgttctgg aaatgacttc tgaagattta  1260
gaaaatgctc taaaagcagt catcaatgac aaaagttaca aggaaacat catgcgcctc   1320
tccagccttc acaaggaccg cccggtggag ccgctggacc tggccgtgtt ctgggtggga  1380
tttgtgatga gcacaaggg cgccgccac ctgcgcccg cagcccacga cctcacctgg    1440
taccagtacc attccttgga cgtgattggt ttcctcttgg ccgtcgtgct gacagtggcc   1500
ttcatcacct ttaaatgttg tgcttatggc taccggaaat gcttggggaa aaaagggcga  1560
gttaagaaag cccacaaatc caagacccat tga                               1593

SEQ ID NO: 4            moltype = AA    length = 530
FEATURE                 Location/Qualifiers
source                  1..530
                        mol_type = protein
                        organism = Homo sapiens
SEQUENCE: 4
MACTGWTSPL PLCVCLLLTC GFAEAGKLLV VPMDGSHWFT MRSVVEKLIL RGHEVVVVMP    60
EVSWQLGRSL NCTVKTYSTS YTLEDLDREF KAFAHAQWKA QVRSIYSLLM GSYNDIFDLF   120
FSNCRSLFKD KKLVEYLKES SFDAVFLDPF DNCGLIVAKY FSLPSVVFAR GILCHYLEEG   180
AQCPAPLSYV PRILLGFSDA MTFKERVRNH IMHLEEHLFC HRFFKNALEI ASEILQTPVT   240
EYDLYSHTSI WLLRTDFVLD YPKPVMPNMI FIGGINCHQG KPLPMEFEAY INASGEHGIV   300
VFSLGSMVSE IPEKKAMAIA DALGKIPQTV LWRYTGTRPS NLANNTILVK WLPQNDLLGH   360
PMTRAFITHA GSHGVYESIC NGVPMVMMPL FGDQMDNAKR METKGAGVTL NVLEMTSEDL   420
ENALKAVIND KSYKENIMRL SSLHKDRPVE PLDLAVFWVE FVMRHKGAPH LRPAAHDLTW   480
YQYHSLDVIG FLLAVVLTVA FITFKCCAYG YRKCLGKKGR VKKAHKSKTH              530

SEQ ID NO: 5            moltype = DNA   length = 1593
FEATURE                 Location/Qualifiers
source                  1..1593
                        mol_type = genomic DNA
                        organism = Homo sapiens
SEQUENCE: 5
atggctcgca cagggtggac cagccccatt cccctatgtg tttctctgct gctgacctgt    60
ggctttgctg aggcagggaa gctgctggta gtgcccatgg atgggagtca ctggttcacc   120
atgcagtcgg tggtggagaa acttatcctc aggggggcatg aggtggttgt agtcatgcca  180
gaggtgagtt ggcaactggg aaaatcactg aattgcacag tgaagactta ctcaacctca   240
tacactctgg aggatctgga ccgggaattc atggatttcg ccgatgctca atggaaagca   300
caagtacgaa gtatttgtttc tctatttctg agttcatcca atggtttttt taactttattt  360
ttttcgcatt gcaggagttt gtttaatgac cgaaaattag taagaatactt aaaggagagt   420
tcttttgatg cggtgtttct tgatccttttt gatgcctgtg gcttaattgt tgccaaatat  480
ttctccctcc cctccgtggt cttcgccagg ggaatagctt gccactatct tgaagaaggt  540
gcacagtgcc ctgctcctct ttcctatgtc cccagaattc tcttagggtt ctcagatgcc   600
atgactttca aggagagagt acggaaccac atcatgcact tggaggaaca tttatttgc   660
cagtattttt ccaaaaatgc cctagaaata gcctctgaaa ttctccaaac acctgtcaca   720
```

-continued

```
gcatatgatc tctacagcca cacatcaatt tggttgttgc gaacagactt tgttttggac    780
tatcccaaac ccgtgatgcc caatatgatc ttcattggtg gtatcaactg ccatcaggga    840
aagccattgc ctatggaatt tgaagcctac attaatgctt ctggagaaca tggaattgtg    900
gttttctctt tgggatcaat ggtctcagaa attccagaga agaaagctat ggcaattgct    960
gatgctttgg gcaaaatccc tcagacagtc ctgtggcggt acactggaac ccgaccatcg   1020
aatcttgcga caacacgat  acttgttaag tggctacccc aaaacgatct gcttggtcac   1080
ccgatgaccc gtgcctttat cacccatgct ggttcccatg gtgtttatga aagcatatgc   1140
aatggcgttc ccatggtgat gatgcccttg tttggtgatc agatggacaa tgcaaagcgc   1200
atggagacta agggagctgg agtgaccctg aatgttctgg aaatgacttc tgaagattta   1260
gaaaatgctc taaaagcagt catcaatgac aaaagttaca aggagaacat catgcgcctc   1320
tccagccttc acaaggaccg cccggtggag ccgctggacc tggccgtgtt ctgggtggag   1380
tttgtgatga ggcacaaggg cgcgccacac ctgcgccccg cagcccacga cctcacctgg   1440
taccagtacc attccttgga cgtgattggt ttcctcttgg ccgtcgtgct gacagtggcc   1500
ttcatcacct ttaaatgttg tgcttatggc taccggaaat gcttgggaa  aaaagggcga   1560
gttaagaaag cccacaaatc caagacccat tga                                1593

SEQ ID NO: 6        moltype = AA  length = 530
FEATURE             Location/Qualifiers
source              1..530
                    mol_type = protein
                    organism = Homo sapiens
SEQUENCE: 6
MARTGWTSPI PLCVSLLLTC GFAEAGKLLV VPMDGSHWFT MQSVVEKLIL RGHEVVVMP     60
EVSWQLGKSL NCTVKTYSTS YTLEDLDREF MDFADAQWKA QVRSLFSLFL SSSNGFFNLF   120
FSHCRSLFND RKLVEYLKES SFDAVFLDPF DACGLIVAKY FSLPSVVFAR GIACHYLEEG   180
AQCPAPLSYV PRILLGFSDA MTFKERVRNH IMHLEEHLFC QYFSKNALEI ASEILQTPVT   240
AYDLYSHTSI WLLRRTDFVLD YPKPVMPNMI FIGGINCHQG KPLPMEFEAY INASGEHGIV   300
VFSLGSMVSE IPEKKAMAIA DALGKIPQTV LWRYTGTRPS NLANNTILVK WLPQNDLLGH   360
PMTRAFITHA GSHGVYESIC NGVPMVMMPL FGDQMDNAKR METKGAGVTL NVLEMTSEDL   420
ENALKAVIND KSYKENIMRL SSLHKDRPVE PLDLAVFWVE FVMRHKGAPH LRPAAHDLTW   480
YQYHSLDVIG FLLAVVLTVA FITFKCCAYG YRKCLGKKGR VKKAHSKTH               530

SEQ ID NO: 7        moltype = DNA  length = 1593
FEATURE             Location/Qualifiers
source              1..1593
                    mol_type = genomic DNA
                    organism = Homo sapiens
SEQUENCE: 7
atggctcgtg cagggtggac tggcctcctt ccctatatg  tgtgtctact gctgacctgt     60
ggctttgcca aggcagggaa gctgctggta gtgcccatgg atgggagcca ctggttcacc    120
atgcagtcgg tggtggagaa actcatcctc aggggggcatg aggtggtcgt agtcatgcca   180
gaggtgagtt ggcaactggg aagatcactg aattgcacag tgaagactta ctcaacctca    240
tacactctgg aggatcagga ccgggagttc atggttttta ccgatgctcg tggacgggca    300
ccattgcgaa gtgcattttc tctattaaca agttcatcca atggtatttt tgacttattt    360
ttttcaaatt gcaggagttt gtttaatgac cgaaaattag tagaatactt aaaggagagt    420
tgttttgatg cagtgttttct cgatccttttt gatgcctgtg gcttaattgt tgccaaatat    480
ttctcctcc  cctctgtggt cttcgccagg ggaatatttt gccactatct tgaagaaggt    540
gcacagtgcc ctgctcctct ttcctatgtc cccagacttc tcttagggtt ctcagacgcc    600
atgactttca aggagagagt atggaaccac atcatgcact tggaggaaca tttatttgc     660
ccctattttt tcaaaaatgt cttagaaata gcctctgaaa ttctccaaac ccctgtcacg    720
gcatatgatc tctacagcca cacatcaatt tggttgttgc gaactgactt tgttttggac    780
tatcccaaac ccgtgatgcc caatatgatc ttcattggtg gtatcaactg tcatcaggga    840
aagccagtgc ctatggaatt tgaagcctac attaatgctt ctggagaaca tggaattgtg    900
gttttctctt tgggatcaat ggtctcagaa attccagaga agaaagctat ggcaattgct    960
gatgctttgg gcaaaatccc tcagacagtc ctgtggcggt acactggaac ccgaccatcg   1020
aatcttgcga caacacgat  acttgttaag tggctacccc aaaacgatct gcttggtcac   1080
ccgatgaccc gtgcctttat cacccatgct ggttcccatg gtgtttatga aagcatatgc   1140
aatggcgttc ccatggtgat gatgcccttg tttggtgatc agatggacaa tgcaaagcgc   1200
atggagacta agggagctgg agtgaccctg aatgttctgg aaatgacttc tgaagattta   1260
gaaaatgctc taaaagcagt catcaatgac aaaagttaca aggagaacat catgcgcctc   1320
tccagccttc acaaggaccg cccggtggag ccgctggacc tggccgtgtt ctgggtggag   1380
tttgtgatga ggcacaaggg cgcgccacac ctgcgccccg cagcccacga cctcacctgg   1440
taccagtacc attccttgga cgtgattggt ttcctcttgg ccgtcgtgct gacagtggcc   1500
ttcatcacct ttaaatgttg tgcttatggc taccggaaat gcttgggaa  aaaagggcga   1560
gttaagaaag cccacaaatc caagacccat tga                                1593

SEQ ID NO: 8        moltype = AA  length = 530
FEATURE             Location/Qualifiers
source              1..530
                    mol_type = protein
                    organism = Homo sapiens
SEQUENCE: 8
MARAGWTGLL PLYVCLLLTC GFAKAGKLLV VPMDGSHWFT MQSVVEKLIL RGHEVVVMP     60
EVSWQLGRSL NCTVKTYSTS YTLEDQDREF MVFADARWTA PLRSAFSLLT SSSNGIFDLF   120
FSNCRSLFND RKLVEYLKES CFDAVFLDPF DACGLIVAKY FSLPSVVFAR GIFCHYLEEG   180
AQCPAPLSYV PRLLLGFSDA MTFKERVWNH IMHLEEHLFC PYFFKNVLEI ASEILQTPVT   240
AYDLYSHTSI WLLRRTDFVLE YPKPVMPNMI FIGGINCHQG KPVPMEFEAY INASGEHGIV   300
VFSLGSMVSE IPEKKAMAIA DALGKIPQTV LWRYTGTRPS NLANNTILVK WLPQNDLLGH   360
PMTRAFITHA GSHGVYESIC NGVPMVMMPL FGDQMDNAKR METKGAGVTL NVLEMTSEDL   420
```

```
                                                    -continued
ENALKAVIND KSYKENIMRL SSLHKDRPVE PLDLAVFWVE FVMRHKGAPH LRPAAHDLTW  480
YQYHSLDVIG FLLAVVLTVA FITFKCCAYG YRKCLGKKGR VKKAHKSKTH             530

SEQ ID NO: 9            moltype = DNA  length = 1599
FEATURE                 Location/Qualifiers
source                  1..1599
                        mol_type = genomic DNA
                        organism = Homo sapiens
SEQUENCE: 9
atggcctgcc tccttcgctc atttcagaga atttctgcag gggttttctt cttagcactt   60
tggggcatgg ttgtaggtga caagctgctg gtggtccctc aggacggaag ccactggctt  120
agtatgaagg atatagttga ggttctcagt gaccggggtc atgagattgt agtggtggtg  180
cctgaagtta atttgctttt gaaagaatcc aaatactaca aagaaaaat ctatccagtg   240
ccgtatgacc aagaagagct gaagaaccgt taccaatcat ttggaaacaa tcactttgct  300
gagcgatcat tcctaactgc tcctcagaca gagtacagga ataacatgat tgttattggc  360
ctgtacttca tcaactgcca gagcctcctg caggacaggg acaccctgaa cttctttaag  420
gagagcaagt ttgatgctct tttcacagac ccagccttac cctgtggggt gatcctggct  480
gagtatttgg gcctaccatc tgtgtacctc ttcaggggtt ttccgtgttc cctggagcat  540
acattcagca gaagcccaga ccctgtgtcc tacattccca ggtgctacac aaagttttca  600
gaccacatga cttttcccca acgagtggcc aacttccttg ttaatttgtt ggagccctat  660
ctatttatt gtctgtttc aaagtatgaa gaactcgcat cagctgtcct caagagagat   720
gtggatataa tcaccttata tcagaaggtc tctgtttggc tgttaagata tgactttgtg  780
cttgaatatc ctaggccggt catgcccaac atggtcttca ttggaggtat caactgtaag  840
aagaggaaag acttgtctca ggaatttgaa gcctacatta atgcttctgg agaacatgga  900
attgtggttt tctctttggg atcaatggtc tcagaaattc cagagaagaa agctatggca  960
attgctgatg cttttgggcaa aatccctcag acagtcctgt ggcggtacac tggaacccga 1020
ccatcgaatc ttgcgaacaa cacgatactt gttaagtggc taccccaaaa cgatctgctt 1080
ggtcacccga tgaccgtgc ctttatcacc catgctggtt cccatggtgt ttatgaaagc  1140
atatgcaatg gcgttcccat ggtgatgatg cccttgtttg gtgatcagat ggacaatgca 1200
aagcgcatga agactaaggg agctggagtg accctgaatg ttctggaaat gacttctgaa 1260
gatttagaaa atgctctaaa agcagtcatc aatgacaaaa gttacaagga gaacatcatg 1320
cgcctctcca gccttcacaa ggaccgcccg gtggagccgc tggacctggc cgtgttctgg 1380
gtggagtttg tgatgaggca caagggcgcg ccacacctgc gccccgcagc ccacgacctc 1440
acctggtacc agtaccattc cttggacgtg attggttttcc tcttggccgt cgtgctgaca 1500
gtggccttca tcacctttaa atgttgtgct tatggctacc ggaaatgctt ggggaaaaaa 1560
gggcgagtta agaaagccca caatccaag accattga                          1599

SEQ ID NO: 10           moltype = AA  length = 532
FEATURE                 Location/Qualifiers
source                  1..532
                        mol_type = protein
                        organism = Homo sapiens
SEQUENCE: 10
MACLLRSFQR ISAGVFFLAL WGMVVGDKLL VVPQDGSHWL SMKDIVEVLS DRGHEIVVVV   60
PEVNLLLKES KYYTRKIYPV PYDQEELKNR YQSFGNNHFA ERSFLTAPQT EYRNNMIVIG  120
LYFINCQSLL QDRDTLNFFK ESKFDALFTD PALPCGVILA EYLGLPSVYL FRGFPCSLEH  180
TFSRSPDPVS YIPRCYTKFS DHMTFSQRVA NFLVNLLEPY LFYCLFSKYE ELASAVLKRD  240
VDIITLYQKV SVWLLRYDFV LEYPRPVMPN MVFIGGINCK KRKDLSQEFE AYINASGEHG  300
IVVFSLGSMV SEIPEKKAMA IADALGKIPQ TVLWRYTGTR PSNLANNTIL VKWLPQNDLL  360
GHPMTRAFIT HAGSHGVYES ICNGVPMVMM PLFGDQMDNA KRMETKGAGV TLNVLEMTSE  420
DLENALKAVI NDKSYKENIM RLSSLHKDRP VEPLDLAVFW VEFVMRHKGA PHLRPAAHDL  480
TWYQYHSLDV IGFLLAVVLT VAFITFKCCA YGYRKCLGKK GRVKKAHKSK TH          532
```